United States Patent
Almansa-Rosales et al.

(10) Patent No.: US 10,189,828 B2
(45) Date of Patent: Jan. 29, 2019

(54) 1-METHYLPYRAZOLE-PIPERAZINE COMPOUNDS HAVING MULTIMODAL ACTIVITY AGAINST PAIN

(71) Applicant: LABORATORIOS DEL DR. ESTEVE S.A., Barcelona (ES)

(72) Inventors: Carmen Almansa-Rosales, Barcelona (ES); Monica Garcia-Lopez, Barcelona (ES); Lourdes Garriga-Sanahuja, Barcelona (ES); Ana Virginia Llorente-Fernandez, Barcelona (ES)

(73) Assignee: LABORATORIOS DEL DR. ESTEVE S.A., Barcelona (ES)

( * ) Notice: Subject to any disclaimer, the term of this patent is extended or adjusted under 35 U.S.C. 154(b) by 0 days.

(21) Appl. No.: 15/531,571

(22) PCT Filed: Dec. 15, 2015

(86) PCT No.: PCT/EP2015/002525
§ 371 (c)(1),
(2) Date: May 30, 2017

(87) PCT Pub. No.: WO2016/096126
PCT Pub. Date: Jun. 23, 2016

(65) Prior Publication Data
US 2017/0362215 A1 Dec. 21, 2017

(30) Foreign Application Priority Data
Dec. 15, 2014 (EP) .................................. 14382515

(51) Int. Cl.
| | | |
|---|---|---|
| *C07D 231/12* | (2006.01) | |
| *C07D 401/12* | (2006.01) | |
| *C07D 401/14* | (2006.01) | |
| *C07D 403/06* | (2006.01) | |
| *C07D 403/14* | (2006.01) | |
| *C07D 417/12* | (2006.01) | |
| *A61K 31/4523* | (2006.01) | |
| *A61K 31/496* | (2006.01) | |
| *C07D 417/14* | (2006.01) | |
| *C07D 401/06* | (2006.01) | |

(52) U.S. Cl.
CPC ........ *C07D 417/12* (2013.01); *A61K 31/4523* (2013.01); *A61K 31/496* (2013.01); *C07D 231/12* (2013.01); *C07D 401/06* (2013.01); *C07D 401/12* (2013.01); *C07D 401/14* (2013.01); *C07D 403/06* (2013.01); *C07D 417/14* (2013.01)

(58) Field of Classification Search
CPC .. C07D 231/12; C07D 401/12; C07D 401/14; C07D 403/06; C07D 403/14; C07D 417/12
See application file for complete search history.

(56) References Cited

FOREIGN PATENT DOCUMENTS

| | | |
|---|---|---|
| CN | 1371903 | 10/2002 |
| EP | 2353598 | 8/2011 |

OTHER PUBLICATIONS

Bourrain. S., et al., Bioorganic and Medicinal Chemistry, vol. 6, No. 6, pg. 1731-1743, Oct. 1, 1998.
Giron, R., et al., Life Sciences, vol. 71, No. 9, p. 1023-1034, Jul. 19, 2002.
International Search Report for PCT/EP2015/002525 dated Mar. 2, 2016.
Jagerovis, Nadine, et al., Bioorganic and Medicinal Chemistry, vol. 10, p. 817-827, 2002.
Bornot, et al., J. Med. Chem, 56, 1197-1210 (2013).
Chien, et al., Neurosci. Lett. 190, 137-9 (1995).
DIckenson, et al., Eur J Pain 9, 113-6 (2005).
Goldberg, et al., BMC Public Health, 11, 770 (2011).
Mao, et al., J. Pain 12, 157-166 (2011).
Turk, et al., Lancet, 377, 2226-2235 (2011).
Zamanillo, et al., Eur. J. Pharmacol, 716, 78-93 (2013).

*Primary Examiner* — Brenda L Coleman
(74) *Attorney, Agent, or Firm* — Hueschen and Sage

(57) ABSTRACT

The present invention relates to 1-methylpyrazole-piperazine compounds having dual pharmacological activity towards both the sigma (σ) receptor, and the μ-opiod receptor, to processes of preparation of such compounds, to pharmaceutical compositions comprising them, and to their use in therapy, in particular for the treatment of pain.

21 Claims, No Drawings

1-METHYLPYRAZOLE-PIPERAZINE COMPOUNDS HAVING MULTIMODAL ACTIVITY AGAINST PAIN

FIELD OF THE INVENTION

The present invention relates to compounds having dual pharmacological activity towards both the sigma (σ) receptor, and the μ-opiod receptor (MOR or mu-opioid receptor) and more particularly to 1-methylpyrazole-piperazine derivatives having this pharmacological activity, to processes of preparation of such compounds, to pharmaceutical compositions comprising them, and to their use in therapy, in particular for the treatment of pain.

BACKGROUND OF THE INVENTION

The adequate management of pain constitutes an important challenge, since currently available treatments provide in many cases only modest improvements, leaving many patients unrelieved [Turk D C, Wilson H D, Cahana A. Treatment of chronic non-cancer pain. *Lancet* 377, 2226-2235 (2011)]. Pain affects a big portion of the population with an estimated prevalence of around 20% and its incidence, particularly in the case of chronic pain, is increasing due to the population ageing. Additionally, pain is clearly related to comorbidities, such as depression, anxiety and insomnia, which lead to important productivity losses and socio-economical burden [Goldberg D S, McGee S J. Pain as a global public health priority. *BMC Public Health.* 11, 770 (2011)]. Existing pain therapies include non-steroidal anti-inflammatory drugs (NSAIDs), opioid agonists, calcium channel blockers and antidepressants, but they are much less than optimal regarding their safety ratio. All of them show limited efficacy and a range of secondary effects that preclude their use, especially in chronic settings.

As mentioned before, there are few available therapeutic classes for the treatment of pain, and opioids are among the most effective, especially when addressing severe pain states. They act through three different types of opioid receptors (mu, kappa and gamma) which are transmembrane G-protein coupled receptors (GPCRs). Still, the main analgesic action is attributed to the activation of the μ-opioid receptor (MOR). However, the general administration of MOR agonists is limited due to their important side effects, such as constipation, respiratory depression, tolerance, emesis and physical dependence [Meldrum, M. L. (Ed.). Opioids and Pain Relief: A Historical Perspective. Progress in Pain Research and Management, Vol 25. IASP Press, Seattle, 2003]. Additionally, MOR agonists are not optimal for the treatment of chronic pain as indicated by the diminished effectiveness of morphine against chronic pain conditions. This is especially proven for the chronic pain condiditions of neuropathic or inflammatory origin, in comparison to its high potency against acute pain. The finding that chronic pain can lead to MOR down-regulation may offer a molecular basis for the relative lack of efficacy of morphine in long-term treatment settings [Dickenson, A. H., Suzuki, R. Opioids in neuropathic pain: Clues from animal studies. *Eur J Pain* 9, 113-6 (2005)]. Moreover, prolonged treatment with morphine may result in tolerance to its analgesic effects, most likely due to treatment-induced MOR down-regulation, internalization and other regulatory mechanisms. As a consequence, long-term treatment can result in substantial increases in dosing in order to maintain a clinically satisfactory pain relief, but the narrow therapeutic window of MOR agonists finally results in unacceptable side effects and poor patient compliance.

The sigma-1 ($\sigma_1$) receptor was discovered 35 years ago and initially assigned to a new subtype of the opioid family, but later on and based on the studies of the enantiomers of SKF-10,047, its independent nature was established. The first link of the or receptor to analgesia was established by Chien and Pasternak [Chien C C, Pasternak G W. Sigma antagonists potentiate opioid analgesia in rats. *Neurosci. Lett.* 190, 137-9 (1995)], who described it as an endogenous anti-opioid system, based on the finding that $\sigma_1$ receptor agonists counteracted opioid receptor mediated analgesia, while $\sigma_1$ receptor antagonists, such as haloperidol, potentiated it.

Many additional preclinical evidences have indicated a clear role of the $\sigma_1$ receptor in the treatment of pain [Zamanillo D, Romero L, Merlos M, Vela J M. Sigma 1 receptor: A new therapeutic target for pain. *Eur. J. Pharmacol,* 716, 78-93 (2013)]. The development of the $\sigma_1$ receptor knockout mice, which show no obvious phenotype and perceive normally sensory stimuli, was a key milestone in this endeavour. In physiological conditions the responses of the $\sigma_1$ receptor knockout mice to mechanical and thermal stimuli were found to be undistinguishable from WT ones but they were shown to possess a much higher resistance to develop pain behaviours than WT mice when hypersensitivity entered into play. Hence, in the $\sigma_1$ receptor knockout mice capsaicin did not induce mechanical hypersensitivity, both phases of formalin-induced pain were reduced, and cold and mechanical hypersensitivity were strongly attenuated after partial sciatic nerve ligation or after treatment with paclitaxel, which are models of neuropathic pain. Many of these actions were confirmed by the use of $\sigma_1$ receptor antagonists and led to the advancement of one compound, S1RA, into clinical trials for the treatment of different pain states. Compound S1RA exerted a substantial reduction of neuropathic pain and anhedonic state following nerve injury (i.e., neuropathic pain conditions) and, as demonstrated in an operant self-administration model, the nerve-injured mice, but not sham-operated mice, acquired the operant responding to obtain it (presumably to get pain relief), indicating that $\sigma_1$ receptor antagonism relieves neuropathic pain and also address some of the comorbidities (i.e., anhedonia, a core symptom in depression) related to pain states.

Pain is multimodal in nature, since in nearly all pain states several mediators, signaling pathways and molecular mechanisms are implicated. Consequently, monomodal therapies fail to provide complete pain relief. Currently, combining existing therapies is a common clinical practice and many efforts are directed to assess the best combination of available drugs in clinical studies [Mao J, Gold MS, Backonja M. Combination drug therapy for chronic pain: a call for more clinical studies. *J. Pain* 12, 157-166 (2011)]. Hence, there is an urgent need for innovative therapeutics to address this unmet medical need.

As mentioned previously, opioids are among the most potent analgesics but they are also responsible for various adverse effects which seriously limit their use.

Accordingly, there is still a need to find compounds that have an alternative or improved pharmacological activity in the treatment of pain, being both effective and showing the desired selectivity, and having good "drugability" properties, i.e. good pharmaceutical properties related to administration, distribution, metabolism and excretion.

Thus, the technical problem can therefore be formulated as finding compounds that have an alternative or improved pharmacological activity in the treatment of pain.

In view of the existing results of the currently available therapies and clinical practices, the present invention offers a solution by combining in a single compound binding to two different receptors relevant for the treatment of pain. This was mainly achieved by providing the compounds according to the invention that bind both to the μ-opiod receptor and to the $\sigma_1$ receptor.

SUMMARY OF THE INVENTION

In this invention a family of structurally distinct 1-methylpyrazole-piperazine derivatives which have a dual pharmacological activity towards both the sigma (σ) receptor, and the μ-opiod receptor was identified thus solving the above problem of identifying alternative or improved pain treatments by offering such dual compounds.

The invention is in one aspect directed to a compound having a dual activity binding to the $\sigma_1$ receptor and the μ-opioid receptor for use in the treatment of pain.

As this invention is aimed at providing a compound or a chemically related series of compounds which act as dual ligands of the $\sigma_1$ receptor and the μ-opioid receptor it is a very preferred embodiment if the compound has a binding expressed as $K_i$ which is preferably <1000 nM for both receptors, more preferably <500 nM, even more preferably <100 nM.

The invention is directed in a main aspect to a compound of general formula (I),

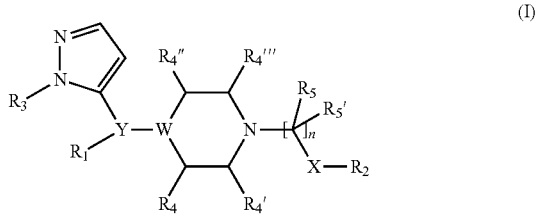

wherein $R_1$, $R_2$, $R_3$, $R_4$, $R_{4'}$, $R_{4''}$, $R_{4'''}$, $R_5$, $R_{5'}$, W, X, Y and n are as defined below in the detailed description.

DETAILED DESCRIPTION OF THE INVENTION

The invention is directed to a family of structurally distinct 1-methylpyrazole-piperazine derivatives which have a dual pharmacological activity towards both the sigma (σ) receptor and the μ-opiod receptor, thus solving the above problem of identifying alternative or improved pain treatments by offering such dual compounds.

The invention is in one aspect directed to a compound having a dual activity binding to the $\sigma_1$ receptor and the μ-opioid receptor for use in the treatment of pain.

As this invention is aimed at providing a compound or a chemically related series of compounds which act as dual ligands of the $\sigma_1$ receptor and the μ-opioid receptor it is a preferred embodiment if the compound has a binding expressed as $K_i$ which is preferably <1000 nM for both receptors, more preferably <500 nM, even more preferably <100 nM.

The applicant has surprisingly found that the problem on which the present invention is based can be solved by using a multimodal balanced analgesic approach combining two different synergistic activities in a single drug (i.e., dual ligands which are bifunctional and bind to μ-opioid receptor and to $\sigma_1$ receptor), thereby enhancing the opioid analgesia through the $\sigma_1$ activation without increasing the undesirable side effects. This supports the therapeutic value of a dual MOR/$\sigma_1$ receptor compound whereby the $\sigma_1$ receptor binding component acts as an intrinsic adjuvant of the MOR binding component.

This solution offered the advantage that the two mechanisms complement each other in order to treat pain and chronic pain using lower and better tolerated doses needed based on the potentiation of analgesia but avoiding the adverse events of μ-opioid receptor agonists.

A dual compound that possess binding to both the μ-opiod receptor and to the $\sigma_1$ receptor shows a highly valuable therapeutic potential by achieving an outstanding analgesia (enhanced in respect to the potency of the opioid component alone) with a reduced side-effect profile (safety margin increased compared to that of the opioid component alone) versus existing opioid therapies.

Advantageously, the dual compounds according to the present invention would in addition show one or more the following functionalities: $\sigma_1$ receptor antagonism and μ-opioid receptor agonism. It has to be noted, though, that both functionalities "antagonism" and "agonism" are also subdivided in their effect into subfunctionalities like partial agonism or inverse agonism. Accordingly, the functionalities of the dual compound should be considered within a relatively broad bandwidth.

An antagonist on one of the named receptors blocks or dampens agonist-mediated responses. Known subfunctionalities are neutral antagonists or inverse agonists.

An agonist on one of the named receptors increases the activity of the receptor above its basal level. Known subfunctionalities are full agonists, or partial agonists.

In addition, the two mechanisms complement each other since MOR agonists are only marginally effective in the treatment of neuropathic pain, while $\sigma_1$ receptor antagonists show outstanding effects in preclinical neuropathic pain models. Thus, the $\sigma_1$ receptor component adds unique analgesic actions in opioid-resistant pain. Finally, the dual approach has clear advantages over MOR agonists in the treatment of chronic pain as lower and better tolerated doses would be needed based on the potentiation of analgesia but not of the adverse events of MOR agonists.

A further advantage of using designed multiple ligands is a lower risk of drug-drug interactions compared to cocktails or multi-component drugs, thus involving simpler pharmacokinetics and less variability among patients. Additionally, this approach may improve patient compliance and broaden the therapeutic application in relation to monomechanistic drugs, by addressing more complex aetiologies. It is also seen as a way of improving the R&D output obtained using the "one drug-one target" approach, which has been questioned over the last years [Bornot A, Bauer U, Brown A, Firth M, Hellawell C, Engkvist O. Systematic Exploration of Dual-Acting Modulators from a Combined Medicinal Chemistry and Biology Perspective. J. Med. Chem, 56, 1197-1210 (2013)].

In a particular aspect, the present invention is directed to compounds of general formula (I):

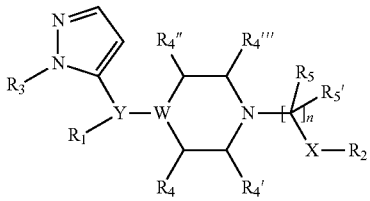

(I)

wherein
n is 1, 2, 3, 4, 5 or 6;
Y—W is $CR_y$—N or N—$CR_w$;
X is a bond or —$CR_6R_{6'}$—;
$R_1$ is substituted or unsubstituted cycloalkyl, substituted or unsubstituted aryl, or substituted or unsubstituted heterocyclyl;
$R_2$ is substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl or substituted or unsubstituted heterocyclyl;
$R_3$ is hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl, substituted or unsubstituted heterocyclyl, substituted or unsubstituted alkylcycloalkyl, substituted or unsubstituted alkylaryl, or substituted or unsubstituted alkylheterocyclyl;
$R_4$, $R_{4'}$, $R_{4''}$ and $R_{4'''}$ are independently selected from hydrogen or unsubstituted $C_{1-6}$ alkyl, unsubstituted $C_{2-6}$ alkenyl, and unsubstituted $C_{2-6}$ alkynyl;
$R_5$ and $R_{5'}$ are independently selected from hydrogen or unsubstituted $C_{1-6}$ alkyl, unsubstituted $C_{2-6}$ alkenyl, and unsubstituted $C_{2-6}$ alkynyl;
$R_6$ is selected from hydrogen, halogen, —$OR_7$, substituted or unsubstituted $C_{1-6}$ alkyl, substituted or unsubstituted $C_{2-6}$ alkenyl, substituted or unsubstituted $C_{2-6}$ alkynyl, —$C(O)OR_7$, —$C(O)NR_7R_{7'}$, —$NR_7C(O)R_{7'}$, and —$NR_7R_{7''}$;
$R_{6''}$ is selected from hydrogen, substituted or unsubstituted $C_{1-6}$ alkyl, substituted or unsubstituted $C_{2-6}$ alkenyl and substituted or unsubstituted $C_{2-6}$ alkynyl;
wherein $R_7$, $R_{7'}$ and $R_{7''}$ are independently selected from hydrogen, unsubstituted $C_{1-6}$ alkyl, unsubstituted $C_{2-6}$ alkenyl, unsubstituted $C_{2-6}$ alkynyl, and unsubstituted acyl;
and $R_{7'''}$ is selected from hydrogen, unsubstituted $C_{1-6}$ alkyl, unsubstituted $C_{2-6}$ alkenyl and unsubstituted $C_{2-6}$ alkynyl and -Boc;
$R_y$ is selected from hydrogen, substituted or unsubstituted $C_{1-6}$ alkyl, substituted or unsubstituted $C_{2-6}$ alkenyl, and substituted or unsubstituted $C_{2-6}$ alkynyl;
$R_w$ is selected from hydrogen, substituted or unsubstituted $C_{1-6}$ alkyl, substituted or unsubstituted $C_{2-6}$ alkenyl, and substituted or unsubstituted $C_{2-6}$ alkynyl;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In the context of this invention, and in order to avoid any issue of clarity, when Y—W is $CR_y$—N it is understood that Y—W represents

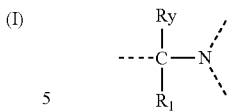

in Formula (I).

In the context of this invention, and as to avoid any issue of clarity, when Y—W is N—$CR_w$, it is understood that Y—W represents

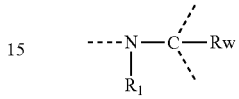

in Formula (I).

In the context of this invention, alkyl is understood as meaning saturated, linear or branched hydrocarbons, which may be unsubstituted or substituted once or several times. It encompasses e.g. —$CH_3$ and —$CH_2$—$CH_3$. In these radicals, $C_{1-2}$-alkyl represents C1- or C2-alkyl, $C_{1-3}$-alkyl represents C1-, C2- or C3-alkyl, $C_{1-4}$-alkyl represents C1-, C2-, C3- or C4-alkyl, $C_{1-5}$-alkyl represents C1-, C2-, C3-, C4-, or C5-alkyl, $C_{1-6}$-alkyl represents C1-, C2-, C3-, C4-, C5- or C6-alkyl, $C_{1-7}$-alkyl represents C1-, C2-, C3-, C4-, C5-, C6- or C7-alkyl, $C_{1-7}$-alkyl represents C1-, C2-, C3-, C4-, C5-, C6-, C7- or C8-alkyl, $C_{1-10}$-alkyl represents C1-, C2-, C3-, C4-, C5-, C6-, C7-, C8-, C9- or C10-alkyl and $C_{1-18}$-alkyl represents C1-, C2-, C3-, C4-, C5-, C6-, C7-, C8-, C9-, C10-, C11-, C12-, C13-, C14-, C15-, C16-, C17- or C18-alkyl. The alkyl radicals are preferably methyl, ethyl, propyl, methylethyl, butyl, 1-methylpropyl, 2-methylpropyl, 1,1-dimethylethyl, pentyl, 1,1-dimethylpropyl, 1,2-dimethylpropyl, 2,2-dimethylpropyl, hexyl, 1-methylpentyl, if substituted also $CHF_2$, $CF_3$ or $CH_2OH$ etc. Preferably alkyl is understood in the context of this invention as $C_{1-8}$alkyl like methyl, ethyl, propyl, butyl, pentyl, hexyl, heptyl, or octyl; preferably is $C_{1-6}$alkyl like methyl, ethyl, propyl, butyl, pentyl, or hexyl; more preferably is $C_{1-4}$alkyl like methyl, ethyl, propyl or butyl.

Alkenyl is understood as meaning unsaturated, linear or branched hydrocarbons, which may be unsubstituted or substituted once or several times. It encompasses groups like e.g. —CH=CH—$CH_3$. The alkenyl radicals are preferably vinyl (ethenyl), allyl (2-propenyl). Preferably in the context of this invention alkenyl is $C_{2-10}$-alkenyl or $C_{2-8}$-alkenyl like ethylene, propylene, butylene, pentylene, hexylene, heptylene or octylene; or is $C_{2-6}$-alkenyl like ethylene, propylene, butylene, pentylene, or hexylene; or is $C_{2-4}$-alkenyl, like ethylene, propylene, or butylenes.

Alkynyl is understood as meaning unsaturated, linear or branched hydrocarbons, which may be unsubstituted or substituted once or several times. It encompasses groups like e.g. —C≡C—$CH_3$ (1-propinyl). Preferably alkynyl in the context of this invention is $C_{2-10}$-alkynyl or $C_{2-8}$-alkynyl like ethyne, propyne, butyene, pentyne, hexyne, heptyne, or octyne; or is $C_{2-6}$-alkynyl like ethyne, propyne, butyene, pentyne, or hexyne; or is $C_{2-4}$-alkynyl like ethyne, propyne, butyene, pentyne, or hexyne.

In the context of this invention cycloalkyl is understood as meaning saturated and unsaturated (but not aromatic) cyclic hydrocarbons (without a heteroatom in the ring), which can be unsubstituted or once or several times substituted. Furthermore, $C_{3-4}$-cycloalkyl represents C3- or C4-cycloalkyl, $C_{3-5}$-cycloalkyl represents C3-, C4- or C5-cycloalkyl, $C_{3-6}$-cycloalkyl represents C3-, C4-, C5- or C6-cycloalkyl, $C_{3-7}$-cycloalkyl represents C3-, C4-, C5-, C6- or C7-cycloalkyl, $C_{3-8}$-cycloalkyl represents C3-, C4-, C5-, C6-, C7- or C8-cycloalkyl, $C_{4-5}$-cycloalkyl represents C4- or C5-cycloalkyl, $C_{4-6}$-cycloalkyl represents C4-, C5- or C6-cycloalkyl, $C_{4-7}$-cycloalkyl represents C4-, C5-, C6- or C7-cycloalkyl, $C_{5-6}$-cycloalkyl represents C5- or C6-cycloalkyl and $C_{5-7}$-cycloalkyl represents C5-, C6- or C7-cycloalkyl. Examples are cyclopropyl, 2-methylcyclopropyl, cyclopropylmethyl, cyclobutyl, cyclopentyl, cyclopentylmethyl, cyclohexyl, cycloheptyl, cyclooctyl, and also adamantly. Preferably in the context of this invention cycloalkyl is $C_{3-8}$cycloalkyl like cyclopropyl, cyclobutyl, cyclopentyl, cyclohexyl, cycloheptyl, or cyclooctyl; or is $C_{3-7}$cycloalkyl like cyclopropyl, cyclobutyl, cyclopentyl, cyclohexyl, or cycloheptyl; or is $C_{3-6}$cycloalkyl like cyclopropyl, cyclobutyl, cyclopentyl or cyclohexyl, especially cyclopentyl or cyclohexyl.

In connection with alkyl (also in alkylaryl, alkylheterocyclyl or alkylcycloalkyl), alkenyl, alkynyl and O-alkyl— unless defined otherwise—the term substituted in the context of this invention is understood as meaning replacement of at least one hydrogen radical on a carbon atom by halogen (F, Cl, Br, I), —$NR_cR_{c'''}$, —$SR_c$, —$S(O)R_c$, —$S(O)_2R_c$, —$OR_c$, —$C(O)OR_c$, —CN, —$C(O)NR_cR_{c'}$, haloalkyl, haloalkoxy or —$OC_{1-4}$alkyl being unsubstituted or substituted by one or more of —$OR_c$ or halogen (F, Cl, I, Br), being $R_c$ one of $R_9$ or $R_{10}$, (being $R_{c'}$ one of $R_{9'}$ or $R_{10'}$; being $R_{c''}$ one of $R_{9''}$ or $R_{10''}$; being $R_{c'''}$ one of $R_{9'''}$ $R_{10'''}$), wherein $R_1$ to $R_{11'''}$ and $R_y$ and $R_w$, are as defined in the description, and wherein when different radicals $R_1$ to $R_{11'''}$ and $R_y$ and $R_w$, are present simultaneously in Formula I they may be identical or different.

More than one replacement on the same molecule and also on the same carbon atom is possible with the same or different substituents. This includes for example 3 hydrogens being replaced on the same C atom, as in the case of $CF_3$, or at different places of the same molecule, as in the case of e.g. —CH(OH)—CH=CH—$CHCl_2$.

In the context of this invention haloalkyl is understood as meaning an alkyl being substituted once or several times by a halogen (selected from F, Cl, Br, I). It encompasses e.g. —$CH_2Cl$, —$CH_2F$, —$CHCl_2$, —$CHF_2$, —$CCl_3$, —$CF_3$ and —$CH_2$—$CHCl_2$. Preferably haloalkyl is understood in the context of this invention as halogen-substituted $C_{1-4}$-alkyl representing halogen substituted C1-, C2-, C3- or C4-alkyl. The halogen-substituted alkyl radicals are thus preferably methyl, ethyl, propyl, and butyl. Preferred examples include —$CH_2Cl$, —$CH_2F$, —$CHCl_2$, —$CHF_2$, and —$CF_3$.

In the context of this invention haloalkoxy is understood as meaning an —O-alkyl being substituted once or several times by a halogen (selected from F, Cl, Br, I). It encompasses e.g. —$OCH_2Cl$, —$OCH_2F$, —$OCHCl_2$, —$OCHF_2$, —$OCCl_3$, —$OCF_3$ and —$OCH_2$—$CHCl_2$. Preferably haloalkoxy is understood in the context of this invention as halogen-substituted —$OC_{1-4}$-alkyl representing halogen substituted C1-, C2-, C3- or C4-alkoxy. The halogen-substituted alkyl radicals are thus preferably O-methyl, O-ethyl, O-propyl, and O-butyl. Preferred examples include —$OCH_2Cl$, —$OCH_2F$, —$OCHCl_2$, —$OCHF_2$, and —$OCF_3$.

Most preferably in connection with alkyl (also in alkylaryl, alkylheterocyclyl or alkylcycloalkyl), alkenyl, alkynyl or O-alkyl, substituted is understood in the context of this invention that any alkyl (also in alkylaryl, alkylheterocyclyl or alkylcycloalkyl), alkenyl, alkynyl or O-alkyl which is substituted is substituted with one or more of halogen (F, Cl, Br, I), —$OR_c$, —CN, haloalkyl, haloalkoxy or —$OC_{1-4}$alkyl being unsubstituted or substituted by one or more of —$OR_c$ or halogen (F, Cl, I, Br), being $R_c$ one of $R_9$ or $R_{10}$, (being $R_{c'}$ one of $R_{9'}$ or $R_{10'}$; being $R_{c''}$ one of $R_{9''}$ or $R_{10''}$; being $R_{c'''}$ one of $R_{9'''}$ or $R_{10'''}$), wherein $R_1$ to $R_{11'''}$ and $R_y$ and $R_w$, are as defined in the description, and wherein when different radicals $R_1$ to $R_{11'''}$ and $R_y$ and $R_w$, are present simultaneously in Formula I they may be identical or different.

Aryl is understood as meaning ring systems with at least one aromatic ring but without heteroatoms even in only one of the rings. Examples are phenyl, naphthyl, fluoranthenyl, fluorenyl, tetralinyl or indanyl, in particular 9H-fluorenyl or anthracenyl radicals, which can be unsubstituted or once or several times substituted. Most preferably aryl is understood in the context of this invention as phenyl, naphtyl or anthracenyl, preferably is phenyl.

In the context of this invention alkylaryl is understood as meaning an aryl group (see above) being connected to another atom through 1 to 4 (—$CH_2$—) groups. Most preferably alkylaryl is benzyl (i.e. —$CH_2$-phenyl).

In the context of this invention alkylaryl is understood as meaning an aryl group (see above) being connected to another atom through a $C_{1-6}$-alkyl (see above) which may be branched or linear and is unsubstituted or substituted once or several times. Preferably alkylaryl is understood as meaning an aryl group (see above) being connected to another atom through 1 to 4 (—$CH_2$—) groups. Most preferably alkylaryl is benzyl (i.e. —$CH_2$-phenyl).

In the context of this invention alkylheterocyclyl is understood as meaning an heterocyclyl group being connected to another atom through a $C_{1-6}$-alkyl (see above) which may be branched or linear and is unsubstituted or substituted once or several times. Preferably alkylheterocyclyl is understood as meaning an heterocyclyl group (see above) being connected to another atom through 1 to 4 (—$CH_2$—) groups. Most preferably alkylheterocyclyl is —$CH_2$-pyridine.

In the context of this invention alkylcycloalkyl is understood as meaning an cycloalkyl group being connected to another atom through a $C_{1-6}$-alkyl (see above) which may be branched or linear and is unsubstituted or substituted once or several times. Preferably alkylcycloalkyl is understood as meaning an cycloalkyl group (see above) being connected to another atom through 1 to 4 (—$CH_2$—) groups. Most preferably alkylcycloalkyl is —$CH_2$-cyclopropyl.

A heterocyclyl radical or group (also called heterocyclyl hereinafter) is understood as meaning heterocyclic ring systems, with at least one saturated or unsaturated ring which contains one or more heteroatoms from the group consisting of nitrogen, oxygen and/or sulfur in the ring. A heterocyclic group can also be substituted once or several times.

Examples include non-aromatic heterocyclyls such as tetrahydropyrane, oxazepane, morpholine, piperidine, pyrrolidine as well as heteroaryls such as furan, benzofuran, thiophene, benzothiophene, pyrrole, pyridine, pyrimidine, pyrazine, quinoline, isoquinoline, phthalazine, thiazole, benzothiazole, indole, benzotriazole, carbazole and quinazoline.

Subgroups inside the heterocyclyls as understood herein include heteroaryls and non-aromatic heterocyclyls.
  the heteroaryl (being equivalent to heteroaromatic radicals or aromatic heterocyclyls) is an aromatic heterocyclic ring system of one or more rings of which at least one aromatic ring contains one or more heteroatoms from the group consisting of nitrogen, oxygen and/or sulfur in the ring; preferably is an aromatic heterocyclic ring system of one or two rings of which at least one aromatic ring contains one or more heteroatoms from the group consisting of nitrogen, oxygen and/or sulfur in the ring, more preferably is selected from furan, benzofuran, thiophene, benzothiophene, pyrrole, pyridine, pyrimidine, pyrazine, quinoline, isoquinoline, phthalazine, benzothiazole, indole, benzotriazole, carbazole, quinazoline, thiazole, imidazole, pyrazole, oxazole, thiophene and benzimidazole;

the non-aromatic heterocyclyl is a heterocyclic ring system of one or more rings of which at least one ring—with this (or these) ring(s) then not being aromatic—contains one or more heteroatoms from the group consisting of nitrogen, oxygen and/or sulfur in the ring; preferably is a heterocyclic ring system of one or two rings of which one or both rings—with this one or two rings then not being aromatic—contain/s one or more heteroatoms from the group consisting of nitrogen, oxygen and/or sulfur in the ring, more preferably is selected from oxazepam, pyrrolidine, piperidine, piperazine, tetrahydropyran, morpholine, indoline, oxopyrrolidine, benzodioxane, especially is benzodioxane, morpholine, tetrahydropyran, piperidine, oxopyrrolidine, and pyrrolidine.

Preferably in the context of this invention heterocyclyl is defined as a heterocyclic ring system of one or more saturated or unsaturated rings of which at least one ring contains one or more heteroatoms from the group consisting of nitrogen, oxygen and/or sulfur in the ring. Preferably it is a heterocyclic ring system of one or two saturated or unsaturated rings of which at least one ring contains one or more heteroatoms from the group consisting of nitrogen, oxygen and/or sulfur in the ring.

Preferred examples of heterocyclyls include oxazepan, pyrrolidine, imidazole, oxadiazole, tetrazole, pyridine, pyrimidine, piperidine, piperazine, benzofuran, benzimidazole, indazole, benzodiazole, thiazole, benzothiazole, tetrahydropyrane, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole oxopyrrolidine, pyrimidine, benzodioxolane, benzodioxane, carbazole and quinazoline, especially is pyridine, pyrazine, indazole, benzodioxane, thiazole, benzothiazole, morpholine, tetrahydropyrane, pyrazole, imidazole, piperidine, thiophene, indole, benzimidazole, pyrrolo[2,3b]pyridine, benzoxazole, oxopyrrolidine, pyrimidine, oxazepane and pyrrolidine.

In the context of this invention oxopyrrolidine is understood as meaning pyrrolidin-2-one.

In connection with aromatic heterocyclyls (heteroaryls), non-aromatic heterocyclyls, aryls and cycloalkyls, when a ring system falls within two or more of the above cycle definitions simultaneously, then the ring system is defined first as an aromatic heterocyclyl (heteroaryl) if at least one aromatic ring contains a heteroatom. If no aromatic ring contains a heteroatom, then the ring system is defined as a non-aromatic heterocyclyl if at least one non-aromatic ring contains a heteroatom. If no non-aromatic ring contains a heteroatom, then the ring system is defined as an aryl if it contains at least one aryl cycle. If no aryl is present, then the ring system is defined as a cycloalkyl if at least one non-aromatic cyclic hydrocarbon is present.

Preferably, the aryl is a monocyclic aryl.
Preferably, the heteroaryl is a monocyclic heteroaryl.
Preferably, the non-aromatic heterocyclyl is a monocyclic non-aromatic heterocyclyl.
Preferably, the cycloalkyl is a monocyclic cycloalkyl.
In connection with aryl (including alkyl-aryl), cycloalkyl (including alkyl-cycloalkyl), or heterocyclyl (including alkyl-heterocyclyl), substituted is understood—unless defined otherwise—as meaning substitution of the ring-system of the aryl or alkyl-aryl, cycloalkyl or alkyl-cycloalkyl; heterocyclyl or alkyl-heterocyclyl with one or more of halogen (F, Cl, Br, I), —$R_c$, —$OR_c$, —CN, —$NO_2$, —$NR_cR_{c'''}$, —$C(O)OR_c$, $NR_cC(O)R_{c'}$, —$C(O)NR_cR_{c'}$, —$NR_cS(O)_2R_{c'}$, =O, —$OCH_2CH_2OH$, —$NR_cC(O)NR_{c'}R_{c'''}$, —$S(O)_2NR_cR_{c'}$, —$NR_cS(O)_2NR_{c'}R_{c'''}$, —$N(S(O)_2R_c)(S(O)_2R_{c'})$, haloalkyl, haloalkoxy, —$SR_c$, —$S(O)R_c$, $S(O)_2R_c$ or $C(CH_3)OR_c$; $NR_cR_{c'''}$, with $R_c$ and $R_{c'''}$ independently being either H or a saturated or unsaturated, linear or branched, substituted or unsubstituted $C_{1-6}$-alkyl; a saturated or unsaturated, linear or branched, substituted or unsubstituted $C_{1-6}$-alkyl; a saturated or unsaturated, linear or branched, substituted or unsubstituted —O—$C_{1-6}$-alkyl (alkoxy); a saturated or unsaturated, linear or branched, substituted or unsubstituted —S—$C_{1-6}$-alkyl; a saturated or unsaturated, linear or branched, substituted or unsubstituted —C(O)—$C_{1-6}$-alkyl-group; a saturated or unsaturated, linear or branched, substituted or unsubstituted —C(O)—O—$C_{1-6}$-alkyl-group; a substituted or unsubstituted aryl or alkyl-aryl; a substituted or unsubstituted cycloalkyl or alkyl-cycloalkyl; a substituted or unsubstituted heterocyclyl or alkyl-heterocyclyl, being $R_c$ one of $R_8$, $R_9$ or $R_{11}$, (being $R_{c'}$ one of $R_{8'}$, $R_{9'}$ or $R_{11'}$; being $R_{c''}$ one of $R_{8''}$, $R_{9''}$ or $R_{11''}$; being $R_{c'''}$ one of $R_{8'''}$, $R_{9'''}$ or $R_{11'''}$), wherein $R_1$ to $R_{11'''}$ and $R_y$ and $R_w$, are as defined in the description, and wherein when different radicals $R_1$ to $R_{11'''}$ and $R_y$ and $R_w$, are present simultaneously in Formula I they may be identical or different.

Most preferably in connection with aryl (including alkyl-aryl), cycloalkyl (including alkyl-cycloalkyl), or heterocyclyl (including alkyl-heterocyclyl), substituted is understood in the context of this invention that any aryl, cycloalkyl and heterocyclyl which is substituted is substituted (also in an alyklaryl, alkylcycloalkyl or alkylheterocyclyl) with one or more of halogen (F, Cl, Br, I), —$R_c$, —$OR_c$, —CN, —$NO_2$, —$NR_cR_{c'''}$, $NR_cC(O)R_{c'}$, —$N(S(O)_2R_c)(S(O)_2R_{c'})$, —$NR_cS(O)_2R_{c'}$, =O, haloalkyl, haloalkoxy, or $C(CH_3)OR_c$; —$OC_{1-4}$alkyl being unsubstituted or substituted by one or more of $OR_c$ or halogen (F, Cl, I, Br), —CN, or —$C_{1-4}$alkyl being unsubstituted or substituted by one or more of $OR_c$ or halogen (F, Cl, I, Br), being $R_c$ one of $R_8$, $R_9$ or $R_{11}$, (being $R_{c'}$ one of $R_{8'}$, $R_{9'}$ or $R_{11'}$; being $R_{c''}$ one of $R_{8''}$, $R_{9''}$ or $R_{11''}$; being $R_{c'''}$ one of $R_{8'''}$, $R_{9'''}$ or $R_{11'''}$), wherein $R_1$ to $R_{11'''}$ and $R_y$ and $R_w$, are as defined in the description, and wherein when different radicals $R_1$ to $R_{11'''}$ and $R_y$ and $R_w$, are present simultaneously in Formula I they may be identical or different.

Additionally to the above-mentioned substitutions, in connection with cycloalkyl (including alkyl-cycloalkyl), or heterocycly (including alkylheterocyclyl) namely non-aromatic heterocyclyl (including non-aromatic alkyl-heterocyclyl), substituted is also understood—unless defined otherwise—as meaning substitution of the ring-system of the cycloalkyl or alkyl-cycloalkyl; non-aromatic heterocyclyl or non aromatic alkyl-heterocyclyl with

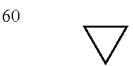

or =O.

The term "leaving group" means a molecular fragment that departs with a pair of electrons in heterolytic bond cleavage. Leaving groups can be anions or neutral molecules. Common anionic leaving groups are halides such as Cl—, Br—, and I—, and sulfonate esters, such as tosylate (TsO—) or mesylate.

The compounds of the invention may be present in crystalline form or in the form of free compounds like a free base or acid.

The term "salt" is to be understood as meaning any form of the active compound used according to the invention in which it assumes an ionic form or is charged and is coupled with a counter-ion (a cation or anion) or is in solution. By this are also to be understood complexes of the active compound with other molecules and ions, in particular complexes via ionic interactions.

The term "physiologically acceptable salt" means in the context of this invention any salt that is physiologically tolerated (most of the time meaning not being toxic-especially not caused by the counter-ion) if used appropriately for a treatment especially if used on or applied to humans and/or mammals.

These physiologically acceptable salts can be formed with cations or bases and in the context of this invention is understood as meaning salts of at least one of the compounds used according to the invention—usually a (deprotonated) acid—as an anion with at least one, preferably inorganic, cation which is physiologically tolerated—especially if used on humans and/or mammals. The salts of the alkali metals and alkaline earth metals are particularly preferred, and also those with $NH_4$, but in particular (mono)- or (di)sodium, (mono)- or (di)potassium, magnesium or calcium salts.

Physiologically acceptable salts can also be formed with anions or acids and in the context of this invention is understood as meaning salts of at least one of the compounds used according to the invention as the cation with at least one anion which are physiologically tolerated—especially if used on humans and/or mammals. By this is understood in particular, in the context of this invention, the salt formed with a physiologically tolerated acid, that is to say salts of the particular active compound with inorganic or organic acids which are physiologically tolerated—especially if used on humans and/or mammals. Examples of physiologically tolerated salts of particular acids are salts of: hydrochloric acid, hydrobromic acid, sulfuric acid, methanesulfonic acid, formic acid, acetic acid, oxalic acid, succinic acid, malic acid, tartaric acid, mandelic acid, fumaric acid, lactic acid or citric acid.

Any compound that is a solvate of a compound according to the invention like a compound according to general formula I defined above is understood to be also covered by the scope of the invention. Methods of solvation are generally known within the art. Suitable solvates are pharmaceutically acceptable solvates. The term "solvate" according to this invention is to be understood as meaning any form of the active compound according to the invention in which this compound has attached to it via non-covalent binding another molecule (most likely a polar solvent). Especially preferred examples include hydrates and alcoholates, like methanolates or ethanolates.

Any compound that is a prodrug of a compound according to the invention like a compound according to general formula I defined above is understood to be also covered by the scope of the invention. The term "prodrug" is used in its broadest sense and encompasses those derivatives that are converted in vivo to the compounds of the invention. Such derivatives would readily occur to those skilled in the art, and include, depending on the functional groups present in the molecule and without limitation, the following derivatives of the present compounds: esters, amino acid esters, phosphate esters, metal salts sulfonate esters, carbamates, and amides. Examples of well known methods of producing a prodrug of a given acting compound are known to those skilled in the art and can be found e.g. in Krogsgaard-Larsen et al. "Textbook of Drug design and Discovery" Taylor & Francis (April 2002).

Unless otherwise stated, the compounds of the invention are also meant to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon or of a nitrogen by $^{15}N$-enriched nitrogen are within the scope of this invention.

The compounds of formula (I) as well as their salts or solvates of the compounds are preferably in pharmaceutically acceptable or substantially pure form. By pharmaceutically acceptable form is meant, inter alia, having a pharmaceutically acceptable level of purity excluding normal pharmaceutical additives such as diluents and carriers, and including no material considered toxic at normal dosage levels. Purity levels for the drug substance are preferably above 50%, more preferably above 70%, most preferably above 90%. In a preferred embodiment it is above 95% of the compound of formula (I), or of its salts. This applies also to its solvates or prodrugs.

In a further embodiment the compound according to the invention of general formula I is a compound wherein n is 1, 2, 3, 4, 5 or 6;

Y—W is $CR_y$—N or N—$CR_w$;

X is a bond or —$CR_6R_{6'}$—;

$R_1$ is substituted or unsubstituted cycloalkyl, substituted or unsubstituted aryl, or substituted or unsubstituted heterocyclyl;

wherein said cycloalkyl, aryl or heterocyclyl in $R_1$, if substituted, being substituted with one or more substituents selected from halogen, —$R_8$, —$OR_8$, —$NO_2$, —$NR_8R_{8'''}$, $NR_8C(O)R_{8'}$, —$NR_8S(O)_2R_{8'}$, —$S(O)_2NR_8R_{8'}$, —$NR_8C(O)NR_8R_{8''}$, —$SR_8$, —$S(O)R_8$, —$S(O)_2R_8$, —CN, haloalkyl, haloalkoxy, —$C(O)OR_8$, —$C(O)NR_8R_{8'}$, —$OCH_2CH_2OH$, —$NR_8S(O)_2NR_8R_{8''}$ and $C(CH_3)_2OR_8$;

wherein $R_8$, $R_{8'}$, and $R_{8''}$ are independently selected from hydrogen, unsubstituted $C_{1-6}$ alkyl, unsubstituted $C_{2-6}$ alkenyl, unsubstituted $C_{2-6}$ alkynyl, unsubstituted aryl or unsubstituted alkylaryl, unsubstituted cycloalkyl or unsubstituted alkylcycloalkyl, unsubstituted heterocyclyl and unsubstituted alkyheterocylcyl;

and wherein $R_{8'''}$, is selected from hydrogen, unsubstituted $C_{1-6}$ alkyl, unsubstituted $C_{2-6}$ alkenyl, unsubstituted $C_{2-6}$ alkynyl and -Boc;

$R_2$ is substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl or substituted or unsubstituted heterocyclyl;

wherein said cycloalkyl, aryl or heterocyclyl in $R_2$, if substituted, is substituted with one or more substituents selected from halogen, —$R_9$, —$OR_9$, —$NO_2$, —$NR_9R_{9'''}$, $NR_9C(O)R_{9'}$, —$NR_9S(O)_2R_{9'}$, —$N(S(O)_2R_9)(S(O)_2R_{9'})$, —$S(O)_2NR_9R_{9'}$, —$NR_9C(O)NR_{9'}$ $R_{9''}$, —$SR_9$, —$S(O)R_9$, $S(O)_2R_9$, —CN, haloalkyl, haloalkoxy, —$C(O)OR_9$, —$C(O)NR_9R_{9'}$, —$OCH_2CH_2OH$, —$NR_9S(O)_2NR_9R_{9''}$ and $C(CH_3)_2OR_9$;

wherein the alkyl, alkylene or alkynyl in $R_2$, if substituted, is substituted with one or more substituents selected from —$OR_9$, halogen, —CN, haloalkyl, haloalkoxy, —$NR_9R_{9'''}$, —$SR_9$, —$S(O)R_9$, and —$S(O)_2R_9$;
wherein $R_9$, $R_{9'}$ and $R_{9''}$ are independently selected from hydrogen, unsubstituted $C_{1-6}$ alkyl unsubstituted $C_{2-6}$ alkenyl, and unsubstituted $C_{2-6}$ alkynyl;
and wherein $R_{9'''}$ is selected from hydrogen, unsubstituted $C_{1-6}$ alkyl, unsubstituted $C_{2-6}$ alkenyl, unsubstituted $C_{2-6}$ alkynyl and -Boc;

$R_3$ is hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl, substituted or unsubstituted heterocyclyl, substituted or unsubstituted alkylcycloalkyl, substituted or unsubstituted alkylaryl, or substituted or unsubstituted alkylheterocyclyl;

$R_4$, $R_{4'}$, $R_{4''}$ and $R_{4'''}$ are independently selected from hydrogen or unsubstituted $C_{1-6}$ alkyl, unsubstituted $C_{2-6}$ alkenyl, and unsubstituted $C_{2-6}$ alkynyl;

$R_5$, and $R_{5'}$ are independently selected from hydrogen or unsubstituted $C_{1-6}$ alkyl, unsubstituted $C_{2-6}$ alkenyl, and unsubstituted $C_{2-6}$ alkynyl;

$R_6$ is selected from hydrogen, halogen, —$OR_7$, substituted or unsubstituted $C_{1-6}$ alkyl, substituted or unsubstituted $C_{2-6}$ alkenyl, substituted or unsubstituted $C_{2-6}$ alkynyl, —$C(O)OR_7$, —$C(O)NR_7R_{7'}$, —$NR_7C(O)R_{7'}$, and —$NR_7R_{7'''}$;

$R_{6''}$ is selected from hydrogen, substituted or unsubstituted $C_{1-6}$ alkyl, substituted or unsubstituted $C_{2-6}$ alkenyl and substituted or unsubstituted $C_{2-6}$ alkynyl;
wherein $R_7$, $R_{7'}$ and $R_{7''}$ are independently selected from hydrogen, unsubstituted $C_{1-6}$ alkyl, unsubstituted $C_{2-6}$ alkenyl, unsubstituted $C_{2-6}$ alkynyl, and unsubstituted acetyl;
and $R_{7'''}$ is selected from hydrogen, unsubstituted $C_{1-6}$ alkyl, unsubstituted $C_{2-6}$ alkenyl, unsubstituted $C_{2-6}$ alkynyl and -Boc;

$R_y$ is selected from hydrogen, substituted or unsubstituted $C_{1-6}$ alkyl, substituted or unsubstituted $C_{2-6}$ alkenyl, and substituted or unsubstituted $C_{2-6}$ alkynyl;

$R_w$ is selected from hydrogen, substituted or unsubstituted $C_{1-6}$ alkyl, substituted or unsubstituted $C_{2-6}$ alkenyl, and substituted or unsubstituted $C_{2-6}$ alkynyl;
and/or
wherein the alkyl, alkylene or alkynyl, other than those defined in $R_1$ or $R_2$, if substituted, is substituted with one or more substituents selected from —$OR_{10}$, halogen, —CN, haloalkyl, haloalkoxy, —$NR_{10}R_{10'''}$, —$SR_{10}$, —$S(O)R_{10}$, and —$S(O)_2R_{10}$;
wherein $R_{10}$, $R_{10'}$ and $R_{10''}$ are independently selected from hydrogen, unsubstituted $C_{1-6}$ alkyl, unsubstituted $C_{2-6}$ alkenyl, and unsubstituted $C_{2-6}$ alkynyl;
and wherein $R_{10'''}$ is selected from hydrogen, unsubstituted $C_{1-6}$ alkyl, unsubstituted $C_{2-6}$ alkenyl, unsubstituted $C_{2-6}$ alkynyl and -Boc;
and/or
wherein the aryl, heterocyclyl or cycloalkyl, also in alkylaryl, alkylcycloalkyl and alkylheterocyclyl, other than those defined in $R_1$ or $R_2$, if substituted, is substituted with one or more substituents selected from halogen, —$R_{11}$, —$OR_{11}$, —$NO_2$, —$NR_{11}R_{11'''}$, $NR_{11}C(O)R_{11'}$, —$NR_{11}S(O)_2R_{11'}$, —$S(O)_2NR_{11}R_{11'}$, —$NR_{11}C(O)NR_{11'}R_{11'''}$, —$SR_{11}$, —$S(O)R_{11}$, $S(O)_2R11$, —CN, haloalkyl, haloalkoxy, —$C(O)OR_{11}$, —$C(O)NR_{11}R_{11'}$, —$OCH_2CH_2OH$, —$NR_{11}S(O)_2NR_{11'}R_{11''}$ and $C(CH_3)_2OR_{11}$;
wherein $R_{11}$, $R_{11'}$ and $R_{11''}$ are independently selected from hydrogen, unsubstituted $C_{1-6}$ alkyl, unsubstituted $C_{2-6}$ alkenyl, unsubstituted $C_{2-6}$ alkynyl, unsubstituted aryl, unsubstituted alkylaryl, unsubstituted cycloalkyl and unsubstituted alkylcycloalkyl, unsubstituted heterocyclyl and unsubstituted alkyheterocylcyl;
and wherein $R_{11'''}$ is selected from hydrogen, unsubstituted $C_{1-6}$ alkyl, unsubstituted $C_{2-6}$ alkenyl, unsubstituted $C_{2-6}$ alkynyl and -Boc;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general formula I is a compound wherein
n is 1, 2, 3, 4, 5 or 6;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general formula I is a compound wherein
Y—W is $CR_y$—N or N—$CR_w$;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general formula I is a compound wherein
X is a bond or —$CR_6R_{6'}$—;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general formula I is a compound wherein
$R_1$ is substituted or unsubstituted cycloalkyl, substituted or unsubstituted aryl, or substituted or unsubstituted heterocyclyl;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general formula I is a compound wherein
$R_1$ is substituted or unsubstituted aryl or substituted or unsubstituted heterocyclyl;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general formula I is a compound wherein
$R_2$ is substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl or substituted or unsubstituted heterocyclyl, preferably $R_2$ is substituted or unsubstituted $C_{1-6}$ alkyl, substituted or unsubstituted cycloalkyl, substituted or unsubstituted aryl or substituted or unsubstituted heterocyclyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general formula I is a compound wherein $R_2$ is substituted or unsubstituted aryl or substituted or unsubstituted heterocyclyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general formula I is a compound wherein $R_3$ is hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl, substituted or unsubstituted heterocyclyl, substituted or unsubstituted alkylcycloalkyl, substituted or unsubstituted alkylaryl, or substituted or unsubstituted alkylheterocyclyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general formula I is a compound wherein $R_3$ is hydrogen, substituted or unsubstituted $C_{1-6}$ alkyl, substituted or unsubstituted $C_{2-6}$ alkenyl, or substituted or unsubstituted $C_{2-6}$ alkynyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general formula I is a compound wherein $R_3$ is hydrogen or substituted or unsubstituted $C_{1-6}$ alkyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general formula I is a compound wherein $R_4$, $R_{4'}$, $R_{4''}$ and $R_{4'''}$ are independently selected from hydrogen or unsubstituted $C_{1-6}$ alkyl, unsubstituted $C_{2-6}$ alkenyl, and unsubstituted $C_{2-6}$ alkynyl, preferably $R_4$, $R_{4'}$, $R_{4''}$, and $R_{4'''}$ are independently selected from hydrogen and unsubstituted $C_{1-6}$ alkyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general formula I is a compound wherein $R_{5'}$ and $R_{5'}$ are independently selected from hydrogen or unsubstituted $C_{1-6}$ alkyl, unsubstituted $C_{2-6}$ alkenyl, and unsubstituted $C_{2-6}$ alkynyl, preferably $R_{5'}$ and $R_{5'}$ are independently selected from hydrogen and unsubstituted $C_{1-6}$ alkyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general formula I is a compound wherein $R_6$ is selected from hydrogen, halogen, —$OR_7$, substituted or unsubstituted $C_{1-6}$ alkyl, substituted or unsubstituted $C_{2-6}$ alkenyl, substituted or unsubstituted $C_{2-6}$ alkynyl, —C(O)$OR_7$, —C(O)$NR_7R_{7'}$, —$NR_7C(O)R_{7'}$, and —$NR_7R_{7''}$;

$R_{6''}$ is selected from hydrogen, substituted or unsubstituted $C_{1-6}$ alkyl, substituted or unsubstituted $C_{2-6}$ alkenyl and substituted or unsubstituted $C_{2-6}$ alkynyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general formula I is a compound wherein $R_6$ is selected from hydrogen, halogen, —$OR_7$, substituted or unsubstituted $C_{1-6}$ alkyl, substituted or unsubstituted $C_{2-6}$ alkenyl, substituted or unsubstituted $C_{2-6}$ alkynyl, —C(O)$OR_7$, —C(O)$NR_7R_{7'}$, —$NR_7C(O)R_{7'}$, and —$NR_7R_{7''}$, preferably $R_6$ is selected from hydrogen, halogen, —$OR_7$, substituted or unsubstituted $C_{1-6}$ alkyl, —C(O)$OR_7$, —C(O)$NR_7R_{7'}$, —$NR_7C(O)R_{7'}$, and —$NR_7R_{7''}$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general formula I is a compound wherein $R_6$ is selected from hydrogen and —$OR_7$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general formula I is a compound wherein $R_{6'}$ is selected from hydrogen, substituted or unsubstituted $C_{1-6}$ alkyl, substituted or unsubstituted $C_{2-6}$ alkenyl and substituted or unsubstituted $C_{2-6}$ alkynyl, preferably $R_{6'}$ is selected from hydrogen and substituted or unsubstituted $C_{1-6}$ alkyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general formula I is a compound wherein $R_6$ and $R_{6'}$, taken together with the carbon atom to which they are attached, may form a C=O group;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general formula I is a compound wherein $R_7$, $R_{7'}$ and $R_{7''}$ are independently selected from hydrogen, unsubstituted $C_{1-6}$ alkyl, unsubstituted $C_{2-6}$ alkenyl, unsubstituted $C_{2-6}$ alkynyl, and unsubstituted acetyl;

and $R_{7'''}$ is selected from hydrogen, unsubstituted $C_{1-6}$ alkyl, unsubstituted $C_{2-6}$ alkenyl, unsubstituted $C_{2-6}$ alkynyl and -Boc;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general formula I is a compound wherein $R_7$, $R_{7'}$ and $R_{7''}$ are independently selected from hydrogen, unsubstituted $C_{1-6}$ alkyl, unsubstituted $C_{2-6}$ alkenyl, unsubstituted $C_{2-6}$ alkynyl and unsubstituted acetyl, preferably $R_7$, $R_{7'}$ and $R_{7''}$ are independently selected from hydrogen, unsubstituted $C_{1-6}$ alkyl and unsubstituted acetyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general formula I is a compound wherein $R_{7'''}$ is selected from hydrogen, unsubstituted $C_{1-6}$ alkyl, unsubstituted $C_{2-6}$ alkenyl, unsubstituted $C_{2-6}$ alkynyl and -Boc, preferably $R_{7'''}$ is selected from hydrogen, unsubstituted $C_{1-6}$ alkyl and -Boc;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general formula I is a compound wherein $R_8$, $R_{8'}$ and $R_{8''}$ are independently selected from hydrogen, unsubstituted $C_{1-6}$ alkyl, unsubstituted $C_{2-6}$ alkenyl, unsubstituted $C_{2-6}$ alkynyl, unsubstituted aryl or unsubstituted alkylaryl, unsubstituted cycloalkyl or unsubstituted alkylcycloalkyl, unsubstituted heterocyclyl and unsubstituted alkyheterocylcyl;

and wherein $R_{8'''}$ is selected from hydrogen, unsubstituted $C_{1-6}$ alkyl, unsubstituted $C_{2-6}$ alkenyl, unsubstituted $C_{2-6}$ alkynyl and -Boc;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general formula I is a compound wherein $R_8$, $R_{8'}$ and $R_{8''}$ are independently selected from hydrogen, unsubstituted $C_{1-6}$ alkyl, unsubstituted $C_{2-6}$ alkenyl, unsubstituted $C_{2-6}$ alkynyl, unsubstituted aryl or unsubstituted alkylaryl, unsubstituted cycloalkyl or unsubstituted alkylcycloalkyl, unsubstituted heterocyclyl and unsubstituted alkyheterocylcyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general formula I is a compound wherein $R_8$, $R_{8'}$ and $R_{8''}$ are independently selected from hydrogen, unsubstituted $C_{1-6}$ alkyl, unsubstituted $C_{2-6}$ alkenyl and unsubstituted $C_{2-6}$ alkynyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general formula I is a compound wherein $R_8$, $R_{8'}$ and $R_{8''}$ are independently selected from hydrogen and unsubstituted $C_{1-6}$ alkyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general formula I is a compound wherein $R_{8'''}$ is selected from hydrogen, unsubstituted $C_{1-6}$ alkyl, unsubstituted $C_{2-6}$ alkenyl, unsubstituted $C_{2-6}$ alkynyl and -Boc, preferably $R_{8'''}$ is selected from hydrogen, unsubstituted $C_{1-6}$ alkyl and -Boc;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general formula I is a compound wherein $R_9$, $R_{9'}$ and $R_{9''}$ are independently selected from hydrogen, unsubstituted $C_{1-6}$ alkyl, unsubstituted $C_{2-6}$ alkenyl, and unsubstituted $C_{2-6}$ alkynyl;

and wherein $R_{9'''}$ is selected from hydrogen, unsubstituted $C_{1-6}$ alkyl, unsubstituted $C_{2-6}$ alkenyl, unsubstituted $C_{2-6}$ alkynyl and -Boc;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general formula I is a compound wherein $R_9$, $R_{9'}$ and $R_{9''}$ are independently selected from hydrogen, unsubstituted $C_{1-6}$ alkyl, unsubstituted $C_{2-6}$ alkenyl and unsubstituted $C_{2-6}$ alkynyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general formula I is a compound wherein $R_9$, $R_{9'}$ and $R_{9''}$ are independently selected from hydrogen and unsubstituted $C_{1-6}$ alkyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general formula I is a compound wherein $R_{9'''}$ is selected from hydrogen, unsubstituted $C_{1-6}$ alkyl, unsubstituted $C_{2-6}$ alkenyl, unsubstituted $C_{2-6}$ alkynyl and -Boc, preferably $R_{9'''}$ is selected from hydrogen, unsubstituted $C_{1-6}$ alkyl and -Boc;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general formula I is a compound wherein $R_{10}$, $R_{10'}$ and $R_{10''}$ are independently selected from hydrogen, unsubstituted $C_{1-6}$ alkyl, unsubstituted $C_{2-6}$ alkenyl, and unsubstituted $C_{2-6}$ alkynyl;

and wherein $R_{10'''}$ is selected from hydrogen, unsubstituted $C_{1-6}$ alkyl, unsubstituted $C_{2-6}$ alkenyl, unsubstituted $C_{2-6}$ alkynyl and -Boc;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general formula I is a compound wherein $R_{10}$, $R_{10'}$ and $R_{10''}$ are independently selected from hydrogen, unsubstituted $C_{1-6}$ alkyl, unsubstituted $C_{2-6}$ alkenyl, and unsubstituted $C_{2-6}$ alkynyl, preferably $R_{10}$, $R_{10'}$ and $R_{11''}$ are independently selected from hydrogen and unsubstituted $C_{1-6}$ alkyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general formula I is a compound wherein $R_{10'''}$ is selected from hydrogen, unsubstituted $C_{1-6}$ alkyl, unsubstituted $C_{2-6}$ alkenyl, unsubstituted $C_{2-6}$ alkynyl and -Boc, preferably $R_{10'''}$ is selected from hydrogen, unsubstituted $C_{1-6}$ alkyl and -Boc;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general formula I is a compound wherein $R_{11}$, $R_{11'}$ and $R_{11''}$ are independently selected from hydrogen, unsubstituted $C_{1-6}$ alkyl, unsubstituted $C_{2-6}$ alkenyl, unsubstituted $C_{2-6}$ alkynyl, unsubstituted aryl, unsubstituted alkylaryl, unsubstituted cycloalkyl and unsubstituted alkylcycloalkyl, unsubstituted heterocyclyl and unsubstituted alkyheterocylcyl;

and wherein $R_{11'''}$ is selected from hydrogen, unsubstituted $C_{1-6}$ alkyl, unsubstituted $C_{2-6}$ alkenyl, unsubstituted $C_{2-6}$ alkynyl and -Boc;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general formula I is a compound wherein $R_{11}$, $R_{11'}$ and $R_{11''}$ are independently selected from hydrogen, unsubstituted $C_{1-6}$ alkyl, unsubstituted $C_{2-6}$ alkenyl, unsubstituted $C_{2-6}$ alkynyl, unsubstituted aryl, unsubstituted alkylaryl, unsubstituted cycloalkyl and unsubstituted alkylcycloalkyl, unsubstituted heterocyclyl and unsubstituted alkyheterocylcyl, preferably $R_{11}$, $R_{11'}$ and $R_{11''}$ are independently selected from hydrogen, unsubstituted $C_{1-6}$ alkyl, unsubstituted aryl, unsubstituted alkylaryl, unsubstituted cycloalkyl and unsubstituted alkylcycloalkyl, unsubstituted heterocyclyl and unsubstituted alkyheterocylcyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general formula I is a compound wherein $R_{11'''}$ is selected from hydrogen, unsubstituted $C_{1-6}$ alkyl, unsubstituted $C_{2-6}$ alkenyl, unsubstituted $C_{2-6}$ alkynyl and -Boc, preferably $R_{11'''}$ is selected from hydrogen, unsubstituted $C_{1-6}$ alkyl and -Boc;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general formula I is a compound wherein $R_y$ is selected from hydrogen, substituted or unsubstituted $C_{1-6}$ alkyl, substituted or unsubstituted $C_{2-6}$ alkenyl, and substituted or unsubstituted $C_{2-6}$ alkynyl, preferably $R_y$ is selected from hydrogen and substituted or unsubstituted $C_{1-6}$ alkyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general formula I is a compound wherein $R_w$ is selected from hydrogen, substituted or unsubstituted $C_{1-6}$ alkyl, substituted or unsubstituted $C_{2-6}$ alkenyl, and substituted or unsubstituted $C_{2-6}$ alkynyl, preferably $R_w$ is selected from hydrogen and substituted or unsubstituted $C_{1-6}$ alkyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general formula I is a compound wherein X is a bond;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general formula I is a compound wherein X is —$CR_6R_{6'}$—;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general formula I is a compound wherein X is —$CH_2$—;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general formula I is a compound wherein X is —CH(OH)—;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general formula I is a compound wherein Y—W is $CR_y$—N;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general formula I is a compound wherein Y—W is N—$CR_w$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general formula I is a compound wherein n is 1;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general formula I is a compound wherein n is 2;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general formula I is a compound wherein n is 1 or 2, X is a bond and $R_2$ is a substituted or unsubstituted group selected from phenyl, pyridine and thiazole;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general formula I is a compound wherein
n is 1 or 2, X is a bond and $R_1$ is a substituted or unsubstituted group selected from phenyl and pyridine;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general formula I is a compound wherein
n is 1 or 2, X is a bond, $R_1$ is a substituted or unsubstituted group selected from phenyl and pyridine, and $R_2$ is a substituted or unsubstituted group selected from phenyl, pyridine and thiazole;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general formula I is a compound wherein
n is 1 or 2, X is a bond, Y—W is —CH—N—, $R_1$ is a substituted or unsubstituted group selected from phenyl and pyridine, and $R_2$ is a substituted or unsubstituted group selected from phenyl, pyridine and thiazole;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general formula I is a compound wherein
$R_3$ is substituted or unsubstituted alkyl and $R_4$, $R_{4'}$, $R_{4''}$ and $R_{4'''}$ are all hydrogen;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general formula I is a compound wherein
$R_3$ is substituted or unsubstituted methyl and $R_4$, $R_{4'}$, $R_{4''}$ and $R_{4'''}$ are all hydrogen;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general formula I is a compound wherein
$R_3$ is methyl and $R_4$, $R_{4'}$, $R_{4''}$ and $R_{4'''}$ are all hydrogen;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general formula I is a compound wherein
$R_1$ is substituted or unsubstituted cycloalkyl, substituted or unsubstituted aryl, or substituted or unsubstituted heterocyclyl;
wherein
the aryl is selected from phenyl, naphtyl, or anthracene; preferably is napthyl and phenyl; more preferably is phenyl;
and/or
the heterocyclyl is a heterocyclic ring system of one or more saturated or unsaturated rings of which at least one ring contains one or more heteroatoms from the group consisting of nitrogen, oxygen and/or sulfur in the ring; preferably is a heterocyclic ring system of one or two saturated or unsaturated rings of which at least one ring contains one or more heteroatoms from the group consisting of nitrogen, oxygen and/or sulfur in the ring, more preferably is selected from oxazepan, pyrrolidine, imidazole, oxadiazole, tetrazole, pyridine, pyrimidine, piperidine, piperazine, benzofuran, benzimidazole, indazole, benzothiazole, benzodiazole, thiazole, benzothiazole, tetrahydropyrane, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole oxopyrrolidine, pyrimidine, benzodioxolane, benzodioxane, carbazole and quinazoline, more preferably the heterocyclyl is pyridine;
and/or
the cycloalkyl is $C_{3-8}$ cycloalkyl like cyclopropyl, cyclobutyl, cyclopentyl, cyclohexyl, cycloheptyl, or cyclooctyl; preferably is $C_{3-7}$ cycloalkyl like cyclopropyl, cyclobutyl, cyclopentyl, cyclohexyl, or cycloheptyl; more preferably from $C_{3-6}$ cycloalkyl like cyclopropyl, cyclobutyl, cyclopentyl or cyclohexyl:
and/or
$R_2$ is substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl or substituted or unsubstituted heterocyclyl; wherein the $C_{1-6}$ alkyl is preferably selected from methyl, ethyl, propyl, butyl, pentyl, hexyl, isopropyl, or 2-methylpropyl;
and/or
the $C_{2-6}$-alkenyl is preferably selected from ethylene, propylene, butylene, pentylene or hexylene;
and/or
the $C_{2-6}$-alkynyl is preferably selected from ethyne, propyne, butyne, pentyne or hexyne;
and/or
the aryl is selected from phenyl, naphtyl, or anthracene; preferably is napthyl and phenyl; more preferably is phenyl;
and/or
the heterocyclyl is a heterocyclic ring system of one or more saturated or unsaturated rings of which at least one ring contains one or more heteroatoms from the group consisting of nitrogen, oxygen and/or sulfur in the ring; preferably is a heterocyclic ring system of one or two saturated or unsaturated rings of which at least one ring contains one or more heteroatoms from the group consisting of nitrogen, oxygen and/or sulfur in the ring, more preferably is selected from oxazepan, pyrrolidine, imidazole, oxadiazole, tetrazole, pyridine, pyrimidine, piperidine, piperazine, benzofuran, benzimidazole, indazole, benzothiazole, benzodiazole, thiazole, benzothiazole, tetrahydropyrane, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole oxopyrrolidine, pyrimidine, benzodioxolane, benzodioxane, carbazole and quinazoline, more preferably the heterocyclyl is pyridine or thiazole;

and/or the cycloalkyl is $C_{3-8}$ cycloalkyl like cyclopropyl, cyclobutyl, cyclopentyl, cyclohexyl, cycloheptyl, or cyclooctyl; preferably is $C_{3-7}$ cycloalkyl like cyclopropyl, cyclobutyl, cyclopentyl, cyclohexyl, or cycloheptyl; more preferably from $C_{3-6}$ cycloalkyl like cyclopropyl, cyclobutyl, cyclopentyl or cyclohexyl;

and/or $R_3$ is hydrogen, or substituted or unsubstituted $C_{1-6}$ alkyl, substituted or unsubstituted $C_{2-6}$ alkenyl, and substituted or unsubstituted $C_{2-6}$ alkynyl, substituted or unsubstituted cycloalkyl, substituted or unsubstituted aryl, substituted or unsubstituted heterocyclyl, substituted or unsubstituted alkylcycloalkyl, substituted or unsubstituted alkylaryl, or substituted or unsubstituted alkylheterocyclyl;

wherein the alkyl is $C_{1-6}$ alkyl like methyl, ethyl, propyl, butyl, pentyl or hexyl;

and/or the $C_{1-6}$ alkyl is preferably selected from methyl, ethyl, propyl, butyl, pentyl, hexyl, isopropyl, or 2-methylpropyl, preferably the $C_{1-6}$ alkyl is methyl;

and/or the $C_{2-6}$-alkenyl is preferably selected from ethylene, propylene, butylene, pentylene or hexylene;

and/or the $C_{2-6}$-alkynyl is preferably selected from ethyne, propyne, butyne, pentyne or hexyne;

and/or the aryl is selected from phenyl, naphtyl, or anthracene; preferably is napthyl and phenyl; more preferably is phenyl;

and/or the heterocyclyl is a heterocyclic ring system of one or more saturated or unsaturated rings of which at least one ring contains one or more heteroatoms from the group consisting of nitrogen, oxygen and/or sulfur in the ring; preferably is a heterocyclic ring system of one or two saturated or unsaturated rings of which at least one ring contains one or more heteroatoms from the group consisting of nitrogen, oxygen and/or sulfur in the ring, more preferably is selected from oxazepan, pyrrolidine, imidazole, oxadiazole, tetrazole, pyridine, pyrimidine, piperidine, piperazine, benzofuran, benzimidazole, indazole, benzothiazole, benzodiazole, thiazole, benzothiazole, tetrahydropyrane, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole oxopyrrolidine, pyrimidine, benzodioxolane, benzodioxane, carbazole and quinazoline;

and/or the cycloalkyl is $C_{3-8}$ cycloalkyl like cyclopropyl, cyclobutyl, cyclopentyl, cyclohexyl, cycloheptyl, or cyclooctyl; preferably is $C_{3-7}$ cycloalkyl like cyclopropyl, cyclobutyl, cyclopentyl, cyclohexyl, or cycloheptyl; more preferably from $C_{3-6}$ cycloalkyl like cyclopropyl, cyclobutyl, cyclopentyl or cyclohexyl;

and/or $R_4$, $R_{4'}$, $R_{4''}$ and $R_{4'''}$ are independently selected from hydrogen or unsubstituted $C_{1-6}$ alkyl, unsubstituted $C_{2-6}$ alkenyl, and unsubstituted $C_{2-6}$ alkynyl;

wherein the $C_{1-6}$ alkyl is preferably selected from methyl, ethyl, propyl, butyl, pentyl, hexyl, isopropyl, 2-methylpropyl, isopentyl or 3-pentanyl;

and/or the $C_{2-6}$-alkenyl is preferably selected from ethylene, propylene, butylene, pentylene or hexylene;

and/or the $C_{2-6}$-alkynyl is preferably selected from ethyne, propyne, butyne, pentyne or hexyne;

and/or $R_{5'}$ and $R_{5'}$ are independently selected from hydrogen, unsubstituted $C_{1-6}$ alkyl, unsubstituted $C_{2-6}$ alkenyl, and unsubstituted $C_{2-6}$ alkynyl;

wherein the $C_{1-6}$ alkyl is preferably selected from methyl, ethyl, propyl, butyl, pentyl, hexyl, isopropyl, 2-methylpropyl, isopentyl or 3-pentanyl;

and/or the $C_{2-6}$-alkenyl is preferably selected from ethylene, propylene, butylene, pentylene or hexylene;

and/or the $C_{2-6}$-alkynyl is preferably selected from ethyne, propyne, butyne, pentyne or hexyne;

and/or $R_6$ is selected from hydrogen, halogen, —$OR_7$, substituted or unsubstituted $C_{1-6}$ alkyl, substituted or unsubstituted $C_{2-6}$ alkenyl, substituted or unsubstituted $C_{2-6}$ alkynyl, —C(O)$OR_7$, —C(O)$NR_7R_{7'}$, —$NR_7C(O)R_{7'}$, and —$NR_7R_{7'''}$;

$R_{6'}$ is selected from hydrogen, substituted or unsubstituted $C_{1-6}$ alkyl, substituted or unsubstituted $C_{2-6}$ alkenyl and substituted or unsubstituted $C_{2-6}$ alkynyl;

wherein the $C_{1-6}$ alkyl is preferably selected from methyl, ethyl, propyl, butyl, pentyl, hexyl, isopropyl, 2-methylpropyl, isopentyl or 3-pentanyl;

and/or the $C_{2-6}$-alkenyl is preferably selected from ethylene, propylene, butylene, pentylene or hexylene;

and/or the $C_{2-6}$-alkynyl is preferably selected from ethyne, propyne, butyne, pentyne or hexyne;

and/or $R_7$, $R_{7'}$ and $R_{7''}$ are independently selected from hydrogen, unsubstituted $C_{1-6}$ alkyl, unsubstituted $C_{2-6}$ alkenyl, unsubstituted $C_{2-6}$ alkynyl, and unsubstituted acetyl;

$R_{7'''}$ is selected from hydrogen, unsubstituted $C_{1-6}$ alkyl, unsubstituted $C_{2-6}$ alkenyl, unsubstituted $C_{2-6}$ alkynyl and -Boc;

wherein the $C_{1-6}$ alkyl is preferably selected from methyl, ethyl, propyl, butyl, pentyl, hexyl, isopropyl, 2-methylpropyl, isopentyl or 3-pentanyl;

and/or the $C_{2-6}$-alkenyl is preferably selected from ethylene, propylene, butylene, pentylene or hexylene;

and/or the $C_{2-6}$-alkynyl is preferably selected from ethyne, propyne, butyne, pentyne or hexyne;

and/or $R_8$, $R_{8'}$ and $R_{8''}$ are independently selected from hydrogen, unsubstituted $C_{1-6}$ alkyl, unsubstituted $C_{2-6}$ alkenyl, unsubstituted $C_{2-6}$ alkynyl, unsubstituted aryl or unsubstituted alkylaryl, unsubstituted cycloalkyl or unsubstituted alkylcycloalkyl, unsubstituted heterocyclyl and unsubstituted alkyheterocylcyl;

$R_{8'''}$ is selected from hydrogen, unsubstituted $C_{1-6}$ alkyl, unsubstituted $C_{2-6}$ alkenyl, unsubstituted $C_{2-6}$ alkynyl and -Boc;

wherein the alkyl is $C_{1-6}$ alkyl like methyl, ethyl, propyl, butyl, pentyl or hexyl;

and/or the $C_{1-6}$ alkyl is preferably selected from methyl, ethyl, propyl, butyl, pentyl, hexyl, isopropyl, or 2-methylpropyl, preferably the $C_{1-6}$ alkyl is methyl;

and/or the $C_{2-6}$-alkenyl is preferably selected from ethylene, propylene, butylene, pentylene or hexylene;

and/or the $C_{2-6}$-alkynyl is preferably selected from ethyne, propyne, butyne, pentyne or hexyne;

and/or the aryl is selected from phenyl, naphtyl, or anthracene; preferably is napthyl and phenyl; more preferably is phenyl;

and/or the heterocyclyl is a heterocyclic ring system of one or more saturated or unsaturated rings of which at least one ring contains one or more heteroatoms from the group consisting of nitrogen, oxygen and/or sulfur in the ring; preferably is a heterocyclic ring system of one or two saturated or unsaturated rings of which at least one ring contains one or more heteroatoms from the group consisting of nitrogen, oxygen and/or sulfur in the ring, more preferably is selected from oxazepan, pyrrolidine, imidazole, oxadiazole, tetrazole, pyridine, pyrimidine, piperidine, piperazine benzofuran, benzimidazole, indazole, benzothiazole, benzodiazole, thiazole, benzothiazole, tetrahydropyrane, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole oxopyrrolidine, pyrimidine, benzodioxolane, benzodioxane, carbazole and quinazoline;

and/or the cycloalkyl is $C_{3-8}$ cycloalkyl like cyclopropyl, cyclobutyl, cyclopentyl, cyclohexyl, cycloheptyl, or cyclooctyl; preferably is $C_{3-7}$ cycloalkyl like cyclopropyl, cyclobutyl, cyclopentyl, cyclohexyl, or cycloheptyl; more preferably from $C_{3-6}$ cycloalkyl like cyclopropyl, cyclobutyl, cyclopentyl or cyclohexyl;

and/or $R_9$, $R_{9'}$ and $R_{9''}$ are independently selected from hydrogen, unsubstituted $C_{1-6}$ alkyl, unsubstituted $C_{2-6}$ alkenyl and unsubstituted $C_{2-6}$ alkynyl;

$R_{9'''}$ is selected from hydrogen, unsubstituted $C_{1-6}$ alkyl, unsubstituted $C_{2-6}$ alkenyl, unsubstituted $C_{2-6}$ alkynyl and -Boc;

wherein the $C_{1-6}$ alkyl is preferably selected from methyl, ethyl, propyl, butyl, pentyl, hexyl, isopropyl, or 2-methylpropyl, more preferably the alkyl is methyl;

and/or the $C_{2-6}$-alkenyl is preferably selected from ethylene, propylene, butylene, pentylene or hexylene;

and/or the $C_{2-6}$-alkynyl is preferably selected from ethyne, propyne, butyne, pentyne or hexyne;

and/or $R_{10}$, $R_{10'}$ and $R_{10''}$ are independently selected from hydrogen, unsubstituted $C_{1-6}$ alkyl, unsubstituted $C_{2-6}$ alkenyl, and unsubstituted $C_{2-6}$ alkynyl;

$R_{10'''}$ is selected from hydrogen, unsubstituted $C_{1-6}$ alkyl, unsubstituted $C_{2-6}$ alkenyl, unsubstituted $C_{2-6}$ alkynyl and -Boc;

wherein the $C_{1-6}$ alkyl is preferably selected from methyl, ethyl, propyl, butyl, pentyl, hexyl, isopropyl, 2-methylpropyl, isopentyl or 3-pentanyl;

and/or the $C_{2-6}$-alkenyl is preferably selected from ethylene, propylene, butylene, pentylene or hexylene;

and/or the $C_{2-6}$-alkynyl is preferably selected from ethyne, propyne, butyne, pentyne or hexyne;

and/or $R_{11}$, $R_{11'}$ and $R_{11''}$ are independently selected from hydrogen, unsubstituted $C_{1-6}$ alkyl, unsubstituted $C_{2-6}$ alkenyl, unsubstituted $C_{2-6}$ alkynyl, unsubstituted aryl, unsubstituted alkylaryl, unsubstituted cycloalkyl and unsubstituted alkylcycloalkyl, unsubstituted heterocyclyl and unsubstituted alkyheterocylcyl;

$R_{11'''}$ is selected from hydrogen, unsubstituted $C_{1-6}$ alkyl, unsubstituted $C_{2-6}$ alkenyl, unsubstituted $C_{2-6}$ alkynyl and -Boc;

wherein the alkyl is $C_{1-6}$ alkyl like methyl, ethyl, propyl, butyl, pentyl or hexyl;

and/or the $C_{1-6}$ alkyl is preferably selected from methyl, ethyl, propyl, butyl, pentyl, hexyl, isopropyl, or 2-methylpropyl, preferably the $C_{1-6}$ alkyl is X;

and/or the $C_{2-6}$-alkenyl is preferably selected from ethylene, propylene, butylene, pentylene or hexylene;

and/or the $C_{2-6}$-alkynyl is preferably selected from ethyne, propyne, butyne, pentyne or hexyne;

and/or the aryl is selected from phenyl, naphtyl, or anthracene; preferably is phenyl;

and/or the heterocyclyl is a heterocyclic ring system of one or more saturated or unsaturated rings of which at least one ring contains one or more heteroatoms from the group consisting of nitrogen, oxygen and/or sulfur in the ring; preferably is a heterocyclic ring system of one or two saturated or unsaturated rings of which at least one ring contains one or more heteroatoms from the group consisting of nitrogen, oxygen and/or sulfur in the ring, more preferably is selected from oxazepan, pyrrolidine, imidazole, oxadiazole, tetrazole, pyridine, pyrimidine, piperidine, piperazine, benzofuran, benzimidazole, indazole, benzothiazole, benzodiazole, thiazole, benzothiazole, tetrahydropyrane, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole oxopyrrolidine, pyrimidine, benzodioxolane, benzodioxane, carbazole and quinazoline;

and/or the cycloalkyl is $C_{3-8}$ cycloalkyl like cyclopropyl, cyclobutyl, cyclopentyl, cyclohexyl, cycloheptyl, or cyclooctyl; preferably is $C_{3-7}$ cycloalkyl like cyclopropyl, cyclobutyl, cyclopentyl, cyclohexyl, or cycloheptyl; more preferably from $C_{3-6}$ cycloalkyl like cyclopropyl, cyclobutyl, cyclopentyl or cyclohexyl;

and/or $R_y$ is selected from hydrogen, substituted or unsubstituted $C_{1-6}$ alkyl, substituted or unsubstituted $C_{2-6}$ alkenyl, and substituted or unsubstituted $C_{2-6}$ alkynyl;

wherein the $C_{1-6}$ alkyl is preferably selected from methyl, ethyl, propyl, butyl, pentyl, hexyl, isopropyl, or 2-methylpropyl;

and/or the $C_{2-6}$-alkenyl is preferably selected from ethylene, propylene, butylene, pentylene or hexylene;

and/or the $C_{2-6}$-alkynyl is preferably selected from ethyne, propyne, butyne, pentyne or hexyne;

and/or $R_w$ is selected from hydrogen, substituted or unsubstituted $C_{1-6}$ alkyl, substituted or unsubstituted $C_{2-6}$ alkenyl, and substituted or unsubstituted $C_{2-6}$ alkynyl;

wherein the $C_{1-6}$ alkyl is preferably selected from methyl, ethyl, propyl, butyl, pentyl, hexyl, isopropyl, or 2-methylpropyl;

and/or the $C_{2-6}$-alkenyl is preferably selected from ethylene, propylene, butylene, pentylene or hexylene;

and/or the $C_{2-6}$-alkynyl is preferably selected from ethyne, propyne, butyne, pentyne or hexyne;

and/or n is 1, 2, 3, 4, 5 or 6, preferably n is 1 or 2;

and/or

X is a bond or —$CR_6R_{6'}$—, preferably X is a bond;

and/or

Y—W is $CR_y$—N or N—$CR_w$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general formula I the compound is a compound, wherein in $R_1$ as defined in any of the embodiments, the aryl is selected from phenyl, naphtyl, or anthracene; preferably is napthyl and phenyl; more preferably is phenyl;

and/or the heterocyclyl is a heterocyclic ring system of one or more saturated or unsaturated rings of which at least one ring contains one or more heteroatoms from the group consisting of nitrogen, oxygen and/or sulfur in the ring; preferably is a heterocyclic ring system of one or two saturated or unsaturated rings of which at least one ring contains one or more heteroatoms from the group consisting of nitrogen, oxygen and/or sulfur in the ring, more preferably is selected from oxazepan, pyrrolidine, imidazole, oxadiazole, tetrazole, pyridine, pyrimidine, piperidine, piperazine, benzofuran, benzimidazole, indazole, benzothiazole, benzodiazole, thiazole, benzothiazole, tetrahydropyrane, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole oxopyrrolidine, pyrimidine, benzodioxolane, benzodioxane, carbazole and quinazoline, more preferably the heterocyclyl is pyridine;

and/or the cycloalkyl is $C_{3-8}$ cycloalkyl like cyclopropyl, cyclobutyl, cyclopentyl, cyclohexyl, cycloheptyl, or cyclooctyl; preferably is $C_{3-7}$ cycloalkyl like cyclopropyl, cyclobutyl, cyclopentyl, cyclohexyl, or cycloheptyl; more preferably from $C_{3-6}$ cycloalkyl like cyclopropyl, cyclobutyl, cyclopentyl or cyclohexyl:

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general formula I the compound is a compound, wherein in $R_2$ as defined in any of the embodiments, the $C_{1-6}$ alkyl is preferably selected from methyl, ethyl, propyl, butyl, pentyl, hexyl, isopropyl, or 2-methylpropyl;

and/or the $C_{2-6}$-alkenyl is preferably selected from ethylene, propylene, butylene, pentylene or hexylene;

and/or the $C_{2-6}$-alkynyl is preferably selected from ethyne, propyne, butyne, pentyne or hexyne;

and/or the aryl is selected from phenyl, naphtyl, or anthracene; preferably is napthyl and phenyl; more preferably is phenyl;

and/or the heterocyclyl is a heterocyclic ring system of one or more saturated or unsaturated rings of which at least one ring contains one or more heteroatoms from the group consisting of nitrogen, oxygen and/or sulfur in the ring; preferably is a heterocyclic ring system of one or two saturated or unsaturated rings of which at least one ring contains one or more heteroatoms from the group consisting of nitrogen, oxygen and/or sulfur in the ring, more preferably is selected from oxazepan, pyrrolidine, imidazole, oxadiazole, tetrazole, pyridine, pyrimidine, piperidine, piperazine, benzofuran, benzimidazole, indazole, benzothiazole, benzodiazole, thiazole, benzothiazole, tetrahydropyrane, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole oxopyrrolidine, pyrimidine, benzodioxolane, benzodioxane, carbazole and quinazoline, more preferably the heterocyclyl is pyridine or thiazole;

and/or the cycloalkyl is $C_{3-8}$ cycloalkyl like cyclopropyl, cyclobutyl, cyclopentyl, cyclohexyl, cycloheptyl, or cyclooctyl; preferably is $C_{3-7}$ cycloalkyl like cyclopropyl, cyclobutyl, cyclopentyl, cyclohexyl, or cycloheptyl; more preferably from $C_{3-6}$ cycloalkyl like cyclopropyl, cyclobutyl, cyclopentyl or cyclohexyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general formula I the compound is a compound, wherein in $R_3$ as defined in any of the embodiments, the alkyl is $C_{1-6}$ alkyl like methyl, ethyl, propyl, butyl, pentyl or hexyl;

and/or the $C_{1-6}$ alkyl is preferably selected from methyl, ethyl, propyl, butyl, pentyl, hexyl, isopropyl, or 2-methylpropyl, preferably the $C_{1-6}$ alkyl is methyl;

and/or the $C_{2-6}$-alkenyl is preferably selected from ethylene, propylene, butylene, pentylene or hexylene;

and/or the $C_{2-6}$-alkynyl is preferably selected from ethyne, propyne, butyne, pentyne or hexyne;

and/or the aryl is selected from phenyl, naphtyl, or anthracene; preferably is napthyl and phenyl; more preferably is phenyl;

and/or the heterocyclyl is a heterocyclic ring system of one or more saturated or unsaturated rings of which at least one ring contains one or more heteroatoms from the group consisting of nitrogen, oxygen and/or sulfur in the ring; preferably is a heterocyclic ring system of one or two saturated or unsaturated rings of which at least one ring contains one or more heteroatoms from the group consisting of nitrogen, oxygen and/or sulfur in the ring, more preferably is selected from oxazepan, pyrrolidine, imidazole, oxadiazole, tetrazole, pyridine, pyrimidine, piperidine, piperazine, benzofuran, benzimidazole, indazole, benzothiazole, benzodiazole, thiazole, benzothiazole, tetrahydropyrane, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole oxopyrrolidine, pyrimidine, benzodioxolane, benzodioxane, carbazole and quinazoline;

and/or the cycloalkyl is $C_{3-8}$ cycloalkyl like cyclopropyl, cyclobutyl, cyclopentyl, cyclohexyl, cycloheptyl, or cyclooctyl; preferably is $C_{3-7}$ cycloalkyl like cyclopropyl, cyclobutyl, cyclopentyl, cyclohexyl, or cycloheptyl; more preferably from $C_{3-6}$ cycloalkyl like cyclopropyl, cyclobutyl, cyclopentyl or cyclohexyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general formula I the compound is a compound, wherein in $R_4$, $R_{4'}$, $R_{4''}$ and $R_{4'''}$ as defined in any of the embodiments, the $C_{1-6}$ alkyl is preferably selected from methyl, ethyl, propyl, butyl, pentyl, hexyl, isopropyl, 2-methylpropyl, isopentyl or 3-pentanyl;

and/or the $C_{2-6}$-alkenyl is preferably selected from ethylene, propylene, butylene, pentylene or hexylene;

and/or the $C_{2-6}$-alkynyl is preferably selected from ethyne, propyne, butyne, pentyne or hexyne;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general formula I the compound is a compound, wherein in $R_5$ and $R_{5'}$ as defined in any of the embodiments, the $C_{1-6}$ alkyl is preferably selected from methyl, ethyl, propyl, butyl, pentyl, hexyl, isopropyl, 2-methylpropyl, isopentyl or 3-pentanyl;

and/or the $C_{2-6}$-alkenyl is preferably selected from ethylene, propylene, butylene, pentylene or hexylene;

and/or the $C_{2-6}$-alkynyl is preferably selected from ethyne, propyne, butyne, pentyne or hexyne;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general formula I the compound is a compound, wherein in $R_6$ and $R_{6'}$ as defined in any of the embodiments, the $C_{1-6}$ alkyl is preferably selected from methyl, ethyl, propyl, butyl, pentyl, hexyl, isopropyl, 2-methylpropyl, isopentyl or 3-pentanyl;

and/or the $C_{2-6}$-alkenyl is preferably selected from ethylene, propylene, butylene, pentylene or hexylene;

and/or the $C_{2-6}$-alkynyl is preferably selected from ethyne, propyne, butyne, pentyne or hexyne;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general formula I the compound is a compound, wherein in $R_7$, $R_{7'}$, $R_{7''}$ and $R_{7'''}$ as defined in any of the embodiments, the $C_{1-6}$ alkyl is preferably selected from methyl, ethyl, propyl, butyl, pentyl, hexyl, isopropyl, 2-methylpropyl, isopentyl or 3-pentanyl;

and/or the $C_{2-6}$-alkenyl is preferably selected from ethylene, propylene, butylene, pentylene or hexylene;

and/or the $C_{2-6}$-alkynyl is preferably selected from ethyne, propyne, butyne, pentyne or hexyne;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general formula I the compound is a compound, wherein in $R_8$, $R_{8'}$, $R_{8''}$ and $R_{8'''}$ as defined in any of the embodiments, the alkyl is $C_{1-6}$ alkyl like methyl, ethyl, propyl, butyl, pentyl or hexyl;

and/or the $C_{1-6}$ alkyl is preferably selected from methyl, ethyl, propyl, butyl, pentyl, hexyl, isopropyl, or 2-methylpropyl, preferably the $C_{1-6}$ alkyl is methyl;

and/or the $C_{2-6}$-alkenyl is preferably selected from ethylene, propylene, butylene, pentylene or hexylene;

and/or the $C_{2-6}$-alkynyl is preferably selected from ethyne, propyne, butyne, pentyne or hexyne;

and/or the aryl is selected from phenyl, naphtyl, or anthracene; preferably is napthyl and phenyl; more preferably is phenyl;

and/or the heterocyclyl is a heterocyclic ring system of one or more saturated or unsaturated rings of which at least one ring contains one or more heteroatoms from the group consisting of nitrogen, oxygen and/or sulfur in the ring; preferably is a heterocyclic ring system of one or two saturated or unsaturated rings of which at least one ring contains one or more heteroatoms from the group consisting of nitrogen, oxygen and/or sulfur in the ring, more preferably is selected from oxazepan, pyrrolidine, imidazole, oxadiazole, tetrazole, pyridine, pyrimidine, piperidine, piperazine benzofuran, benzimidazole, indazole, benzothiazole, benzodiazole, thiazole, benzothiazole, tetrahydropyrane, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole oxopyrrolidine, pyrimidine, benzodioxolane, benzodioxane, carbazole and quinazoline;

and/or the cycloalkyl is $C_{3-8}$ cycloalkyl like cyclopropyl, cyclobutyl, cyclopentyl, cyclohexyl, cycloheptyl, or cyclooctyl; preferably is $C_{3-7}$ cycloalkyl like cyclopropyl, cyclobutyl, cyclopentyl, cyclohexyl, or cycloheptyl; more preferably from $C_{3-6}$ cycloalkyl like cyclopropyl, cyclobutyl, cyclopentyl or cyclohexyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general formula I the compound is a compound, wherein in $R_9$, $R_{9'}$, $R_{9''}$ and $R_{9'''}$ as defined in any of the embodiments, the $C_{1-6}$ alkyl is preferably selected from methyl, ethyl, propyl, butyl, pentyl, hexyl, isopropyl, or 2-methylpropyl, more preferably the alkyl is methyl;

and/or the $C_{2-6}$-alkenyl is preferably selected from ethylene, propylene, butylene, pentylene or hexylene;

and/or the $C_{2-6}$-alkynyl is preferably selected from ethyne, propyne, butyne, pentyne or hexyne;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general formula I the compound is a compound, wherein in $R_{10}$, $R_{10'}$, $R_{10''}$ and $R_{10'''}$ as defined in any of the embodiments, the $C_{1-6}$ alkyl is preferably selected from methyl, ethyl, propyl, butyl, pentyl, hexyl, isopropyl, 2-methylpropyl, isopentyl or 3-pentanyl;

and/or the $C_{2-6}$-alkenyl is preferably selected from ethylene, propylene, butylene, pentylene or hexylene;

and/or the $C_{2-6}$-alkynyl is preferably selected from ethyne, propyne, butyne, pentyne or hexyne;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general formula I the compound is a compound, wherein in $R_{11}$, $R_{11'}$, $R_{11''}$ and $R_{11'''}$ as defined in any of the embodiments, the alkyl is $C_{1-6}$ alkyl like methyl, ethyl, propyl, butyl, pentyl or hexyl;

and/or the $C_{1-6}$ alkyl is preferably selected from methyl, ethyl, propyl, butyl, pentyl, hexyl, isopropyl, or 2-methylpropyl, preferably the $C_{1-6}$ alkyl is X;

and/or the $C_{2-6}$-alkenyl is preferably selected from ethylene, propylene, butylene, pentylene or hexylene;

and/or the $C_{2-6}$-alkynyl is preferably selected from ethyne, propyne, butyne, pentyne or hexyne;

and/or the aryl is selected from phenyl, naphtyl, or anthracene; preferably is phenyl;

and/or the heterocyclyl is a heterocyclic ring system of one or more saturated or unsaturated rings of which at least one ring contains one or more heteroatoms from the group consisting of nitrogen, oxygen and/or sulfur in the ring; preferably is a heterocyclic ring system of one or two saturated or unsaturated rings of which at least one ring contains one or more heteroatoms from the group consisting of nitrogen, oxygen and/or sulfur in the ring, more preferably is selected from oxazepan, pyrrolidine, imidazole, oxadiazole, tetrazole, pyridine, pyrimidine, piperidine, piperazine, benzofuran, benzimidazole, indazole, benzothiazole, benzodiazole, thiazole, benzothiazole, tetrahydropyrane, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole oxopyrrolidine, pyrimidine, benzodioxolane, benzodioxane, carbazole and quinazoline;

and/or the cycloalkyl is $C_{3-8}$ cycloalkyl like cyclopropyl, cyclobutyl, cyclopentyl, cyclohexyl, cycloheptyl, or cyclooctyl; preferably is $C_{3-7}$ cycloalkyl like cyclopropyl, cyclobutyl, cyclopentyl, cyclohexyl, or cycloheptyl; more preferably from $C_{3-6}$ cycloalkyl like cyclopropyl, cyclobutyl, cyclopentyl or cyclohexyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general formula I the compound is a compound, wherein in $R_y$ as defined in any of the above embodiments,
the $C_{1-6}$ alkyl is preferably selected from methyl, ethyl, propyl, butyl, pentyl, hexyl, isopropyl, or 2-methylpropyl;
and/or
the $C_{2-6}$-alkenyl is preferably selected from ethylene, propylene, butylene, pentylene or hexylene;
and/or
the $C_{2-6}$-alkynyl is preferably selected from ethyne, propyne, butyne, pentyne or hexyne;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general formula I the compound is a compound, wherein in $R_w$ as defined in any of the embodiments,
the $C_{1-6}$ alkyl is preferably selected from methyl, ethyl, propyl, butyl, pentyl, hexyl, isopropyl, or 2-methylpropyl;
and/or
the $C_{2-6}$-alkenyl is preferably selected from ethylene, propylene, butylene, pentylene or hexylene;
and/or
the $C_{2-6}$-alkynyl is preferably selected from ethyne, propyne, butyne, pentyne or hexyne;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general formula I the compound is a compound, wherein
n is 1, 2, 3, 4, 5 or 6, preferably n is 1or 2;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general formula I the compound is a compound, wherein
X is a bond or —$CR_6R_{6'}$—, preferably X is a bond;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general formula I the compound is a compound, wherein
X is a bond or —$CR_6R_{6'}$—, preferably X is a —$CR_6R_{6'}$—;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general formula I the compound is a compound, wherein
Y—W is $CR_y$—N or N—$CR_w$, preferably Y—W is —$CR_y$—N—;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general formula I the compound is a compound, wherein
Y—W is $CR_y$—N or N—$CR_w$, preferably Y—W is —N—$CR_w$—;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment
$R_1$ is a substituted or unsubstituted group selected from phenyl and pyridine.
In a preferred embodiment
$R_2$ is a substituted or unsubstituted group selected from phenyl, pyridine or thiazole.
In a preferred embodiment
$R_3$ is substituted or unsubstituted methyl.
In a preferred embodiment
$R_4$, $R_{4'}$, $R_{4''}$ and $R_{4'''}$ are all hydrogen.
In a preferred embodiment
$R_5$ and $R_{5'}$ are both hydrogen.
In a preferred embodiment
$R_6$ is selected from hydrogen and hydroxy.
In another preferred embodiment
$R_{6'}$ is hydrogen.
In another preferred embodiment
$R_6$ is hydroxy while and $R_{6'}$ is hydrogen.
In another preferred embodiment
$R_6$ and $R_{6'}$ are both hydrogen.
In a preferred embodiment
$R_7$ is hydrogen.
In a preferred embodiment
$R_8$ is hydrogen or substituted or unsubstituted methyl.
In a preferred embodiment
$R_9$ is hydrogen or substituted or unsubstituted methyl.
In a preferred embodiment
$R_{9'}$ is substituted or unsubstituted methyl.
In a preferred embodiment
$R_{9'''}$ is hydrogen.
In a preferred embodiment
$R_9$ is hydrogen while $R_{9'}$ is substituted or unsubstituted methyl.
In a preferred embodiment
$R_9$ and $R_{9'''}$ are both hydrogen.
In a preferred embodiment
$R_y$ is hydrogen.
In a preferred embodiment
$R_w$ is hydrogen.
In another preferred embodiment
n is 1 or 2.
In another preferred embodiment
Y—W is —CH—N— or —N—CH—.
In another preferred embodiment
X is a bond, —$CH_2$—, or —CH(OH)—.

In another preferred embodiment
X is a bond or —CH$_2$—.

In another preferred embodiment
X is a bond.

In another preferred embodiment
X is —CH$_2$—.

In another preferred embodiment
X is —CH(OH)—.

In an particular embodiment
the halogen is fluorine, chlorine, iodine or bromine.

In an particular embodiment
the halogen is fluorine or chlorine.

In another preferred further embodiment, the compounds of the general formula I are compounds of general Formula Ia

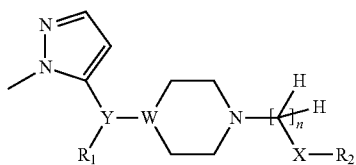

(Ia)

wherein
n is 1 or 2;
Y—W is CH—N or N—CH;
X is a bond or —CR$_6$H—;
R$_1$ is substituted or unsubstituted cycloalkyl, substituted or unsubstituted aryl, or substituted or unsubstituted heterocyclyl;
  wherein said cycloalkyl, aryl or heterocyclyl in R$_1$, if substituted, being substituted with one or more substituents selected from halogen, —R$_8$, —OR$_8$, —NO$_2$, —NR$_8$R$_{8'''}$, NR$_8$C(O)R$_{8'}$, —NR$_8$S(O)$_2$R$_{8'}$, —S(O)$_2$NR$_8$R$_{8'}$, —NR$_8$C(O)NR$_{8'}$R$_{8''}$, —SR$_8$, —S(O)R$_8$, —S(O)$_2$R$_8$, —CN, haloalkyl, haloalkoxy, —C(O)OR$_8$, —C(O)NR$_8$R$_{8'}$, —OCH$_2$CH$_2$OH, —NR$_8$S(O)$_2$NR$_8$R$_{8''}$ and C(CH$_3$)$_2$OR$_8$;
  wherein R$_8$, R$_{8'}$ and R$_{8''}$ are independently selected from hydrogen, unsubstituted C$_{1-6}$ alkyl, unsubstituted C$_{2-6}$ alkenyl, unsubstituted C$_{2-6}$ alkynyl, unsubstituted aryl or unsubstituted alkylaryl, unsubstituted cycloalkyl or unsubstituted alkylcycloalkyl, unsubstituted heterocyclyl and unsubstituted alkyheterocylcyl;
  and wherein R$_{8'''}$ is selected from hydrogen, unsubstituted C$_{1-6}$ alkyl, unsubstituted C$_{2-6}$ alkenyl, unsubstituted C$_{2-6}$ alkynyl and -Boc;
R$_2$ is substituted or unsubstituted C$_{1-6}$ alkyl, substituted or unsubstituted C$_{2-6}$ alkenyl, substituted or unsubstituted C$_{2-6}$ alkynyl, substituted or unsubstituted cycloalkyl, substituted or unsubstituted aryl or substituted or unsubstituted heterocyclyl;
  wherein said cycloalkyl, aryl or heterocyclyl in R$_2$, if substituted, is substituted with one or more substituents selected from halogen, —R$_9$, —OR$_9$, —NO$_2$, —NR$_9$R$_{9'''}$, NR$_9$C(O)R$_{9'}$, —NR$_9$S(O)$_2$R$_{9'}$, —N(S(O)$_2$R$_9$)(S(O)$_2$R$_{9'}$), —S(O)$_2$NR$_9$R$_{9'}$, —NR$_9$C(O)NR$_{9'}$R$_{9''}$, —SR$_9$, —S(O)R$_9$, S(O)$_2$R$_9$, —CN, haloalkyl, haloalkoxy, —C(O)OR$_9$, —C(O)NR$_9$R$_{9'}$, —OCH$_2$CH$_2$OH, —NR$_9$S(O)$_2$NR$_{9'}$R$_{9''}$ and C(CH$_3$)$_2$OR$_9$;
  wherein the alkyl, alkylene or alkynyl in R$_2$, if substituted, is substituted with one or more substituents selected from —OR$_9$, halogen, —CN, haloalkyl, haloalkoxy, —NR$_9$R$_{9'''}$, —SR$_9$, —S(O)R$_9$, and —S(O)$_2$R$_9$;
  wherein R$_9$, R$_{9'}$ and R$_{9''}$ are independently selected from hydrogen, unsubstituted C$_{1-6}$ alkyl, unsubstituted C$_{2-6}$ alkenyl, and unsubstituted C$_{2-6}$ alkynyl;
  and wherein R$_{9'''}$ is selected from hydrogen, unsubstituted C$_{1-6}$ alkyl, unsubstituted C$_{2-6}$ alkenyl, unsubstituted C$_{2-6}$ alkynyl and -Boc;
R$_6$ is selected from hydrogen, halogen, —OR$_7$, and substituted or unsubstituted C$_{1-6}$ alkyl;
  wherein R$_7$, R$_{7'}$ and R$_{7''}$ are independently selected from hydrogen, and unsubstituted C$_{1-6}$ alkyl;
and
wherein the alkyl, alkylene or alkynyl, other than those defined in R$_1$ or R$_2$, if substituted, is substituted with one or more substituents selected from —OR$_{10}$, halogen, —CN, haloalkyl, haloalkoxy, —NR$_{10}$R$_{10'''}$, —SR$_{10}$, —S(O)R$_{10}$, and —S(O)$_2$R$_{10}$;
  wherein R$_{10}$, R$_{10'}$ and R$_{10''}$ are independently selected from hydrogen, unsubstituted C$_{1-6}$ alkyl, unsubstituted C$_{2-6}$ alkenyl, and unsubstituted C$_{2-6}$ alkynyl;
  and wherein R$_{10'''}$ is selected from hydrogen, unsubstituted C$_{1-6}$ alkyl, unsubstituted C$_{2-6}$ alkenyl, unsubstituted C$_{2-6}$ alkynyl and -Boc;
and/or
wherein the aryl, heterocyclyl or cycloalkyl, also in alkylaryl, alkylcycloalkyl and alkylheterocyclyl, other than those defined in R$_1$ or R$_2$, if substituted, is substituted with one or more substituents selected from halogen, —R$_{11}$, —OR$_{11}$, —NO$_2$, —NR$_{11}$R$_{11'''}$, NR$_{11}$C(O)R$_{11'}$, —NR$_{11}$S(O)$_2$R$_{11'}$, —S(O)$_2$NR$_{11}$R$_{11'}$, —NR$_{11}$C(O)NR$_{11'}$R$_{11''}$, —SR$_{11}$, —S(O)R$_{11}$, S(O)$_2$R11, —CN, haloalkyl, haloalkoxy, —C(O)OR$_{11}$, —C(O)NR$_{11}$R$_{11'}$, —OCH$_2$CH$_2$OH, —NR$_{11}$S(O)$_2$NR$_{11'}$R$_{11''}$ and C(CH$_3$)$_2$OR$_{11}$;
  wherein R$_{11}$, R$_{11'}$ and R$_{11''}$ are independently selected from hydrogen, unsubstituted C$_{1-6}$ alkyl, unsubstituted C$_{2-6}$ alkenyl, unsubstituted C$_{2-6}$ alkynyl, unsubstituted aryl, unsubstituted alkylaryl, unsubstituted cycloalkyl and unsubstituted alkylcycloalkyl, unsubstituted heterocyclyl and unsubstituted alkyheterocylcyl;
and wherein R$_{11'''}$ is selected from hydrogen, unsubstituted C$_{1-6}$ alkyl, unsubstituted C$_{2-6}$ alkenyl, unsubstituted C$_{2-6}$ alkynyl and -Boc,
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In the context of this invention in regards to Formula (Ia), and in order to avoid any issue of clarity, when Y—W is CH—N it is understood that Y—W represents

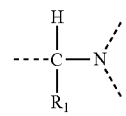

in Formula (Ia).

In the context of this invention in regards to Formula (Ia), and as to avoid any issue of clarity, when Y—W is N—CH, it is understood that Y—W represents

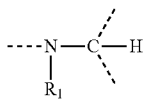

in Formula (Ia).

In preferred embodiments of the compound according to Formula (Ia), the preferred embodiments set out above and below for a compound according to Formula (I) and especially for its substituents would also apply to the compound according to Formula (Ia).

In a preferred further embodiment, the compounds of the general formula I (and of Formula (Ia)) are selected from

| EX | Chemical name |
|----|---------------|
| 1  | 1-((1-methyl-1H-pyrazol-5-yl)(phenyl)methyl)-4-(2-(pyridin-2-yl)ethyl)piperazine |
| 2  | 1-benzyl-4-((1-methyl-1H-pyrazol-5-yl)(phenyl)methyl)piperazine |
| 3  | 1-((1-methyl-1H-pyrazol-5-yl)(phenyl)methyl)-4-phenethylpiperazine |
| 4  | 1-((1-methyl-1H-pyrazol-5-yl)(pyridin-2-yl)methyl)-4-phenethylpiperazine |
| 5  | 1-((1-methyl-1H-pyrazol-5-yl)(pyridin-3-yl)methyl)-4-phenethylpiperazine |
| 6  | 1-(2-methoxyphenethyl)-4-((1-methyl-1H-pyrazol-5-yl)(phenyl)methyl)piperazine |
| 7  | 1-((3-methoxyphenyl)(1-methyl-1H-pyrazol-5-yl)methyl)-4-phenethylpiperazine |
| 8  | 1-((2-methoxyphenyl)(1-methyl-1H-pyrazol-5-yl)methyl)-4-phenethylpiperazine |
| 9  | 1-((4-methoxyphenyl)(1-methyl-1H-pyrazol-5-yl)methyl)-4-phenethylpiperazine |
| 10 | 1-((1-methyl-1H-pyrazol-5-yl)(6-(trifluoromethyl)pyridin-2-yl)methyl)-4-phenethylpiperazine |
| 11 | 1-((1-methyl-1H-pyrazol-5-yl)(6-(trifluoromethyl)pyridin-3-yl)methyl)-4-phenethylpiperazine |
| 12 | 1-((5-fluoropyridin-2-yl)(1-methyl-1H-pyrazol-5-yl)methyl)-4-phenethylpiperazine |
| 13 | 1-((5-fluoropyridin-3-yl)(1-methyl-1H-pyrazol-5-yl)methyl)-4-phenethylpiperazine |
| 14 | 1-((1-methyl-1H-pyrazol-5-yl)(5-(trifluoromethyl)pyridin-2-yl)methyl)-4-phenethylpiperazine |
| 15 | 1-((5-fluoropyridin-2-yl)(1-methyl-1H-pyrazol-5-yl)methyl)-4-(2-(pyridin-2-yl)ethyl)piperazine |
| 16 | 1-((3-fluoropyridin-2-yl)(1-methyl-1H-pyrazol-5-yl)methyl)-4-phenethylpiperazine |
| 17 | 1-((1-methyl-1H-pyrazol-5-yl)(2-(trifluoromethyl)pyridin-3-yl)methyl)-4-phenethylpiperazine |
| 18 | 1-((5-chloropyridin-2-yl)(1-methyl-1H-pyrazol-5-yl)methyl)-4-phenethylpiperazine |
| 19 | 1-((1-methyl-1H-pyrazol-5-yl)(4-(trifluoromethyl)pyridin-3-yl)methyl)-4-phenethylpiperazine |
| 20 | 1-((1-methyl-1H-pyrazol-5-yl)(pyridin-4-yl)methyl)-4-phenethylpiperazine |
| 21 | 1-(3-methoxyphenethyl)-4-((1-methyl-1H-pyrazol-5-yl)(phenyl)methyl)piperazine |
| 22 | 1-(2-fluorophenethyl)-4-((1-methyl-1H-pyrazol-5-yl)(phenyl)methyl)piperazine |
| 23 | 1-(4-fluorophenethyl)-4-((1-methyl-1H-pyrazol-5-yl)(phenyl)methyl)piperazine |
| 24 | 1-((1-methyl-1H-pyrazol-5-yl)(phenyl)methyl)-4-(2-(6-(trifluoromethyl)pyridin-3-yl)ethyl)piperazine |
| 25 | tert-butyl 4-(2-(4-((1-methyl-1H-pyrazol-5-yl)(phenyl)methyl)piperazin-1-yl)ethyl)thiazol-2-ylcarbamate |
| 26 | 1-(2-fluorophenethyl)-4-((5-fluoropyridin-2-yl)(1-methyl-1H-pyrazol-5-yl)methyl)piperazine |
| 27 | 1-((5-fluoropyridin-2-yl)(1-methyl-1H-pyrazol-5-yl)methyl)-4-(3-methoxyphenethyl)piperazine |
| 28 | 2-(2-(4-((1-methyl-1H-pyrazol-5-yl)(phenyl)methyl)piperazin-1-yl)ethyl)phenol |
| 29 | 3-((1-methyl-1H-pyrazol-5-yl)(4-phenethylpiperazin-1-yl)methyl)phenol |
| 30 | 3-(2-(4-((1-methyl-1H-pyrazol-5-yl)(phenyl)methyl)piperazin-1-yl)ethyl)phenol |
| 31 | 3-(2-(4-((5-fluoropyridin-2-yl)(1-methyl-1H-pyrazol-5-yl)methyl)piperazin-1-yl)ethyl)phenol |
| 32 | 4-(2-(4-((1-methyl-1H-pyrazol-5-yl)(phenyl)methyl)piperazin-1-yl)ethyl)thiazol-2-amine |
| 33 | 1-(2-(3-fluoropyridin-2-yl)ethyl)-4-((1-methyl-1H-pyrazol-5-yl)(phenyl)methyl)piperazine |
| 34 | 1-(2-(5-fluoropyridin-2-yl)ethyl)-4-((1-methyl-1H-pyrazol-5-yl)(phenyl)methyl)piperazine |
| 35 | 1-(3-fluorophenethyl)-4-((1-methyl-1H-pyrazol-5-yl)(phenyl)methyl)piperazine |
| 36 | 1-((1-methyl-1H-pyrazol-5-yl)(phenyl)methyl)-4-(2-(pyridin-3-yl)ethyl)piperazine |
| 37 | 1-((1-methyl-1H-pyrazol-5-yl)(phenyl)methyl)-4-(2-(pyridin-4-yl)ethyl)piperazine |
| 38 | 1-(3-fluorophenethyl)-4-((5-fluoropyridin-2-yl)(1-methyl-1H-pyrazol-5-yl)methyl)piperazine |
| 39 | 2-(4-((1-methyl-1H-pyrazol-5-yl)(phenyl)methyl)piperazin-1-yl)-1-phenylethanol |
| 40 | 6-(2-(4-((1-methyl-1H-pyrazol-5-yl)(phenyl)methyl)piperazin-1-yl)ethyl)pyridin-2-amine |
| 41 | 1-(2-(3-chloropyridin-2-yl)ethyl)-4-((1-methyl-1H-pyrazol-5-yl)(phenyl)methyl)piperazine |
| 42 | 1-((1-methyl-1H-pyrazol-5-yl)(phenyl)methyl)-4-(2-(6-(trifluoromethyl)pyridin-2-yl)ethyl)piperazine |
| 43 | 1-(2-(3-chloropyridin-2-yl)ethyl)-4-((5-fluoropyridin-2-yl)(1-methyl-1H-pyrazol-5-yl)methyl)piperazine |
| 44 | N-(6-(2-(4-((1-methyl-1H-pyrazol-5-yl)(phenyl)methyl)piperazin-1-yl)ethyl)pyridin-2-yl)methanesulfonamide |
| 45 | N-(6-(2-(4-((1-methyl-1H-pyrazol-5-yl)(phenyl)methyl)piperazin-1-yl)ethyl)pyridin-2-yl)-N-(methylsulfonyl)methanesulfonamide |
| 46 | N-(1-methyl-1H-pyrazol-5-yl)-1-phenethyl-N-phenylpiperidin-4-amine |
| 47 | 1-benzyl-N-(1-methyl-1H-pyrazol-5-yl)-N-phenylpiperidin-4-amine | optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another very preferred embodiment, the compound according to the invention of general formula I, is a compound wherein Y—W is $CR_y$—N, the compound being exemplified in examples 1 to 45;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another very preferred embodiment, the compound according to the invention of general formula I, is a compound wherein Y—W is N—$CR_w$, the compound being exemplified in examples 46 and 47;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another very preferred embodiment, the compound according to the invention of general formula I, is a compound wherein n is 1 or 2, X is a bond and $R_2$ is a substituted or unsubstituted group selected from phenyl, pyridine and thiazole, the compound being exemplified in examples 1 to 38 and 40 to 47;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another very preferred embodiment, the compound according to the invention of general formula I, is a compound wherein n is 1 or 2, X is a bond and $R_1$ is a substituted or unsubstituted group selected from phenyl and pyridine, the compound being exemplified in examples 1 to 38 and 40 to 47;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another very preferred embodiment, the compound according to the invention of general formula I, is a compound wherein n is 1 or 2, X is a bond, $R_1$ is a substituted or unsubstituted group selected from phenyl and pyridine, and $R_2$ is a substituted or unsubstituted group selected from phenyl, pyridine and thiazole, the compound being exemplified in examples 1 to 38 and 40 to 47;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another very preferred embodiment, the compound according to the invention of general formula I is a compound wherein n is 1 or 2, X is a bond, Y—W is —CH—N—, $R_1$ is a substituted or unsubstituted group selected from phenyl and pyridine, and $R_2$ is a substituted or unsubstituted group selected from phenyl, pyridine and thiazole, the compound exemplified in from examples 1 to 38 and 40 to 45;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another very preferred embodiment, the compound according to the invention of general formula I is a compound wherein n is 1, the compound being exemplified in examples 1 to 47;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another very preferred embodiment, the compound according to the invention of general formula I is a compound wherein n is 2, the compound being exemplified in examples 1, 3 to 38 and 40 to 46;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment of the compound according to the invention of general formula I wherein $R_1$ is substituted or unsubstituted cycloalkyl, substituted or unsubstituted aryl, or substituted or unsubstituted heterocyclyl;

wherein said cycloalkyl, aryl or heterocyclyl in $R_1$, if substituted, being substituted with one or more substituents selected from halogen, —$R_8$, —$OR_8$, —$NO_2$, —$NR_8R_{8'''}$, $NR_8C(O)R_{8'}$, —$NR_8S(O)_2R_{8'}$, —$S(O)_2NR_8R_{8'}$, —$NR_8C(O)NR_8R_{8''}$, —$SR_8$, —$S(O)R_8$, —$S(O)_2R_8$, —CN, haloalkyl, haloalkoxy, —$C(O)OR_8$, —$C(O)NR_8R_{8'}$, —$OCH_2CH_2OH$, —$NR_8S(O)_2NR_8R_{8''}$ and $C(CH_3)_2OR_8$;

wherein $R_8$, $R_{8'}$ and $R_{8''}$ are independently selected from hydrogen, unsubstituted $C_{1-6}$ alkyl, unsubstituted $C_{2-6}$ alkenyl, unsubstituted $C_{2-6}$ alkynyl, unsubstituted aryl or unsubstituted alkylaryl, unsubstituted cycloalkyl or unsubstituted alkylcycloalkyl, unsubstituted heterocyclyl and unsubstituted alkyheterocylcyl;

and wherein $R_{8'''}$, is selected from hydrogen, unsubstituted $C_{1-6}$ alkyl, unsubstituted $C_{2-6}$ alkenyl, unsubstituted $C_{2-6}$ alkynyl and -Boc;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another embodiment of the invention the compound of general formula I, $R_2$ is substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl or substituted or unsubstituted heterocyclyl;

wherein said cycloalkyl, aryl or heterocyclyl in $R_2$, if substituted, is substituted with one or more substituents selected from halogen, —$R_9$, —$OR_9$, —$NO_2$, —$NR_9R_{9'''}$, $NR_9C(O)R_{9'}$, —$NR_9S(O)_2R_{9'}$, —$N(S(O)_2R_9)(S(O)_2R_{9'})$, —$S(O)_2NR_9R_{9'}$, —$NR_9C(O)NR_9R_{9''}$, —$SR_9$, —$S(O)R_9$, $S(O)_2R_9$, —CN, haloalkyl, haloalkoxy, —$C(O)OR_9$, —$C(O)NR_9R_{9'}$, —$OCH_2CH_2OH$, —$NR_9S(O)_2NR_9R_{9''}$ and $C(CH_3)_2OR_9$;

wherein the alkyl, alkylene or alkynyl in $R_2$, if substituted, is substituted with one or more substituents selected from —$OR_9$, halogen, —CN, haloalkyl, haloalkoxy, —$NR_9R_{9'''}$, —$SR_9$, —$S(O)R_9$, and —$S(O)_2R_9$;

wherein $R_9$, $R_{9'}$ and $R_{9''}$ are independently selected from hydrogen, unsubstituted $C_{1-6}$ alkyl, unsubstituted $C_{2-6}$ alkenyl, and unsubstituted $C_{2-6}$ alkynyl;

and wherein $R_{9'''}$ is selected from hydrogen, unsubstituted $C_{1-6}$ alkyl, unsubstituted $C_{2-6}$ alkenyl, unsubstituted $C_{2-6}$ alkynyl and -Boc;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another embodiment of the invention the compound of general formula I, wherein the alkyl, alkylene or alkynyl, other than those defined in $R_1$ or $R_2$, if substituted, is substituted with one or more substituents selected from —$OR_{10}$, halogen, —CN, haloalkyl, haloalkoxy, —$NR_{10}R_{10'''}$, —$SR_{10}$, —$S(O)R_{10}$, and —$S(O)_2R_{10}$;

wherein $R_{10}$, $R_{10'}$ and $R_{10''}$ are independently selected from hydrogen, unsubstituted $C_{1-6}$ alkyl, unsubstituted $C_{2-6}$ alkenyl, and unsubstituted $C_{2-6}$ alkynyl;

and wherein $R_{10'''}$ is selected from hydrogen, unsubstituted $C_{1-6}$ alkyl, unsubstituted $C_{2-6}$ alkenyl, unsubstituted $C_{2-6}$ alkynyl and -Boc;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another embodiment of the invention the compound of general formula I,
wherein the aryl, heterocyclyl or cycloalkyl, also in alkylaryl, alkylcycloalkyl and alkylheterocyclyl, other than those defined in $R_1$ or $R_2$, if substituted, is substituted with one or more substituents selected from halogen, —$R_{11}$, —$OR_{11}$, —$NO_2$, —$NR_{11}R_{11'''}$, $NR_{11}C(O)R_{11'}$, —$NR_{11}S(O)_2R_{11'}$, —$S(O)_2NR_{11}R_{11'}$, —$NR_{11}C(O)NR_{11'}R_{11''}$, —$SR_{11}$, —$S(O)R_{11}$, $S(O)_2R11$, —CN, haloalkyl, haloalkoxy, —$C(O)OR_{11}$, —$C(O)NR_{11}R_{11'}$, —$OCH_2CH_2OH$, —$NR_{11}S(O)_2NR_{11'}R_{11''}$ and $C(CH_3)_2OR_{11}$;

wherein $R_{11}$, $R_{11'}$ and $R_{11''}$ are independently selected from hydrogen, unsubstituted $C_{1-6}$ alkyl, unsubstituted $C_{2-6}$ alkenyl, unsubstituted $C_{2-6}$ alkynyl, unsubstituted aryl, unsubstituted alkylaryl, unsubstituted cycloalkyl and unsubstituted alkylcycloalkyl, unsubstituted heterocyclyl and unsubstituted alkyheterocylcyl;

and wherein $R_{11'''}$, is selected from hydrogen, unsubstituted $C_{1-6}$ alkyl, unsubstituted $C_{2-6}$ alkenyl, unsubstituted $C_{2-6}$ alkynyl and -Boc;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment of the compound according to the invention of general formula I and in relation to $R_1$ of any of the previous embodiments,
the cycloalkyl, aryl or heterocyclyl in $R_1$, if substituted, being substituted with one or more substituents selected from halogen, —$R_8$, —$OR_8$, —$NO_2$, —$NR_8R_{8'''}$, $NR_8C(O)R_{8'}$, —$NR_8S(O)_2R_{8'}$, —$S(O)_2NR_8R_{8'}$, —$NR_8C(O)NR_{8'}R_{8''}$, —$SR_8$, —$S(O)R_8$, —$S(O)_2R_8$, —CN, haloalkyl, haloalkoxy, —$C(O)OR_8$, —$C(O)NR_8R_{8'}$, —$OCH_2CH_2OH$, —$NR_8S(O)_2NR_{8'}R_{8''}$, and $C(CH_3)_2OR_8$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment of the compound according to the invention of general formula I and in relation to $R_1$ of any of the previous embodiments,
the cycloalkyl or non-aromatic heterocyclyl in $R_1$, if substituted, may be substituted substituted with

or =O;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment of the compound according to the invention of general formula I and in relation to $R_2$ of any of the previous embodiments,
the cycloalkyl, aryl or heterocyclyl in $R_2$, if substituted, is substituted with one or more substituents selected from halogen, —$R_9$, —$OR_9$, —$NO_2$, —$NR_9R_{9'''}$, $NR_9C(O)R_{9'}$, —$NR_9S(O)_2R_{9'}$, —$N(S(O)_2R_9)(S(O)_2R_{9'})$, —$S(O)_2NR_9R_{9'}$, —$NR_9C(O)NR_{9'}R_{9''}$, —$SR_9$, —$S(O)R_9$, $S(O)_2R_9$, —CN, haloalkyl, haloalkoxy, —$C(O)OR_9$, —$C(O)NR_9R_{9'}$, —$OCH_2CH_2OH$, —$NR_9S(O)_2NR_{9'}R_{9''}$ and $C(CH_3)_2OR_9$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment of the compound according to the invention of general formula I and in relation to $R_2$ of any of the previous embodiments,
the cycloalkyl or non-aromatic heterocyclyl in $R_2$, if substituted, may be substituted with

or =O;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment of the compound according to the invention of general formula I and in relation to $R_2$ of any of the previous embodiments,
the alkyl, alkylene or alkynyl in $R_2$, if substituted, is substituted with one or more substituents selected from —$OR_9$, halogen, —CN, haloalkyl, haloalkoxy, —$NR_9R_{9'''}$, —$SR_9$, —$S(O)R_9$, and —$S(O)_2R_9$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment of the compound according to the invention of general formula I and in relation to alkyls other than those defined in $R_1$ or $R_2$ of any of the previous embodiments,
the alkyl, alkylene or alkynyl, other than those defined in $R_1$ or $R_2$, if substituted, is substituted with one or more substituents selected from —$OR_{10}$, halogen, —CN, haloalkyl, haloalkoxy, —$NR_{10}R_{10'''}$, —$SR_{10}$, —$S(O)R_{10}$, and —$S(O)_2R_{10}$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment of the compound according to the invention of general formula I and in relation to aryl, heterocyclyl or cycloalkyl other than those defined in $R_1$ or $R_2$ of any of the previous embodiments, the aryl, heterocyclyl or cycloalkyl, also in alkylaryl, alkylcycloalkyl and alkylheterocyclyl, other than those defined in $R_1$ or $R_2$, if substituted, is substituted with one or more substituents selected from halogen, $-R_{11}$, $-OR_{11}$, $-NO_2$, $-NR_{11}R_{11'''}$, $NR_{11}C(O)R_{11'}$, $-NR_{11}S(O)_2R_{11'}$, $-S(O)_2NR_{11}R_{11'}$, $-NR_{11}C(O)NR_{11'}R_{11'''}$, $-SR_{11}$, $-S(O)R_{11}$, $S(O)_2R11$, $-CN$, haloalkyl, haloalkoxy, $-C(O)OR_{11}$, $-C(O)NR_{11}R_{11'}$, $-OCH_2CH_2OH$, $-NR_{11}S(O)_2NR_{11'}R_{11''}$ and $C(CH_3)_2OR_{11}$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In an embodiment of the invention in the compound of general formula I, the halogen is fluorine, chlorine, iodine or bromine.

In a most preferred embodiment of the invention in the compound of general formula I, the halogen is fluorine or chlorine.

In an embodiment of the invention in the compound of general formula I, the haloalkyl is $-CF3$.

In another embodiment of the invention in the compound of general formula I, the haloalkoxy is $-OCF3$.

As this invention is aimed at providing a compound or a chemically related series of compounds which act as dual ligands of the $\sigma_1$ receptor and the $\mu$-opiod receptor it is a very preferred embodiment in which the compounds are selected which act as dual ligands of the $\sigma_1$ receptor and the $\mu$-opiod receptor and especially compounds which have a binding expressed as $K_i$ which is preferably <1000 nM for both receptors, more preferably <500 nM, even more preferably <100 nM.

In the following the phrase "compound of the invention" is used. This is to be understood as any compound according to the invention as described above according to general formula I.

The compounds of the invention represented by the above described formula (I) may include enantiomers depending on the presence of chiral centres or isomers depending on the presence of multiple bonds (e.g. Z, E). The single isomers, enantiomers or diastereoisomers and mixtures thereof fall within the scope of the present invention.

In general the processes are described below in the experimental part. The starting materials are commercially available or can be prepared by conventional methods.

A preferred aspect of the invention is also a process for the production of a compound of formula I,

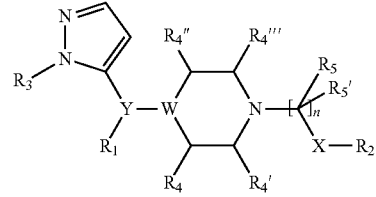

In a particular embodiment there is a process for the production of a compound of formula I,

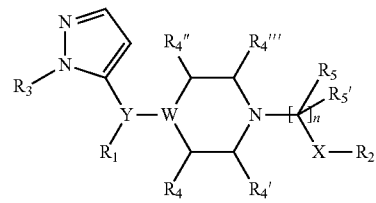

wherein n, X, $R_1$, $R_2$, $R_3$, $R_4$, $R_4'$, $R_4''$, $R_4'''$, $R_5$ and $R_5'$ are as defined in the description, and Y—W is $CR_Y$—N, said process comprises reducing a compound of formula VI

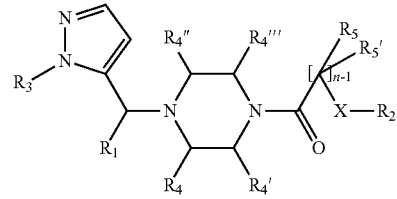

wherein n, X, $R_1$, $R_2$, $R_3$, $R_4$, $R_4'$, $R_4''$, $R_4'''$, $R_5$ and $R_5'$ are as defined above in the description.

In a particular embodiment there is a process for the production of a compound of formula I,

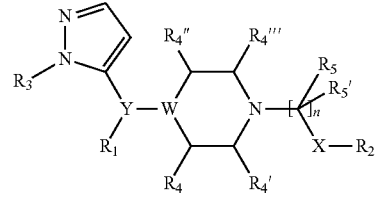

wherein n, X, $R_1$, $R_2$, $R_3$, $R_4$, $R_4'$, $R_4''$, $R_4'''$, $R_5$ and $R_5'$ are as defined above in the description, and Y—W is $CR_Y$—N, said process comprises reacting a compound of general formula IV,

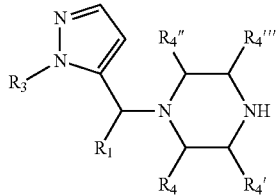
(IV)

wherein $R_1$, $R_3$, $R_4$, $R_{4'}$, $R_{4''}$, $R_{4'''}$ are as defined above in the description, with a suitable reagent of formula Va, Vb or Vc,

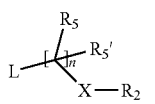
(Va)

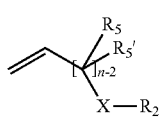
(Vb)

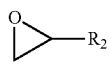
(Vc)

wherein n, X, $R_2$, $R_5$ and $R_{5'}$ are as defined in the description, and wherein L is a leaving group such as chloro, bromo, mesylate of tosylate.

In a particular embodiment there is a process for the production of a compound of formula I,

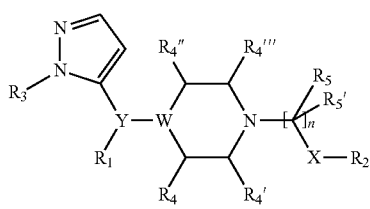
(I)

wherein n, X, $R_1$, $R_2$, $R_3$, $R_4$, $R_{4'}$, $R_{4''}$, $R_{4'''}$, $R_5$ and $R_{5'}$ are as defined in the description, and Y—W is $CR_Y$—N, said process comprises reacting a compound of general formula II

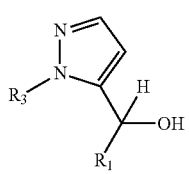
(II)

wherein $R_1$ and $R_3$ are as defined above in the description, is reacted first with methanesulfonyl chloride followed by an alkylation reaction with compounds of formula VII,

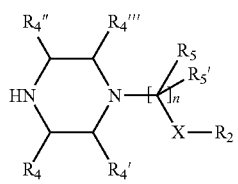
(VII)

wherein n, X, $R_2$, $R_4$, $R_{4'}$, $R_{4''}$, $R_{4'''}$, $R_5$ and $R_{5'}$ are as defined above in the description.

In a particular embodiment there is a process for the production of a compound of formula IV,

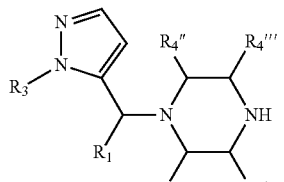
(IV)

wherein $R_1$, $R_3$, $R_4$, $R_{4'}$, $R_{4''}$ and $R_{4'''}$ are as defined above in the description, by treating a carbinol of general formula II

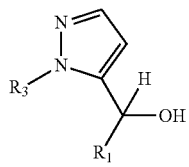
(II)

wherein $R_1$ and $R_3$ are as defined above in the description, with methanesulfonyl chloride and then treated with a protected piperazine of formula III,

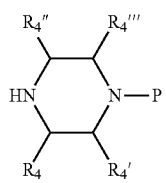
(III)

followed by deprotection of the piperazine group, wherein $R_4$, $R_{4'}$, $R_{4''}$ and $R_{4'''}$ are as defined above in the description, and P represents a suitable protecting group, preferably Boc (tert-butoxycarbonyl).

In a particular embodiment there is a process for the production of a compound of formula I,

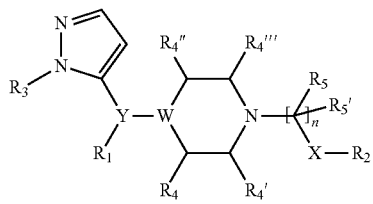
(I)

wherein n, X, $R_1$, $R_2$, $R_3$, $R_4$, $R_{4'}$, $R_{4''}$, $R_{4'''}$, $R_5$ and $R_{5'}$ are as defined above in the description, and Y—W is N—$CR_w$, by a reduction reaction of compounds of formula XII

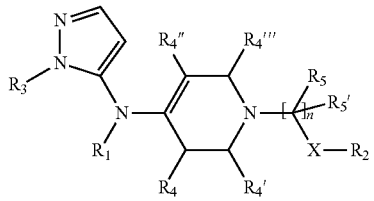
(XII)

wherein n, X, $R_1$, $R_2$, $R_3$, $R_4$, $R_{4'}$, $R_{4''}$, $R_{4'''}$, $R_5$ and $R_{5'}$ are as defined above in the description.

In a particular embodiment there is a process for the production of a compound of formula XII,

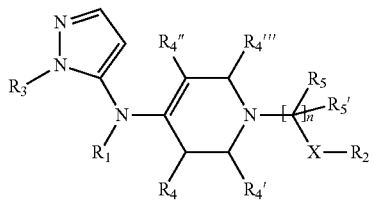
(XII)

wherein n, X, $R_1$, $R_2$, $R_3$, $R_4$, $R_{4'}$, $R_{4''}$, $R_{4'''}$, $R_5$ and $R_{5'}$ are as defined above in the description, by reacting a compound of formula X

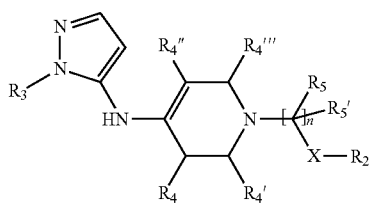
(X)

wherein n, X, $R_2$, $R_3$, $R_4$, $R_{4'}$, $R_{4''}$, $R_{4'''}$, $R_5$ and $R_{5'}$ are as defined above in the description, with an arylating agent of formula XI $R_1$—Z     (XI)

wherein $R_1$ is defined above in the description, and Z is halogen, preferably bromo, iodo or triflate.

In a particular embodiment there is a process for the production of a compound of formula X

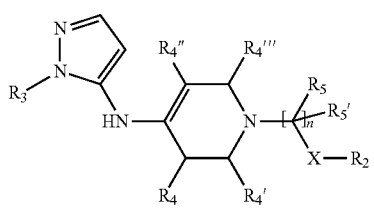
(X)

wherein n, X, $R_2$, $R_3$, $R_4$, $R_{4'}$, $R_{4''}$, $R_{4'''}$, $R_5$ and $R_{5'}$ are as defined above in the description, by reductive amination reaction between a compound of general formula VIII

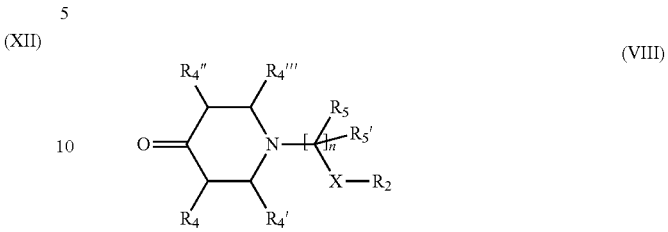
(VIII)

wherein n, X, $R_2$, $R_4$, $R_{4'}$, $R_{4''}$, $R_{4'''}$, $R_5$ and $R_{5'}$ are as defined above in the description, and a compound of general formula IX,

(IX)

wherein $R_3$ is as defined above in the description.

In a particular embodiment a compound of Formula (II),

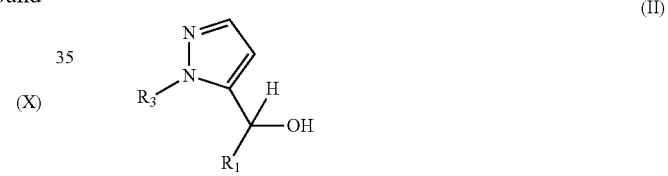
(II)

wherein $R_1$ and $R_3$ are as defined above in the description, is used for the preparation of compounds of Formula (I) wherein Y—W is $CR_Y$—N.

In another particular embodiment a compound of Formula (III), (III)

wherein $R_4$, $R_{4'}$, $R_{4''}$ and $R_{4'''}$ are as defined above in the description and P is a protecting group, is used for the preparation of compounds of Formula (I) wherein Y—W is $CR_Y$—N.

In a particular embodiment a compound of Formula (IV)

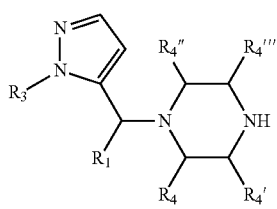

(IV)

wherein n, X, $R_1$, $R_3$, $R_4$, $R_{4'}$, $R_{4''}$ and $R_{4'''}$ are as defined above in the description, is used for the preparation of compounds of Formula (I) wherein Y—W is $CR_Y$—N.

In a particular embodiment a compound of Formula (Va)

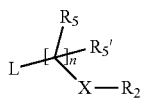

(Va)

wherein n, X, $R_2$, $R_5$ and $R_{5'}$ are as defined above in the description, and wherein L is a leaving group such as chloro, bromo, mesylate of tosylate, is used for the preparation of compounds of Formula (I) wherein Y—W is $CR_Y$—N.

In a particular embodiment a compound of Formula (Vb)

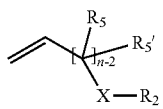

(Vb)

wherein n, X, $R_2$, $R_5$ and $R_{5'}$ are as defined above in the description, is used for the preparation of compounds of Formula (I) wherein Y—W is $CR_Y$—N.

In a particular embodiment a compound of Formula (Vc)

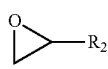

(Vc)

wherein $R_2$ is as defined above in the description, is used for the preparation of compounds of Formula (I) wherein Y—W is $CR_Y$—N.

In a particular embodiment a compound of Formula (Vd)

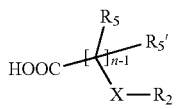

(Vd)

wherein n, $R_2$, $R_5$ and $R_{5'}$ are as defined above in the description, is used for the preparation of compounds of Formula (I) wherein Y—W is $CR_Y$—N.

In a particular embodiment a compound of Formula (VI)

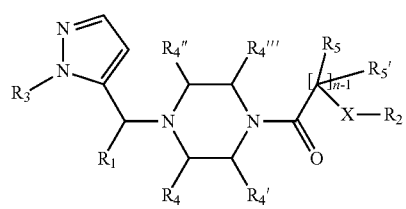

(VI)

wherein n, X, $R_1$, $R_2$, $R_3$, $R_4$, $R_{4'}$, $R_{4''}$, $R_{4'''}$, $R_5$ and $R_{5'}$ are as defined above in the description, is used for the preparation of compounds of Formula (I) wherein Y—W is $CR_Y$—N.

In a particular embodiment a compound of Formula (VII)

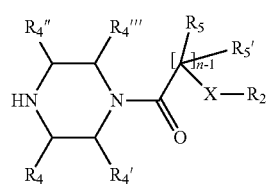

(VII)

wherein n, X, $R_2$, $R_4$, $R_{4'}$, $R_{4''}$, $R_{4'''}$, $R_5$ and $R_{5'}$ are as defined above in the description, is used for the preparation of compounds of Formula (I) wherein Y—W is $CR_Y$—N.

In a particular embodiment a compound of Formula (VIII)

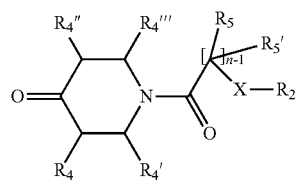

(VIII)

wherein n, X, $R_2$, $R_4$, $R_{4'}$, $R_{4''}$, $R_{4'''}$, $R_5$ and $R_{5'}$ are as defined above in the description, is used for the preparation of compounds of Formula (I) wherein Y—W is —N—CRw.

In a particular embodiment a compound of Formula (IX)

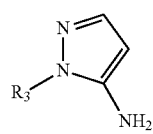

(IX)

wherein $R_3$ is as defined above in the description, is used for the preparation of compounds of Formula (I) wherein Y—W is —N—CRw.

In a particular embodiment a compound of Formula (X)

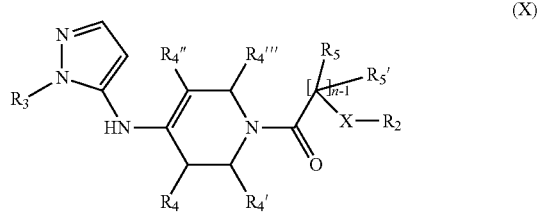

wherein n, X, $R_2$, $R_3$, $R_4$, $R_{4'}$, $R_{4''}$, $R_{4'''}$, $R_5$ and $R_{5'}$ are as defined above in the description, is used for the preparation of compounds of Formula (I) wherein Y—W is —N—CRw.

In a particular embodiment a compound of Formula (XI)

$$R_1—Z \qquad (XI)$$

wherein $R_1$ is as defined above in the description, and Z is halogen (preferably bromo or iodo) or triflate, is used for the preparation of compounds of Formula (I) wherein Y—W is —N—CRw.

In a particular embodiment a compound of Formula (XII)

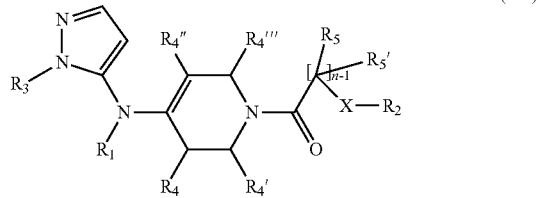

wherein n, X, $R_1$, $R_2$, $R_3$, $R_4$, $R_{4'}$, $R_{4''}$, $R_{4'''}$, $R_5$ and $R_{5'}$ are as defined above in the description, is used for the preparation of compounds of Formula (I) wherein Y—W is —N—CRw.

The obtained reaction products may, if desired, be purified by conventional methods, such as crystallisation and chromatography. Where the above described processes for the preparation of compounds of the invention give rise to mixtures of stereoisomers, these isomers may be separated by conventional techniques such as preparative chromatography. If there are chiral centers the compounds may be prepared in racemic form, or individual enantiomers may be prepared either by enantiospecific synthesis or by resolution.

One preferred pharmaceutically acceptable form of a compound of the invention is the crystalline form, including such form in pharmaceutical composition. In the case of salts and also solvates of the compounds of the invention the additional ionic and solvent moieties must also be non-toxic. The compounds of the invention may present different polymorphic forms, it is intended that the invention encompasses all such forms.

Another aspect of the invention refers to a pharmaceutical composition which comprises a compound according to the invention as described above according to general formula I (or of Formula Ia) or a pharmaceutically acceptable salt or steroisomer thereof, and a pharmaceutically acceptable carrier, adjuvant or vehicle. The present invention thus provides pharmaceutical compositions comprising a compound of this invention, or a pharmaceutically acceptable salt or stereoisomers thereof together with a pharmaceutically acceptable carrier, adjuvant, or vehicle, for administration to a patient.

Examples of pharmaceutical compositions include any solid (tablets, pills, capsules, granules etc.) or liquid (solutions, suspensions or emulsions) composition for oral, topical or parenteral administration.

In a preferred embodiment the pharmaceutical compositions are in oral form, either solid or liquid. Suitable dose forms for oral administration may be tablets, capsules, syrops or solutions and may contain conventional excipients known in the art such as binding agents, for example syrup, acacia, gelatin, sorbitol, tragacanth, or polyvinylpyrrolidone; fillers, for example lactose, sugar, maize starch, calcium phosphate, sorbitol or glycine; tabletting lubricants, for example magnesium stearate; disintegrants, for example starch, polyvinylpyrrolidone, sodium starch glycollate or microcrystalline cellulose; or pharmaceutically acceptable wetting agents such as sodium lauryl sulfate.

The solid oral compositions may be prepared by conventional methods of blending, filling or tabletting. Repeated blending operations may be used to distribute the active agent throughout those compositions employing large quantities of fillers. Such operations are conventional in the art. The tablets may for example be prepared by wet or dry granulation and optionally coated according to methods well known in normal pharmaceutical practice, in particular with an enteric coating.

The pharmaceutical compositions may also be adapted for parenteral administration, such as sterile solutions, suspensions or lyophilized products in the apropriate unit dosage form. Adequate excipients can be used, such as bulking agents, buffering agents or surfactants.

The mentioned formulations will be prepared using standard methods such as those described or referred to in the Spanish and US Pharmacopoeias and similar reference texts.

Administration of the compounds or compositions of the present invention may be by any suitable method, such as intravenous infusion, oral preparations, and intraperitoneal and intravenous administration. Oral administration is preferred because of the convenience for the patient and the chronic character of the diseases to be treated.

Generally an effective administered amount of a compound of the invention will depend on the relative efficacy of the compound chosen, the severity of the disorder being treated and the weight of the sufferer. However, active compounds will typically be administered once or more times a day for example 1, 2, 3 or 4 times daily, with typical total daily doses in the range of from 0.1 to 1000 mg/kg/day.

The compounds and compositions of this invention may be used with other drugs to provide a combination therapy. The other drugs may form part of the same composition, or be provided as a separate composition for administration at the same time or at different time.

Another aspect of the invention refers to the use of a compound of the invention or a pharmaceutically acceptable salt or isomer thereof in the manufacture of a medicament.

Another aspect of the invention refers to a compound of the invention according as described above according to general formula I (or of Formula (Ia)), or a pharmaceutically acceptable salt or isomer thereof, for use as a medicament for the treatment of pain. Preferably the pain is medium to severe pain, visceral pain, chronic pain, cancer pain, migraine, inflammatory pain, acute pain or neuropathic pain, allodynia or hyperalgesia. This may include mechanical allodynia or thermal hyperalgesia.

Another aspect of the invention refers to the use of a compound of the invention in the manufacture of a medicament for the treatment or prophylaxis of pain.

In a preferred embodiment the pain is selected from medium to severe pain, visceral pain, chronic pain, cancer pain, migraine, inflammatory pain, acute pain or neuropathic pain, allodynia or hyperalgesia, also preferably including mechanical allodynia or thermal hyperalgesia.

Another aspect of this invention relates to a method of treating or preventing pain which method comprises administering to a patient in need of such a treatment a therapeutically effective amount of a compound as above defined or a pharmaceutical composition thereof. Among the pain syndromes that can be treated are medium to severe pain, visceral pain, chronic pain, cancer pain, migraine, inflammatory pain, acute pain or neuropathic pain, allodynia or hyperalgesia, whereas this could also include mechanical allodynia or thermal hyperalgesia.

The present invention is illustrated below with the aid of examples. These illustrations are given solely by way of example and do not limit the general spirit of the present invention.

EXAMPLES

General Experimental Part (Methods and Equipment of the Synthesis and Analysis

A 2-step process is described in Scheme 1 for the preparation of compounds of general formula I, wherein $R_1$, $R_2$, $R_3$, $R_4$, $R_{4'}$, $R_{4''}$, $R_{4'''}$, $R_5$, $R_{5'}$, and X have the meanings defined above, and Y—W is $CR_Y$—N.

Scheme 1
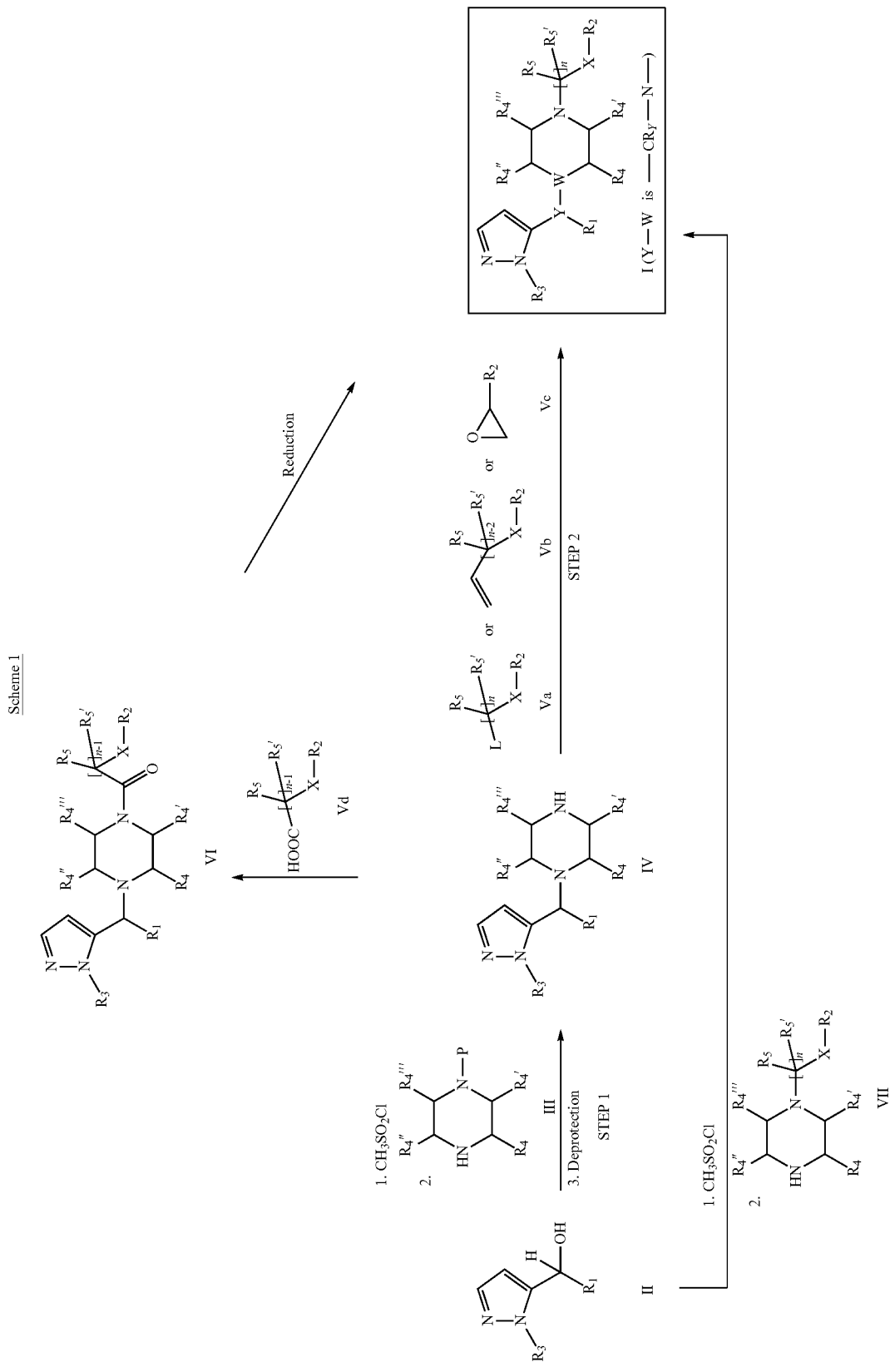

Where L is a leaving group such as chloro, bromo, mesylate or tosylate, preferably selected from chloro, bromo, mesylate and tosylate.

This process is carried out as described below:

Step 1: A compound of formula IV is prepared from a carbinol of general formula II by a 3-step procedure in which no intermediate is purified. Thus treating a carbinol of general formula II with methanesulfonyl chloride in a suitable solvent such as dichloromethane, in the presence of an organic base such as triethylamine or diisopropylethylamine, preferably triethylamine, at a suitable temperature comprised between 0° C. and room temperature, preferably at 0° C. gives a mesylate intermediate, which is treated with a protected piperazine of formula III, wherein P represents a suitable protecting group, preferably Boc (tert-butoxycarbonyl). The alkylation reaction is carried out in a suitable solvent, such as acetonitrile, dichloromethane, 1,4-dioxane or dimethylformamide, preferably in acetonitrile; in the presence of an inorganic base such as $K_2CO_3$ or $Cs_2CO_3$, or an organic base such as triethylamine or diisopropylethylamine, preferably $K_2CO_3$; at a suitable temperature comprised between room temperature and the reflux temperature, preferably heating, or alternatively, the reactions can be carried out in a microwave reactor. Additionally, an activating agent such as NaI or KI can be used.

Finally, the compounds of formula IV are obtained by deprotection of the piperazine group. If the protecting group is Boc, the deprotection is carried out in the presence of an inorganic acid such as HCl or TFA, preferably HCl, in a suitable solvent, such as AcOEt, ethanol, methanol or diethyl ether, at a suitable temperature comprised between room temperature and the reflux temperature, preferably at room temperature.

Step 2. The compounds of general formula I, wherein Y—W is $CR_Y$—N, are prepared by reacting a compound of general formula IV with a suitable reagent of formula Va-c, using different conditions depending on the reagent nature. Thus:

The alkylation reaction between a compound of formula IV (or a suitable salt such as trifluoroacetate or hydrochloride) and a compound of formula Va is carried out in a suitable solvent, such as ethanol, acetonitrile, dichloromethane, 1,4-dioxane or dimethylformamide, preferably in ethanol; in the presence of an inorganic base such as $K_2CO_3$ or $Cs_2CO_3$, or an organic base such as triethylamine or diisopropylethylamine, at a suitable temperature comprised between room temperature and the reflux temperature, preferably in a microwave reactor. Additionally, an activating agent such as NaI or KI can be used.

The condensation reaction between a compound of general formula IV and a compound of formula Vb is carried out in a suitable solvent, such as isopropanol, n-butanol or 2-methoxyethanol, optionally in the presence of an organic base such as triethylamine or diisopropylethylamine, at a suitable temperature comprised between room temperature and the reflux temperature, preferably heating, or alternatively, the reactions can be carried out in a microwave reactor.

The compounds of general formula I, wherein X is —CH(OH)— and $R_5$ and $R_{5'}$ are hydrogen, are prepared through opening of a epoxide of formula Vc, by a compound of general formula IV. This reaction is carried out in a suitable solvent, such as toluene, at a suitable temperature comprised between room temperature and the reflux temperature, preferably at reflux temperature.

Alternatively, the transformation of a compound of formula IV to a compound of formula I, wherein Y—W is $CR_Y$—N, can be effected in a two step procedure, involving acylation of IV with a compound of formula Vd to give a compound of formula VI, which is then reduced. The acylation reaction can be carried out using amide coupling conditions, such as EDC/HOBt/DIPEA in a suitable solvent, such as DMF, at a suitable temperature, preferably room temperature. The reduction reaction can be effected with a reducing agent such as aluminium hydride, in a suitable solvent such as tetrahydrofurane, at a suitable temperature comprised between 0° C. and room temperature, preferably at 0° C.

The process described by steps 1 to 2 represents the most general route for the preparation of compounds of formula I. Additionally, compounds of general formula I, wherein Y—W is $CR_Y$—N, can be obtained in a single step procedure, involving preparation of a mesylate derivative of carbinol II, in the conditions described in step 1, and subsequent alkylation reaction with compounds of formula VII, in the conditions also described in step 1.

A 3-step process is described in Scheme 2 for the preparation of compounds of general formula I, wherein $R_1$, $R_2$, $R_3$, $R_4$, $R_{4'}$, $R_{4''}$, $R_{4'''}$, $R_5$, $R_{5'}$, and X have the meanings as defined above, and Y—W is N—$CR_w$.

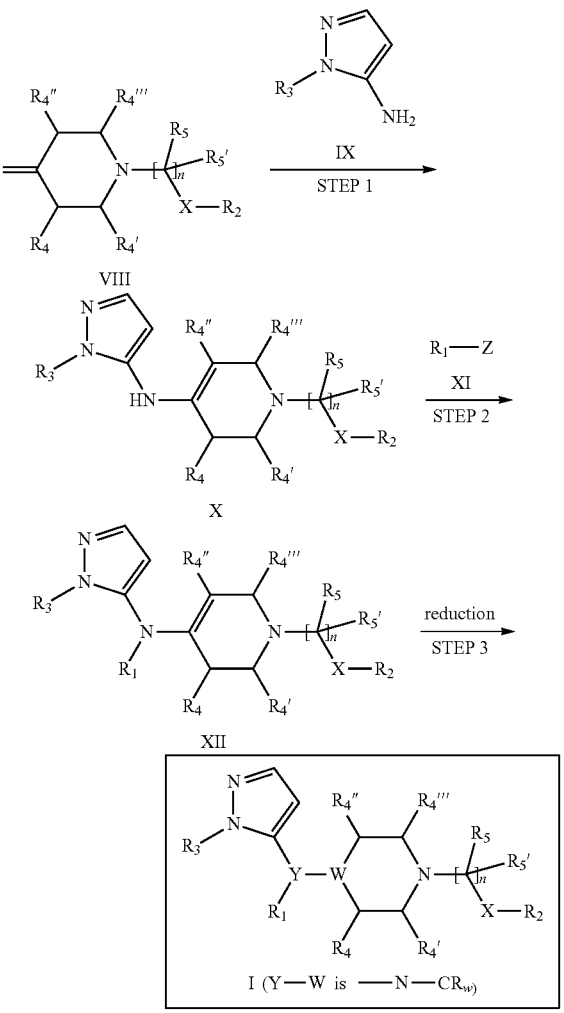

Scheme 2

Where Z is halogen (preferably bromo or iodo) or triflate.

This process is carried out as described below:

Step 1: A compound of formula X is prepared by reductive amination reaction between a compound of general formula VIII and a compound of general formula IX in the presence of a reductive reagent, preferably NaBH$_4$, in a suitable solvent, such as methanol, at a suitable temperature comprised between room temperature and the reflux temperature, preferably at the reflux temperature.

Step 2: A compound of formula XII is prepared by reacting a compound of formula X with an arylating agent of formula XI. This arylation reaction is carried out under catalytic conditions using a palladium or copper catalyst, preferably palladium catalysts such as tris(dibenzylideneacetone)dipalladium or palladium diacetate; in the presence of a suitable ligand such as 4,5-bis(diphenylphosphino)-9,9-dimethylxanthene (Xantphos) or BINAP; and a suitable base such as cessium carbonate or sodium tert-butoxide; in a suitable solvent such as 1,4-dioxane or toluene, and at a suitable temperature, preferably heating at the reflux temperature or in a microwave reactor.

Step 3: The compounds of general formula I, wherein Y—W is N—CR$_w$. are prepared by a reduction reaction of compounds of formula XII. The reduction reaction is preferably carried out by hydrogenation under hydrogen atmosphere and metal catalysis, preferably by use of palladium over charcoal as catalyst in a suitable solvent such as methanol or ethanol.

Alternatively the sequence described in Scheme 2 can also be carried out by reaction of a compound of formula IX with a conveniently protected 4-ketopiperidine, which can be converted to a compound of formula I following similar procedures to those described in Scheme I.

Moreover, certain compounds of the present invention can also be obtained starting from other compounds of formula (I) by appropriate conversion reactions of functional groups, in one or several steps, using well-known reactions in organic chemistry under standard experimental conditions. As a way of example, some of these conversions include the demethylation of a methoxy group to yield an hydroxy group, the reduction of a nitro group to yield an amino group, the acylation of an amino group to yield an acylamino group, the sulfonylation of an amino group to yield a sulfonylamino derivative and the reduction of a keto group to an hydroxy group.

INTERMEDIATES AND EXAMPLES

The following abbreviations are used in the examples:
ACN: acetonitrile
DCM: dichloromethane
DIPEA: diisopropylethylamine
DMF: dimethylformamide
EDC: N-(3-dimethylaminopropyl)-N'-ethylcarbodiimide
EtOH: ethanol
EX: example
h: hour/s
HOBt: Hydroxybenzotriazole
HPLC: high performance liquid chromatography
INT: intermediate
MeOH: methanol
MS: mass spectrometry
Min.: minutes
Ret.: retention
r.t.: room temperature
TFA: trifluoroacetic acid
THF: tetrahydrofuran The following method was used to determine the HPLC-MS spectra:
A: Column: XBridge C18 4.6×50 mm 2.5 µm; flow rate: 2 mL/min; temperature: 35° C., A: NH$_4$HCO$_3$ 10 mM; B: ACN; gradient: 0.3 min in 98% A, 98% A to 5% A in 4 min, 1.5 min in 5% A, 5% A to 98% A in 0.5 min, 1 min in 98% A.
B: Column Acquity BEH C18 2.1×50 mm, 1.7 µm; flow rate 0.61 mL/min; temperature: 35° C., A: NH$_4$HCO$_3$ 10 mM; B: ACN; gradient: 0.3 min in 98% A, 98% A to 5% A in 2.52 min, 1.02 min in 5% A, 5% A to 98% A in 0.34 min, 0.57 min in 98% A.

Intermediate 1A (1-Methyl-1H-pyrazol-5-yl)(pyridin-2-yl)methanol

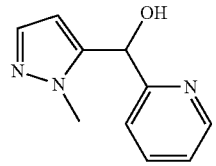

A solution of N-methylpyrazol (1.41 mL, 17.1 mmol) in anhydrous THF (40 mL) was cooled to −78° C. using a dry ice/acetone bath. After addition of buthyllithium (8.75 mL, 2M in cyclohexanes, 17.48 mmol), the reaction mixture was stirred at −78° C. for 80 min. A solution of 2-pyridine carboxaldehyde (1.87 g, 17.48 mmol) in anhydrous THF (25 mL) was added dropwise and the reaction mixture was stirred for 4 h, keeping the temperature between −40° C. and −20° C. Then, aqueous NH$_4$Cl (10 mL) was added slowly and the insoluble salts were filtered and washed with THF. The filtrate was concentrated off and the residue was partioned between AcOEt and brine. The aqueous layer was extracted twice again with EtOAc and the combined organic layers were washed with water, dried over Na$_2$SO$_4$, filtered and concentrated. The crude residue was purified by flash chromatography on silica gel, gradient chloroform to MeOH from (100:0) to (95:5) to give the title compound as a brown oil (1.8 g, yield 54%).

HPLC-MS (Method A): Ret, 0.96 min; ESI$^+$-MS m/z, 190.1 (M+1).

This method was used for the preparation of intermediates 1B-N using suitable starting materials:

| INT | Structure | Chemical name | Method | Ret (min) | MS (M + H) |
|---|---|---|---|---|---|
| 1B | 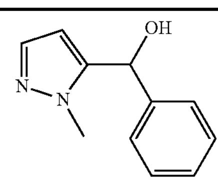 | (1-methyl-1H-pyrazol-5-yl)(phenyl)methanol | B | 1.23 | 189.1 |

| INT | Structure | Chemical name | Method | Ret (min) | MS (M + H) |
|---|---|---|---|---|---|
| 1C | 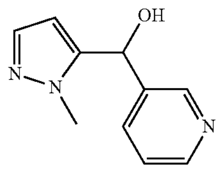 | (1-methyl-1H-pyrazol-5-yl)(pyridin-3-yl)methanol | B | 0.82 | 190.1 |
| 1D | 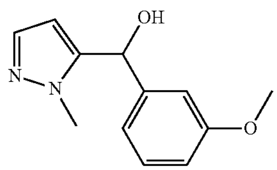 [SMILES: COc1cccc(C(O)c2ccnn2C)c1] | (3-methoxyphenyl)(1-methyl-1H-pyrazol-5-yl)methanol | B | 1.24 | 219.1 |
| 1E | | (2-methoxyphenyl)(1-methyl-1H-pyrazol-5-yl)methanol | A | 1.25 | 219.1 |
| 1F | | (4-methoxyphenyl)(1-methyl-1H-pyrazol-5-yl)methanol | B | 1.23 | 219.1 |
| 1E | | (1-methyl-1H-pyrazol-5-yl)(6-(trifluoromethyl)pyridin-2-yl)methanol | B | 1.36 | 258.2 |
| 1F | | (1-methyl-1H-pyrazol-5-yl)(6-(trifluoromethyl)pyridin-3-yl)methanol | B | 1.30 | 258.2 |
| 1G | 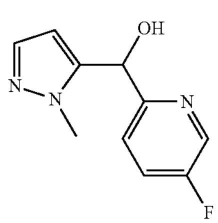 | (5-fluoropyridin-2-yl)(1-methyl-1H-pyrazol-5-yl)methanol | B | 0.99 | 208.1 |

-continued

| INT | Structure | Chemical name | Method | Ret (min) | MS (M + H) |
|---|---|---|---|---|---|
| 1H | 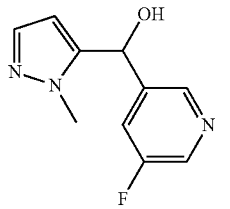 | (5-fluoropyridin-3-yl)(1-methyl-1H-pyrazol-5-yl)methanol | B | 0.95 | 208.1 |
| 1I | 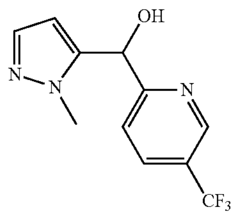 [SMILES: Cn1nccc1C(O)c1ccc(C(F)(F)F)cn1] | (1-methyl-1H-pyrazol-5-yl)(5-(trifluoromethyl)pyridin-2-yl)methanol | B | 1.33 | 258 |
| 1J | 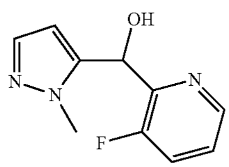 | (3-fluoropyridin-2-yl)(1-methyl-1H-pyrazol-5-yl)methanol | B | 0.96 | 208.1 |
| 1K | 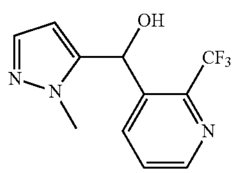 [SMILES: Cn1nccc1C(O)c1cccnc1C(F)(F)F] | (1-methyl-1H-pyrazol-5-yl)(2-(trifluoromethyl)pyridin-3-yl)methanol | B | 1.15 | 258 |
| 1L | 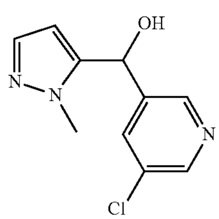 | (5-chloropyridin-3-yl)(1-methyl-1H-pyrazol-5-yl)methanol | B | 1.17 | 224 |
| 1M | 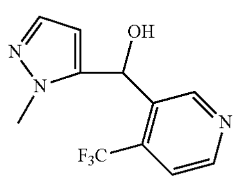 [SMILES: Cn1nccc1C(O)c1cnccc1C(F)(F)F] | (1-methyl-1H-pyrazol-5-yl)(4-(trifluoromethyl)pyridin-3-yl)methanol | B | 1.16 | 258 |
| 1N | 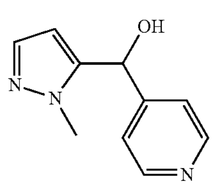 | (1-methyl-1H-pyrazol-5-yl)(pyridin-4-yl)methanol | B | 0.79 | 190 |

Intermediate 2A

1-((1-Methyl-1H-pyrazol-5-yl)(phenyl)methyl)piperazine hydrochloride

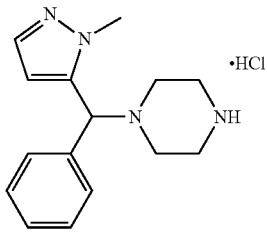 [SMILES: Cn1nccc1C(c1ccccc1)N1CCNCC1 ; Cl]

a) (1-Methyl-1H-pyrazol-5-yl)(phenyl)methyl methanesulfonate

Et$_3$N (2.96 mL, 21.25 mmol) was added to a solution of (1-methyl-1H-pyrazol-5-yl)(phenyl)methanol (intermediate 1B, 2 g, 10.62 mmol) in DCM (200 mL). The solution was cooled to 0° C. and stirred for 10 min and then, methanesulfonyl chloride (1.64 mL, 21.25 mmol) was added and the reaction mixture was stirred at 0° C. After 2 h the reaction mixture was allowed to warm to r.t. and diluted with DCM (10 mL). The organic layer was washed with water, dried over Na$_2$SO$_4$, filtered and evaporated to dryness to afford the title compound as a colorless oil (2.8 g, yield 99%) that was used in the next step without further purification.

b) tert-Butyl 4-((1-methyl-1H-pyrazol-5-yl)(phenyl) methyl)piperazine-1-carboxylate (1-Methyl-1H-pyrazol-5-yl)(phenyl)methyl methanesulfonate (obtained in step a, 2.8 g, 10.63 mmol) was added to a solution of tert-butyl piperazine-1-carboxylate (1.65 g, 8.86 mmol) and K$_2$CO$_3$ (2.44 g, 17.71 mmol) in ACN (85 mL). The reaction mixture was stirred at 80° C. overnight and then was cooled down to r.t. and poured into cold water. AcOEt (100 mL) was added and the phases were separated. The organic layer was dried over Na$_2$SO$_4$, filtered and concentrated. The crude residue was purified by flash chromatography on silica gel, eluents DCM:MeOH (85:15) to give the title compound as a yellow oil (1.88 g, yield 59%).

HPLC-MS (Method B): Ret, 2.09 min; ESI$^+$-MS m/z, 357.3 (M+1).

c) Title Compound

HCl (2 M solution in diethyl ether, 8.83 mL, 17.67 mmol) was added to a solution of tert-butyl 4-((1-methyl-1H-pyrazol-5-yl)(phenyl)methyl)piperazine-1-carboxylate (obtained in the previous step, 1.26 g, 3.53 mmol) in AcOEt (15 mL) and ethanol (15 mL). The reaction mixture was stirred at r.t. for 5 h and then the solvents were evaporated to dryness to give the title compound as a brown solid (1.20 g, quantitative yield).

HPLC-MS (Method B): Ret, 1.13 min; ESI$^+$-MS m/z, 257.2 (M+1).

This method was used for the preparation of intermediate 2B using intermediate 1G as starting material:

| INT | Structure | Chemical name | Method | Ret (min) | MS (M + H) |
|---|---|---|---|---|---|
| 2B | 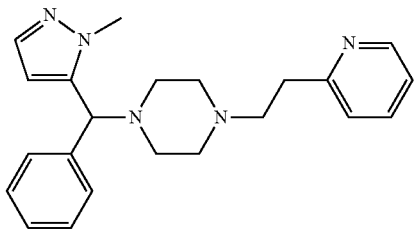 [SMILES: Cn1nccc1C(c1ccccc1)N1CCN(CCc2ccccn2)CC1] | 1-((5-fluoropyridin-2-yl)(1-methyl-1H-pyrazol-5-yl)methyl)piperazine | B | 0.95 | 276 |

Example 1

1-((1-Methyl-1H-pyrazol-5-yl)(phenyl)methyl)-4-(2-(pyridin-2-yl)ethyl)piperazine A solution of 1-(2-(pyridin-2-yl)ethyl)piperazine (203 µL, 1.07 mmol), (1-methyl-1H-pyrazol-5-yl)(phenyl)methyl methanesulfonate (compound obtained in the synthesis of intermediate 2A, step a, 269 mg, 0.89 mmol) and K$_2$CO$_3$ (246 mg, 1.78 mmol) in ACN (10 mL) was stirred at 80° C. overnight. The reaction mixture was poured into cold water, AcOEt (5 mL) was added and the organic layer was separated, dried over Na$_2$SO$_4$, filtered and concentrated. The crude residue was purified by flash chromatography on silica gel, gradient DCM to MeOH from (100:0) to (93:7) to give the title compound as a yellow oil (132 mg, yield 19%).

HPLC-MS (Method B): Ret, 1.6 min; ESI$^+$-MS m/z, 362.2 (M+1).

A similar method was used for the preparation of examples 2-20, using the methanesulfonate derivatives of intermediates 1 (prepared as described in the synthesis of intermediate 2A, step a) as starting materials, and suitable substituted piperazines:

| EX | Structure | Chemical name | Method | Ret (min) | MS (M + H) |
|---|---|---|---|---|---|
| 2 | 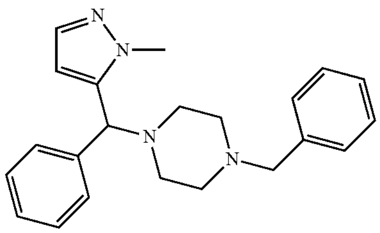 [SMILES: Cn1nccc1C(c1ccccc1)N1CCN(Cc2ccccc2)CC1] | 1-benzyl-4-((1-methyl-1H-pyrazol-5-yl)(phenyl)methyl)piperazine | B | 2.10 | 347.2 |
| 3 | 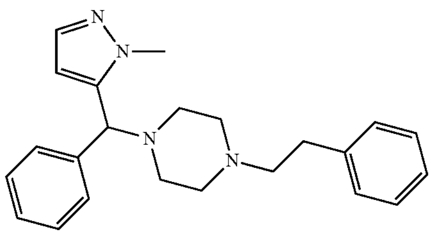 [SMILES: Cn1nccc1C(c1ccccc1)N1CCN(CCc2ccccc2)CC1] | 1-((1-methyl-1H-pyrazol-5-yl)(phenyl)methyl)-4-phenethylpiperazine | B | 2.11 | 361.3 |
| 4 | 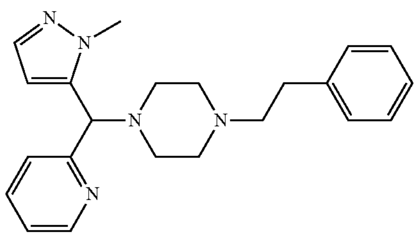 [SMILES: Cn1nccc1C(c1ccccn1)N1CCN(CCc2ccccc2)CC1] | 1-((1-methyl-1H-pyrazol-5-yl)(pyridin-2-yl)methyl)-4-phenethylpiperazine | B | 1.77 | 362.2 |
| 5 | 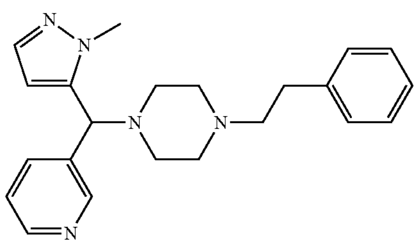 | 1-((1-methyl-1H-pyrazol-5-yl)(pyridin-3-yl)methyl)-4-phenethylpiperazine | B | 1.77 | 362.2 |
| 6 | 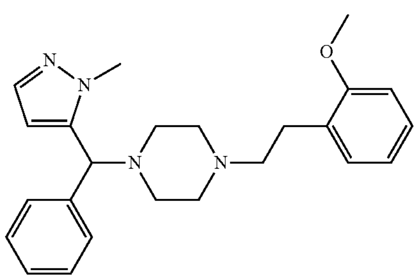 [SMILES: COc1ccccc1CCN1CCN(C(c2ccccc2)c2ccnn2C)CC1] | 1-(2-methoxyphenethyl)-4-((1-methyl-1H-pyrazol-5-yl)(phenyl)methyl)piperazine | B | 2.16 | 391.3 |
| 7 | 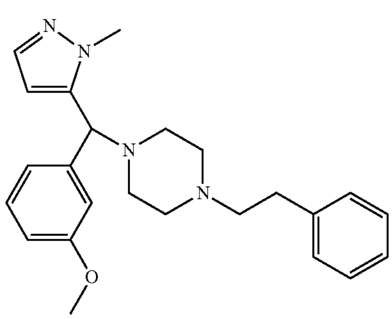 [SMILES: COc1cccc(C(c2ccnn2C)N2CCN(CCc3ccccc3)CC2)c1] | 1-((3-methoxyphenyl)(1-methyl-1H-pyrazol-5-yl)methyl)-4-phenethylpiperazine | B | 2.09 | 391.3 |

| EX | Structure | Chemical name | Method | Ret (min) | MS (M + H) |
|---|---|---|---|---|---|
| 8 | 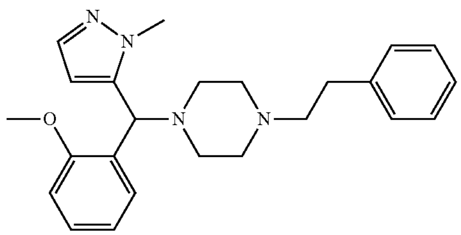 [SMILES: COc1ccccc1C(c1ccnn1C)N1CCN(CCc2ccccc2)CC1] | 1-((2-methoxyphenyl)(1-methyl-1H-pyrazol-5-yl)methyl)-4-phenethylpiperazine | B | 2.17 | 391.3 |
| 9 | 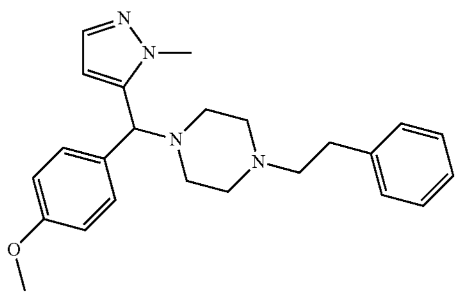 [SMILES: COc1ccc(C(c2ccnn2C)N2CCN(CCc3ccccc3)CC2)cc1] | 1-((4-methoxyphenyl)(1-methyl-1H-pyrazol-5-yl)methyl)-4-phenethylpiperazine | B | 2.07 | 391.3 |
| 10 | 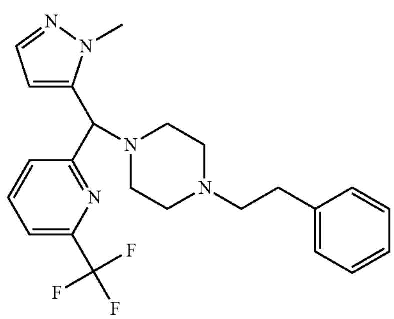 [SMILES: Cn1nccc1C(c1cccc(C(F)(F)F)n1)N1CCN(CCc2ccccc2)CC1] | 1-((1-methyl-1H-pyrazol-5-yl)(6-(trifluoromethyl)pyridin-2-yl)methyl)-4-phenethylpiperazine | B | 2.15 | 430.3 |
| 11 | 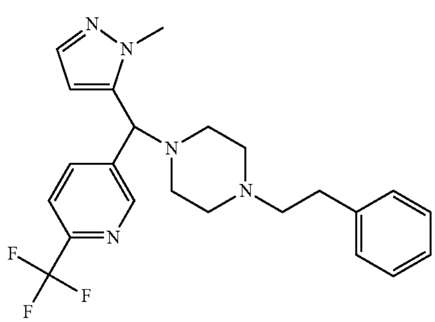 [SMILES: Cn1nccc1C(c1ccc(C(F)(F)F)nc1)N1CCN(CCc2ccccc2)CC1] | 1-((1-methyl-1H-pyrazol-5-yl)(6-(trifluoromethyl)pyridin-3-yl)methyl)-4-phenethylpiperazine | B | 2.11 | 430.4 |
| 12 | 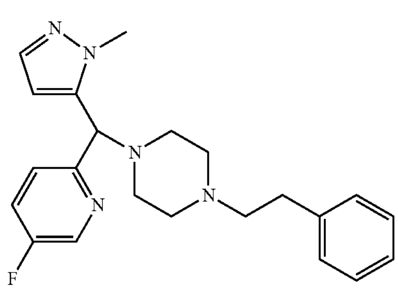 [SMILES: Cn1nccc1C(c1ccc(F)cn1)N1CCN(CCc2ccccc2)CC1] | 1-((5-fluoropyridin-2-yl)(1-methyl-1H-pyrazol-5-yl)methyl)-4-phenethylpiperazine | B | 1.86 | 380.4 |

-continued

| EX | Structure | Chemical name | Method | Ret (min) | MS (M + H) |
|---|---|---|---|---|---|
| 13 | 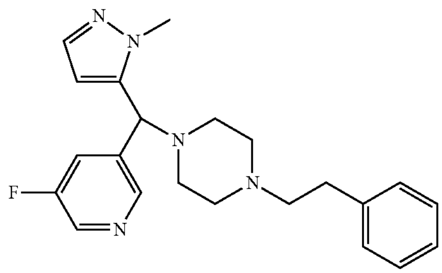 [SMILES: Cn1nccc1C(c1cncc(F)c1)N1CCN(CCc2ccccc2)CC1] | 1-((5-fluoropyridin-3-yl)(1-methyl-1H-pyrazol-5-yl)methyl)-4-phenethylpiperazine | B | 1.83 | 380.3 |
| 14 | 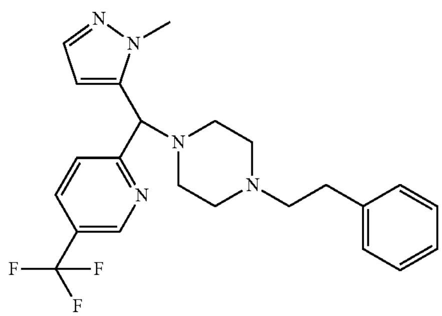 [SMILES: Cn1nccc1C(c1ccc(C(F)(F)F)cn1)N1CCN(CCc2ccccc2)CC1] | 1-((1-methyl-1H-pyrazol-5-yl)(5-(trifluoromethyl)pyridin-2-yl)methyl)-4-phenethylpiperazine | B | 2.11 | 430.2 |
| 15 | 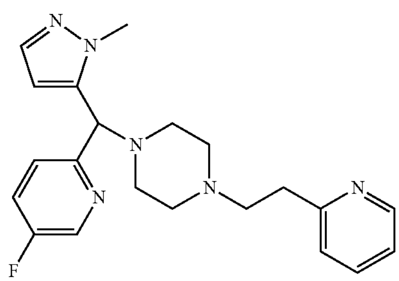 [SMILES: Cn1nccc1C(c1ccc(F)cn1)N1CCN(CCc2ccccn2)CC1] | 1-((5-fluoropyridin-2-yl)(1-methyl-1H-pyrazol-5-yl)methyl)-4-(2-(pyridin-2-yl)ethyl)piperazine | B | 1.38 | 381.3 |
| 16 | 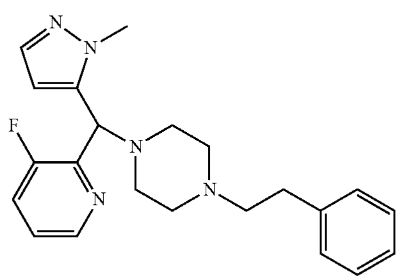 [SMILES: Cn1nccc1C(c1ncccc1F)N1CCN(CCc2ccccc2)CC1] | 1-((3-fluoropyridin-2-yl)(1-methyl-1H-pyrazol-5-yl)methyl)-4-phenethylpiperazine | B | 1.79 | 380.2 |
| 17 | 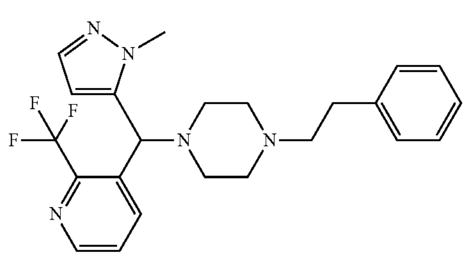 [SMILES: Cn1nccc1C(c1cccnc1C(F)(F)F)N1CCN(CCc2ccccc2)CC1] | 1-((1-methyl-1H-pyrazol-5-yl)(2-(trifluoromethyl)pyridin-3-yl)methyl)-4-phenethylpiperazine | B | 2.08 | 430.2 |

| EX | Structure | Chemical name | Method | Ret (min) | MS (M + H) |
|---|---|---|---|---|---|
| 18 | 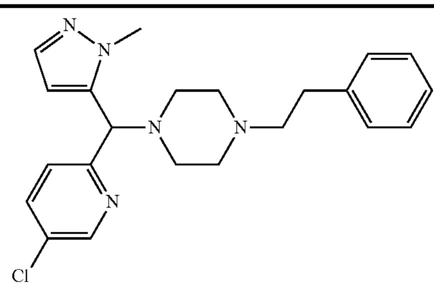 | 1-((5-chloropyridin-2-yl)(1-methyl-1H-pyrazol-5-yl)methyl)-4-phenethylpiperazine | B | 2.03 | 396.1 |
| 19 | 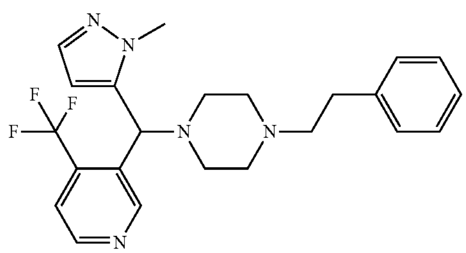 [SMILES: Cn1nccc1C(c1cnccc1C(F)(F)F)N1CCN(CCc2ccccc2)CC1] | 1-((1-methyl-1H-pyrazol-5-yl)(4-(trifluoromethyl)pyridin-3-yl)methyl)-4-phenethylpiperazine | B | 2.02 | 430.1 |
| 20 | 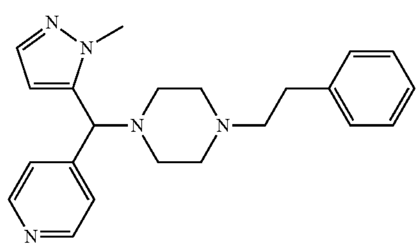 | 1-((1-methyl-1H-pyrazol-5-yl)(pyridin-4-yl)methyl)-4-phenethylpiperazine | B | 1.66 | 362.1 |

Example 21

1-(3-Methoxyphenethyl)-4-((1-methyl-1H-pyrazol-5-yl)(phenyl)methyl)piperazine

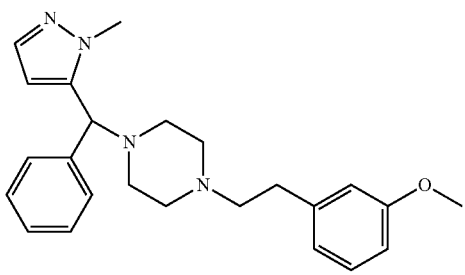 [SMILES: COc1cccc(CCN2CCN(C(c3ccccc3)c3ccnn3C)CC2)c1]

A microwave vial was charged with 1-((1-methyl-1H-pyrazol-5-yl)(phenyl)methyl)piperazine hydrochloride (intermediate 2A, 50 mg, 0.152 mmol) in ethanol (5 mL) and triethylamine was added dropwise (63.5 μL, 0.456 mmol). 1-(2-Bromoethyl)-3-methoxybenzene (47.6 μL, 0.304 mmol) was added, the vial was sealed and subjected to microwave irradiating conditions for 1 h at 120° C. and then cooled. The solvents were concentrated in vacuo and the residue was partioned between DCM and saturated solution of $NaHCO_3$. The organic layer was dried over $Na_2SO_4$, filtered and concentrated. The crude residue was purified by flash chromatography on silica gel, gradient DCM:MeOH from (100:0) to (80:20) to give the title compound as a colorless oil (17 mg, yield 29%).

HPLC-MS (Method B): Ret, 2.07 min; ESI$^+$-MS m/z, 391.3 (M+1).

A similar method was used for the preparation of examples 22-27, using intermediates 2A and 2B as starting materials and suitable alkylating agents:

| EX | Structure | Chemical name | Method | Ret (min) | MS (M + H) |
|---|---|---|---|---|---|
| 22 | 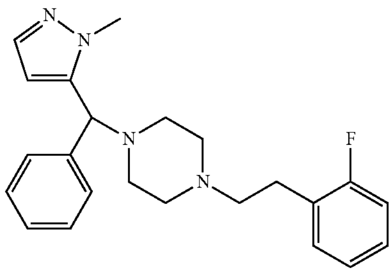 [SMILES: Cn1nccc1C(c1ccccc1)N1CCN(CCc2ccccc2F)CC1] | 1-(2-fluorophenethyl)-4-((1-methyl-1H-pyrazol-5-yl)(phenyl)methyl)piperazine | B | 2.17 | 379.3 |
| 23 | 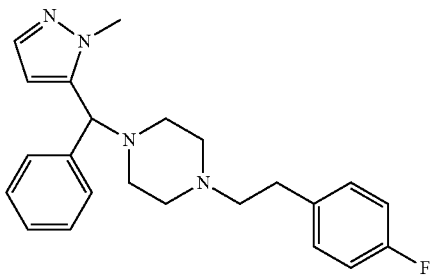 [SMILES: Cn1nccc1C(c1ccccc1)N1CCN(CCc2ccc(F)cc2)CC1] | 1-(4-fluorophenethyl)-4-((1-methyl-1H-pyrazol-5-yl)(phenyl)methyl)piperazine | B | 2.13 | 379.3 |
| 24 | 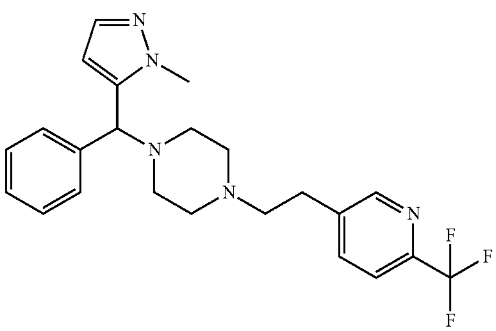 [SMILES: Cn1nccc1C(c1ccccc1)N1CCN(CCc2ccc(C(F)(F)F)nc2)CC1] | 1-((1-methyl-1H-pyrazol-5-yl)(phenyl)methyl)-4-(2-(6-(trifluoromethyl)pyridin-3-yl)ethyl)piperazine | B | 2.01 | 430.4 |
| 25 | 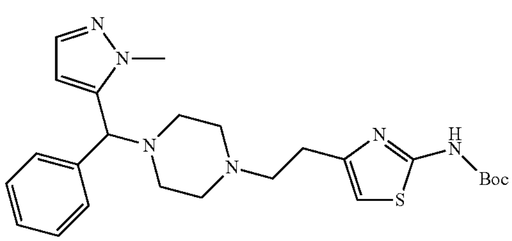 [SMILES: Cn1nccc1C(c1ccccc1)N1CCN(CCc2csc(NC(=O)OC(C)(C)C)n2)CC1] | tert-butyl 4-(2-(4-((1-methyl-1H-pyrazol-5-yl)(phenyl)methyl)piperazin-1-yl)ethyl)thiazol-2-ylcarbamate | B | 2.01 | 483.4 |
| 26 | 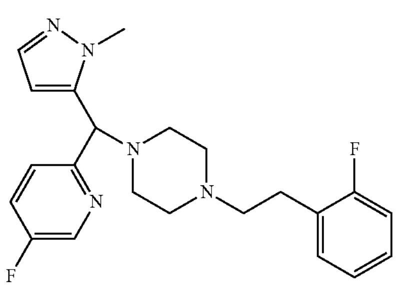 [SMILES: Cn1nccc1C(c1ccc(F)cn1)N1CCN(CCc2ccccc2F)CC1] | 1-(2-fluorophenethyl)-4-((5-fluoropyridin-2-yl)(1-methyl-1H-pyrazol-5-yl)methyl)piperazine | B | 1.92 | 398.3 |

| EX | Structure | Chemical name | Method | Ret (min) | MS (M + H) |
|---|---|---|---|---|---|
| 27 | 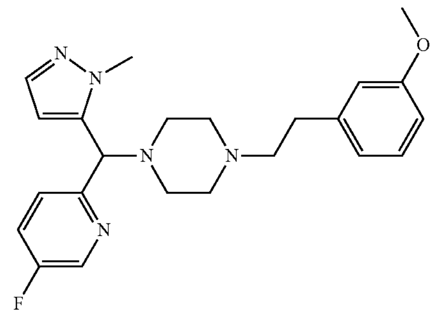 [SMILES: COc1cccc(CCN2CCN(C(c3ccc(F)cn3)c3ccnn3C)CC2)c1] | 1-((5-fluoropyridin-2-yl)(1-methyl-1H-pyrazol-5-yl)methyl)-4-(3-methoxyphenethyl)piperazine | B | 1.82 | 410.2 |

Example 28

2-(2-(4-((1-Methyl-1H-pyrazol-5-yl)(phenyl)methyl)piperazin-1-yl)ethyl)phenol

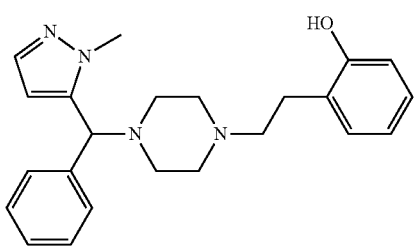 [SMILES: Cn1nccc1C(c1ccccc1)N1CCN(CCc2ccccc2O)CC1]

BBr₃ (1M in DCM, 280 μL, 0.28 mmol) was added dropwise to a solution of 1-(2-methoxyphenethyl)-4-((1-methyl-1H-pyrazol-5-yl)(phenyl)methyl)piperazine (example 6, 22 mg, 0.056 mmol) in DCM (3 mL) cooled to 0° C. The reaction mixture was stirred at 0° C. for 2 h and then it was poured to an ice bath. The resulting suspension was allowed to reach r.t., extracted several times with DCM, and the combined organic layers were dried over Na₂SO₄, filtered and concentrated. The crude residue was purified by flash chromatography on silica gel, eluents DCM:MeOH (97:3) to give the title compound (2.6 mg, yield 12%).

HPLC-MS (Method B): Ret, 2.05 min; ESI⁺-MS m/z, 377.3 (M+1).

A similar method was used for the preparation of examples 29-31, using the corresponding methoxy analogues as starting materials:

| EX | Structure | Chemical name | Method | Ret (min) | MS (M + H) |
|---|---|---|---|---|---|
| 29 | 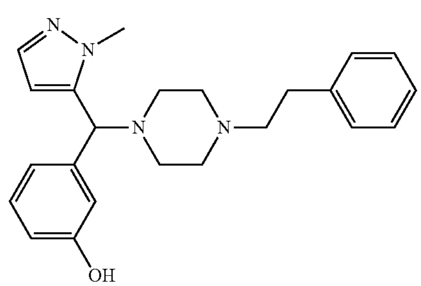 [SMILES: Cn1nccc1C(c1cccc(O)c1)N1CCN(CCc2ccccc2)CC1] | 3-((1-methyl-1H-pyrazol-5-yl)(4-phenethylpiperazin-1-yl)methyl)phenol | B | 1.76 | 377.3 |
| 30 | 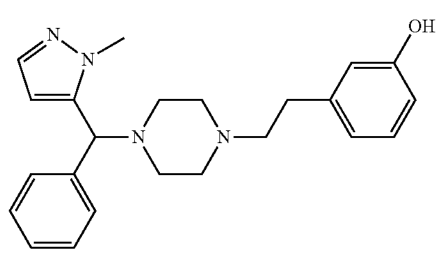 [SMILES: Cn1nccc1C(c1ccccc1)N1CCN(CCc2cccc(O)c2)CC1] | 3-(2-(4-((1-methyl-1H-pyrazol-5-yl)(phenyl)methyl)piperazin-1-yl)ethyl)phenol | B | 1.71 | 377.3 |

| EX | Structure | Chemical name | Method | Ret (min) | MS (M + H) |
|---|---|---|---|---|---|
| 31 | 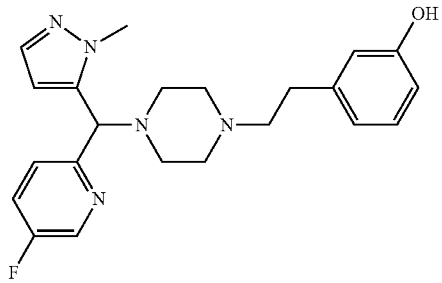 [SMILES: Cn1nccc1C(c1ccc(F)cn1)N1CCN(CCc2cccc(O)c2)CC1] | 3-(2-(4-((5-fluoropyridin-2-yl)(1-methyl-1H-pyrazol-5-yl)methyl)piperazin-1-yl)ethyl)phenol | B | 1.51 | 396.2 |

Example 32

4-(2-(4-((1-Methyl-1H-pyrazol-5-yl)(phenyl)methyl)piperazin-1-yl)ethyl)thiazol-2-amine

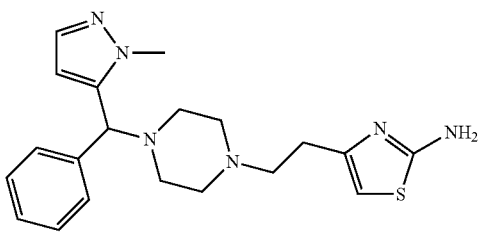 [SMILES: Cn1nccc1C(c1ccccc1)N1CCN(CCc2csc(N)n2)CC1]

TFA (29 μL, 0.378 mmol) was added to a solution of tert-butyl 4-(2-(4-((1-methyl-1H-pyrazol-5-yl)(phenyl)methyl)piperazin-1-yl)ethyl)thiazol-2-ylcarbamate (example 25, 36.4 mg, 0.076 mmol) in DCM (2 mL). The reaction mixture was stirred at r.t. for 3.5 h and then the solvents were evaporated. The residue was redissolved in DCM and washed with aqueous saturated solution of NaHCO₃. The organic layer was dried over Na₂SO₄, filtered and concentrated. The crude residue was purified by flash chromatography on neutral alumina, gradient DCM:MeOH from (100:0) to (98:2) to give the title compound as a colorless oil (31 mg, quantitative yield).

HPLC-MS (Method B): Ret, 1.48 min; ESI⁺-MS m/z, 383.3 (M+1).

Example 33

1-(2-(3-Fluoropyridin-2-yl)ethyl)-4-((1-methyl-1H-pyrazol-5-yl)(phenyl)methyl)piperazine

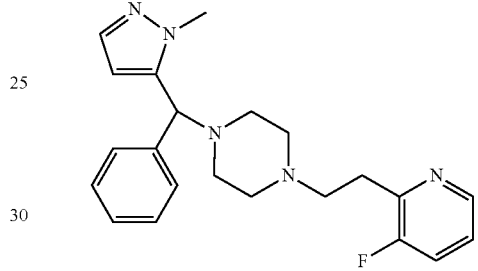

DIPEA (149 mL, 0.858 mmol) was added dropwise to a solution of 1-((1-methyl-1H-pyrazol-5-yl)(phenyl)methyl)piperazine (intermediate 2A, 100 mg, 0.39 mmol) in ethanol (4 mL) in a process vial. Then, 2-(2-chloroethyl)-3-fluoropyridine (74.7 mg, 0.468 mmol) was added and the reaction mixture was subjected to 3 cycles of microwave irradiating conditions of 2 h at 80° C. In the last cycle, a catalytic amount of KI was added. The vial was cooled and aqueous saturated solution of NaHCO₃ and AcOEt were added to the reaction mixture. The organic layer was separated, dried over Na₂SO₄, filtered and concentrated. The crude residue was purified by flash chromatography on neutral alumina, gradient DCM:MeOH from (100:0) to (90:10) to afford the title compound (40 mg, 27% yield).

HPLC-MS (Method B): Ret, 2.36 min; ESI⁺-MS m/z, 380.2 (M+1).

Example 34 was prepared by the same method, using 2-(2-chloroethyl)-5-fluoropyridine as alkylating agent

| EX | Structure | Chemical name | Method | Ret (min) | MS (M + H) |
|---|---|---|---|---|---|
| 34 | 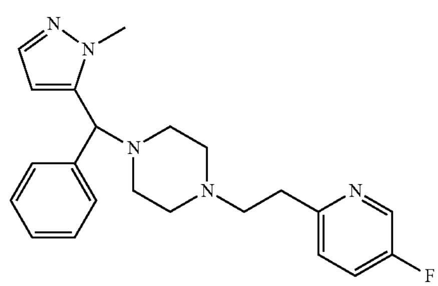 [SMILES: Cn1nccc1C(c1ccccc1)N1CCN(CCc2ccc(F)cn2)CC1] | 1-(2-(5-fluoropyridin-2-yl)ethyl)-4-((1-methyl-1H-pyrazol-5-yl)(phenyl)methyl)piperazine | B | 1.71 | 380.3 |

Example 35

1-(3-Fluorophenethyl)-4-((1-methyl-1H-pyrazol-5-yl)(phenyl)methyl)piperazine

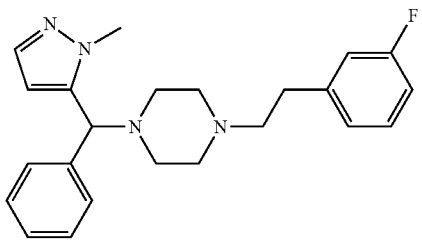 [SMILES: Cn1nccc1C(c1ccccc1)N1CCN(CCc2cccc(F)c2)CC1]

a) 2-(3-Fluorophenyl)-1-(4-((1-methyl-1H-pyrazol-5-yl)(phenyl)methyl)piperazin-1-yl)ethanone A mixture of 2-(3-fluorophenyl)acetic acid (70.2 mg, 0.456 mmol) and HOBt (116.3 mg, 0.759 mmol) in DMF (3 mL) was added to a solution of EDC (145.5 mg, 0.759 mmol) in DMF (5 mL). Then, 1-((1-methyl-1H-pyrazol-5-yl)(phenyl)methyl)piperazine hydrochloride (intermediate 2A, 125 mg, 0.38 mmol) was added in DMF (2 mL) and the mixture was adjusted to pH=10 with Et$_3$N. The reaction mixture was stirred at r.t. overnight and then the DMF was removed in vacuo and the residue was partioned between EtOAc/Et$_2$O 1/1 and water. The organic layer was washed with water, dried over Na$_2$SO$_4$, filtered and concentrated to obtain a crude compound that was purified by flash chromatography on silica gel, gradient DCM:MeOH from (100:0) to (97:3) to afford the title compound as a yellow oil (55 mg, yield 37%).

HPLC-MS (Method B): Ret, 1.83 min; ESI$^+$-MS m/z, 393.3 (M+1).

b) Title Compound 2-(3-Fluorophenyl)-1-(4-((1-methyl-1H-pyrazol-5-yl)(phenyl)methyl)piperazin-1-yl)ethanone (obtained in the previous step, 55 mg, 0.170 mmol) in THF (4 mL) was added dropwise to a stirred solution of freshly prepared aluminium hydride (700 µL, 0.7 mmol) in THF (4 mL). The reaction was maintained at 0° C. and stirred for 1.5 h, and then a few drops of water were added to destroy the aluminum hydride excess. Water and AcOEt were added to the mixture and the aqueous layer was separated and extracted several times with AcOEt. The organic layers were combined, dried over Na$_2$SO$_4$, filtered and concentrated. The crude residue was purified by flash chromatography on silica gel, gradient DCM:MeOH from (100:0) to (98:2) to give the title compound as a colorless oil (31 mg, yield 56.6%).

HPLC-MS (Method B): Ret, 2.16 min; ESI$^+$-MS m/z, 379.3 (M+1).

A similar method was used for the preparation of examples 36-38, using intermediates 2A and 2B as starting materials and suitable carboxylic acids:

| EX | Structure | Chemical name | Method | Ret (min) | MS (M + H) |
|---|---|---|---|---|---|
| 36 | 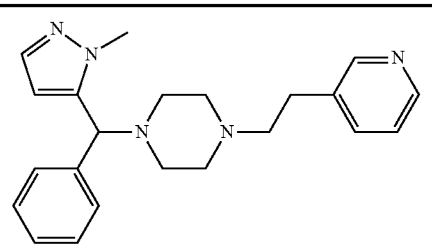 | 1-((1-methyl-1H-pyrazol-5-yl)(phenyl)methyl)-4-(2-(pyridin-3-yl)ethyl)piperazine | B | 1.58 | 362.4 |
| 37 | 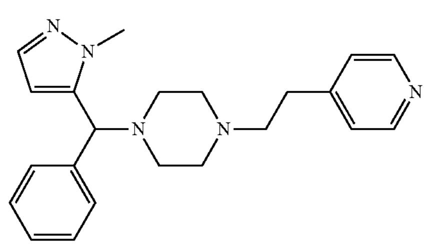 [SMILES: Cn1nccc1C(c1ccccc1)N1CCN(CCc2ccncc2)CC1] | 1-((1-methyl-1H-pyrazol-5-yl)(phenyl)methyl)-4-(2-(pyridin-4-yl)ethyl)piperazine | B | 1.57 | 362.4 |
| 38 | 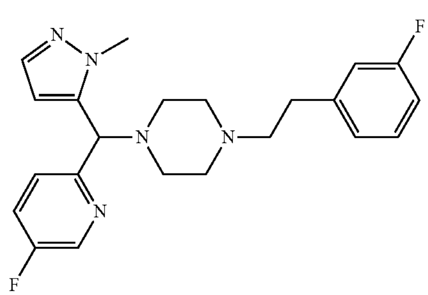 [SMILES: Cn1nccc1C(c1ccc(F)cn1)N1CCN(CCc2cccc(F)c2)CC1] | 1-(3-fluorophenethyl)-4-((5-fluoropyridin-2-yl)(1-methyl-1H-pyrazol-5-yl)methyl)piperazine | B | 1.89 | 398.2 |

Example 39

2-(4-((1-Methyl-1H-pyrazol-5-yl)(phenyl)methyl)piperazin-1-yl)-1-phenylethanol

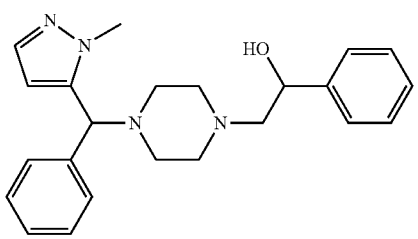 [SMILES: Cn1nccc1C(c1ccccc1)N1CCN(CC(O)c2ccccc2)CC1]

2-Phenyloxirane (53.3 μL, 0.468 mmol) was added to a solution of 1-((1-methyl-1H-pyrazol-5-yl)(phenyl)methyl)piperazine (intermediate 2A, 60 mg, 0.234 mmol) in anhydrous toluene (4 mL). The reaction mixture was stirred at 110° C. overnight and then the volatile components were removed on a rotavap and the crude residue was purified by preparative HPLC: Column: X-Bridge C18; Temperature: ambient; Flow: 20 mL/min; Mobile phase: NH$_4$HCO$_3$ 10 mM/ACN; to afford the title compound (24 mg, 25% yield).

HPLC-MS (Method B): Ret, 1.9 min; ESI$^+$-MS m/z, 377.3 (M+1).

Example 40

6-(2-(4-((1-Methyl-1H-pyrazol-5-yl)(phenyl)methyl)piperazin-1-yl)ethyl)pyridin-2-amine

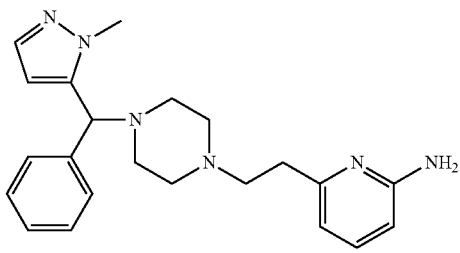 [SMILES: Cn1nccc1C(c1ccccc1)N1CCN(CCc2cccc(N)n2)CC1]

A solution of 1-((1-methyl-1H-pyrazol-5-yl)(phenyl)methyl)piperazine (intermediate 2A, 300 mg, 1.17 mmol) and 6-vinylpyridin-2-amine (211 mg, 1.75 mmol) in 2-methoxyethanol (4 mL) was heated at 120° C. in a sealed tube for 2 days. The reaction mixture was cooled to r.t. and the solvent was evaporated. The residue was purified by flash chromatography on silica gel, gradient DCM:MeOH from (100:0) to (40:60) to afford the title compound (60 mg, 14% yield).

HPLC-MS (Method B): Ret, 1.53 min; ESI$^+$-MS m/z, 377.4 (M+1).

A similar method was used for the preparation of examples 41-43, using intermediates 2A and 2B as starting materials and suitable vinylpyridines:

| EX | Structure | Chemical name | Method | Ret (min) | MS (M + H) |
|----|-----------|---------------|--------|-----------|------------|
| 41 | 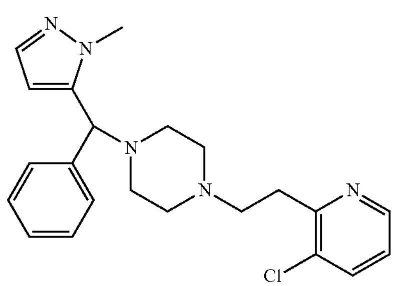 [SMILES: Cn1nccc1C(c1ccccc1)N1CCN(CCc2ncccc2Cl)CC1] | 1-(2-(3-chloropyridin-2-yl)ethyl)-4-((1-methyl-1H-pyrazol-5-yl)(phenyl)methyl)piperazine | B | 2.52 | 396.2 |
| 42 | 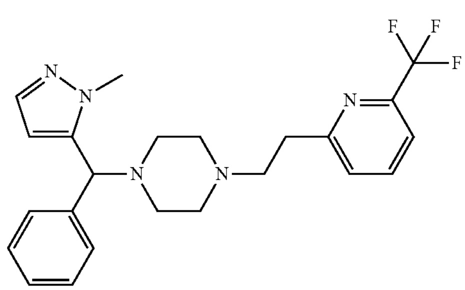 [SMILES: Cn1nccc1C(c1ccccc1)N1CCN(CCc2cccc(C(F)(F)F)n2)CC1] | 1-((1-methyl-1H-pyrazol-5-yl)(phenyl)methyl)-4-(2-(6-(trifluoromethyl)pyridin-2-yl)ethyl)piperazine | B | 2.04 | 430.3 |

| EX | Structure | Chemical name | Method | Ret (min) | MS (M + H) |
|---|---|---|---|---|---|
| 43 | 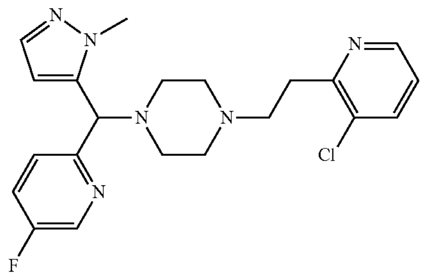 [SMILES: Cn1nccc1C(c1ccc(F)cn1)N1CCN(CCc2ncccc2Cl)CC1] | 1-(2-(3-chloropyridin-2-yl)ethyl)-4-((5-fluoropyridin-2-yl)(1-methyl-1H-pyrazol-5-yl)methyl)piperazine | B | 1.60 | 415.2 |

Example 44

N-(6-(2-(4-((1-methyl-1H-pyrazol-5-yl)(phenyl)methyl)piperazin-1-yl)ethyl)pyridin-2-yl)methanesulfonamide

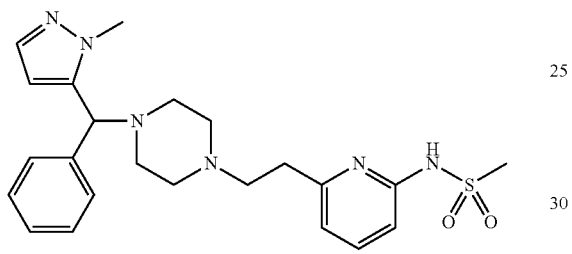

Et₃N (37.2 µL, 0.267 mmol) was added to a solution of 6-(2-(4-((1-methyl-1H-pyrazol-5-yl)(phenyl)methyl)piperazin-1-yl)ethyl)pyridin-2-amine (example 40, 53 mg, 0.134 mmol) in DCM (5 mL) and the mixture was stirred for 15 min at r.t. Then, methanesulfonyl chloride (12.4 µL, 0.160 mmol) was added and it was stirred at r.t. overnight. The reaction mixture was washed with water and the combined aqueous layers were extracted with DCM. The combined DCM organic layers were dried over Na₂SO₄, filtered, concentrated and set aside to obtain example 45. The aqueous layers were extracted again with AcOEt and the combined AcOEt organic layers were dried over Na₂SO₄, filtered and concentrated to obtain the title compound (12 mg, 20% yield).

HPLC-MS (Method B): Ret, 1.41 min; ESI⁺-MS m/z, 455.4 (M+1).

Example 45

N-(6-(2-(4-((1-methyl-1H-pyrazol-5-yl)(phenyl)methyl)piperazin-1-yl)ethyl)pyridin-2-yl)-N-(methylsulfonyl)methanesulfonamide

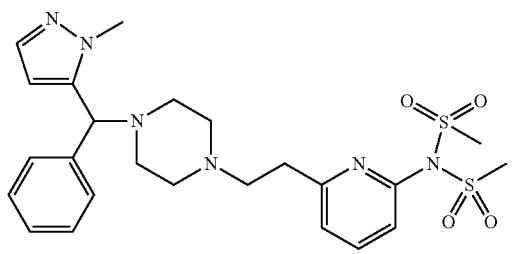 [SMILES: Cn1nccc1C(c1ccccc1)N1CCN(CCc2cccc(N(S(C)(=O)=O)S(C)(=O)=O)n2)CC1]

The residue obtained from the combined DCM organic layers in the work-up procedure for the obtention of example 44 was purified by flash chromatography on silica gel, gradient DCM:MeOH from (100:0) to (90:10) to afford the title compound as bisulfonamide by-product (21 mg, 28% yield).

HPLC-MS (Method B): Ret, 1.76 min; ESI⁺-MS m/z, 533.2 (M+1).

Example 46

N-(1-methyl-1H-pyrazol-5-yl)-1-phenethyl-N-phenyl piperidin-4-amine

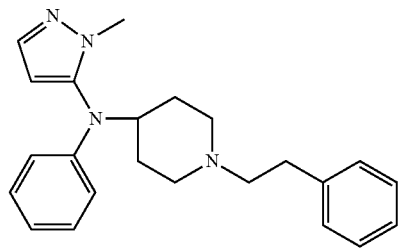 [SMILES: Cn1nccc1N(c1ccccc1)C1CCN(CCc2ccccc2)CC1]

a) N-(1-methyl-1H-pyrazol-5-yl)-1-phenethyl-1,2,3,6-tetrahydropyridin-4-amine

1-Methyl-1H-pyrazol-5-amine (120 mg. 0.123 mmol) and few crystals of p-toluenesulfonic acid (catalytic amount) were added to a solution of 1-phenethylpiperidin-4-one (251 mg, 0.123 mmol) in toluene (12 mL) and the reaction mixture was refluxed overnight. Then, the solvent was evaporated, the residue was redissolved in MeOH and NaBH₄ (93 mg, 2.46 mmol) was added. The reaction mixture was stirred at r.t. for 4 h and a few drops of water were added to destroy the NaBH₄ excess. The solvents were evaporated and the residue was redissolved in DCM and washed with water. The organic layer was dried over Na₂SO₄, filtered and concentrated. The crude residue was purified by flash chromatography on silica gel, gradient CHCl₃:MeOH from (100:0) to (90:10) to give the title compound (174.1 mg, 50% yield).

HPLC-MS (Method B): Ret, 1.49 min; ESI⁺-MS m/z, 283.3 (M+1).

b) N-(1-methyl-1H-pyrazol-5-yl)-1-phenethyl-N-phenyl-1,2,3,6-tetrahydropyridin-4-amine N-(1-methyl-1H-pyrazol-5-yl)-1-phenethyl-1,2,3,6-tetrahydropyridin-4-amine (obtained in the previous step, 174 mg, 0.616 mmol), $Pd_2(dba)_3$ (22.5 mg, 0.025 mmol), 4,5-bis(diphenylphosphino)-9,9-dimethylxanthene (Xantphos) (28.5 mg, 0.049 mmol) and tBuOK (96.8 mg, 0.863 mmol) were added to a Schlenk tube, submitted to 3 cycles of vacuum-argon and dissolved in anhydrous toluene (15 mL). The mixture was heated to 50° C. and bromobenzene (129.8 µL, 1.232 mmol) was added. The reaction mixture was stirred at 100° C. overnight. Then the solvents were evaporated and the residue was purified by flash chromatography on silica gel, gradient $CHCl_3$:MeOH from (100:0) to (90:10) to give the title compound (48 mg, 22% yield).

HPLC-MS (Method B): Ret, 2.10 min; $ESI^+$-MS m/z, 359.3 (M+1).

c) Title Compound

A mixture of N-(1-methyl-1H-pyrazol-5-yl)-1-phenethyl-N-phenyl-1,2,3,6-tetrahydropyridin-4-amine (37.4 mg, 0.1 mmol) and palladium (6 mg, 15% wt on charcoal) in ethanol (4 mL) was stirred at r.t. under 50 psi of $H_2$ overnight. Then, additional palladium (3 mg, 15% wt on charcoal) was added, and the reaction mixture was stirred at r.t. under 50 psi of $H_2$. After 18 h, the solids were filtered off, the solvent was removed under vacuum and the crude residue was purified by preparative HPLC: Column: X-Bridge C18; Temperature: ambient; Flow: 20 mL/min; Mobile phase: $NH_4HCO_3$ 10 mM/ACN; to afford the title compound (8 mg, 21% yield).

HPLC-MS (Method B): Ret, 2.02 min; $ESI^+$-MS m/z, 361.3 (M+1).

Example 47 was prepared by the same method, using 1-benzylpiperidin-4-one in step a

| EX | Structure | Chemical name | Method | Ret (min) | MS (M + H) |
|---|---|---|---|---|---|
| 47 | 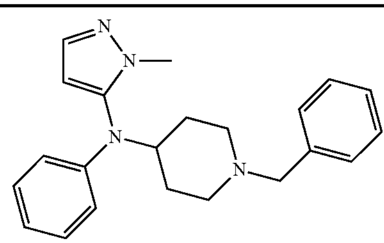 | 1-benzyl-N-(1-methyl-1H-pyrazol-5-yl)-N-phenylpiperidin-4-amine | B | 2.04 | 347.3 |

Table of Examples with Binding to the µ-opioid Receptor and the σ1-Receptor:
Biological Activity
Pharmacological Study
Human $σ_1$ Receptor Radioligand Assay To investigate binding properties of test compounds to human sigma-1 receptor, transfected HEK-293 membranes and [$^3$H](+)-pentazocine (Perkin Elmer, NET-1056), as the radioligand, were used. The assay was carried out with 7 µg of membrane suspension, 5 nM of [$^3$H](+)-pentazocine in either absence or presence of either buffer or 10 µM Haloperidol for total and non-specific binding, respectively. Binding buffer contained Tris-HCl 50 mM at pH 8. Plates were incubated at 37° C. for 120 minutes. After the incubation period, the reaction mix was then transferred to MultiScreen HTS, FC plates (Millipore), filtered and plates were washed 3 times with ice-cold 10 mM Tris-HCL (pH7.4). Filters were dried and counted at approximately 40% efficiency in a MicroBeta scintillation counter (Perkin-Elmer) using EcoScint liquid scintillation cocktail Human µ-opioid Receptor Radioligand Assay To investigate binding properties of test compounds to human µ-opioid receptor, transfected CHO-K1 cell membranes and [$^3$H]-DAMGO (Perkin Elmer, ES-542-C), as the radioligand, were used. The assay was carried out with 20 µg of membrane suspension, 1 nM of [$^3$H]-DAMGO in either absence or presence of either buffer or 10 µM Naloxone for total and non-specific binding, respectively. Binding buffer contained Tris-HCl 50 mM, MgCl2 5 mM at pH 7.4. Plates were incubated at 27° C. for 60 minutes. After the incubation period, the reaction mix was then transferred to MultiScreen HTS, FC plates (Millipore), filtered and plates were washed 3 times with ice-cold 10 mM Tris-HCL (pH 7.4). Filters were dried and counted at approximately 40% efficiency in a MicroBeta scintillation counter (Perkin-Elmer) using EcoScint liquid scintillation cocktail.

Results:

As this invention is aimed at providing a compound or a chemically related series of compounds which act as dual ligands of the $σ_1$ receptor and the µ-opiod receptor it is a very preferred embodiment in which the compounds are selected which act as dual ligands of the $σ_1$ receptor and the µ-opiod receptor and especially compounds which have a binding expressed as $K_i$ which is preferably <1000 nM for both receptors, more preferably <500 nM, even more preferably <100 nM.

The following scale as been adopted for representing the binding to the $σ_1$ receptor and the µ-opiod receptor expressed as $K_i$:

+ Both $K_i$-µ and $K_i$-$σ_1$ >=500 nM
++ One $K_i$<500 nM while the other $K_i$ is >=500 nM
+++ Both $K_i$-µ and $K_i$-$σ_1$<500 nM
++++ Both $K_i$-µ and $K_i$-$σ_1$<100 nM All compounds prepared in the present application exhibit binding to the $σ_1$ receptor and the µ-opiod receptor, in particular the following binding results are shown:

| EX | µ and $σ_1$ dual binding |
|---|---|
| 1 | ++ |
| 2 | ++ |
| 3 | ++++ |
| 4 | ++ |
| 5 | ++ |
| 6 | + |
| 7 | ++++ |

-continued

| EX | μ and σ₁ dual binding |
|---|---|
| 8 | +++ |
| 9 | +++ |
| 10 | ++ |
| 11 | ++ |
| 12 | +++ |
| 13 | ++ |
| 14 | ++ |
| 15 | + |
| 16 | ++ |
| 17 | +++ |
| 18 | ++ |
| 19 | ++ |
| 20 | ++ |
| 21 | +++ |
| 22 | ++++ |
| 23 | ++ |
| 24 | + |
| 25 | + |
| 26 | ++ |
| 27 | ++ |
| 28 | ++ |
| 29 | +++ |
| 30 | ++++ |
| 31 | ++ |
| 32 | + |
| 33 | + |
| 34 | + |
| 35 | +++ |
| 36 | + |
| 37 | ++ |
| 38 | +++ |
| 39 | ++ |
| 40 | + |
| 41 | ++ |
| 42 | + |
| 43 | ++ |
| 44 | + |
| 45 | + |
| 46 | ++ |
| 47 | ++ |

The invention claimed is:

1. A compound of formula (I):

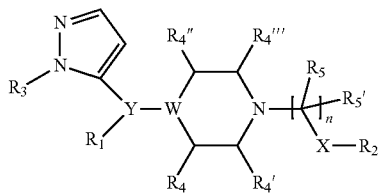

(I)

wherein
n is 1, 2, 3, 4, 5 or 6;
Y—W is $CR_y$—N;
X is a bond or —$CR_6R_{6'}$—;
$R_1$ is substituted or unsubstituted cycloalkyl, substituted or unsubstituted aryl, or substituted or unsubstituted heterocyclyl;
$R_2$ is substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl, or substituted or unsubstituted heterocyclyl;
$R_3$ is hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl, substituted or unsubstituted heterocyclyl, substituted or unsubstituted alkylcycloalkyl, substituted or unsubstituted alkylaryl, or substituted or unsubstituted alkylheterocyclyl;
$R_4$, $R_{4'}$, $R_{4''}$ and $R_{4'''}$ are independently selected from hydrogen or unsubstituted $C_{1-6}$ alkyl, unsubstituted $C_{2-6}$ alkenyl, and unsubstituted $C_{2-6}$ alkynyl;
$R_5$ and $R_{5'}$ are independently selected from hydrogen or unsubstituted $C_{1-6}$ alkyl, unsubstituted $C_{2-6}$ alkenyl, and unsubstituted $C_{2-6}$ alkynyl;
$R_6$ is selected from hydrogen, halogen, —$OR_7$, substituted or unsubstituted $C_{1-6}$ alkyl, substituted or unsubstituted $C_{2-6}$ alkenyl, substituted or unsubstituted $C_{2-6}$ alkynyl, —$C(O)OR_7$, —$C(O)NR_7R_{7'}$, —$NR_7C(O)R_{7'}$, and —$NR_7R_{7'''}$—;
$R_{6'}$ is selected from hydrogen, substituted or unsubstituted $C_{1-6}$ alkyl, substituted or unsubstituted $C_{2-6}$ alkenyl, and substituted or unsubstituted $C_{2-6}$ alkynyl;
wherein $R_7$ and $R_{7'}$ are independently selected from hydrogen, unsubstituted $C_{1-6}$ alkyl, unsubstituted $C_{2-6}$ alkenyl, unsubstituted $C_{2-6}$ alkynyl, and unsubstituted acetyl;
and $R_{7'''}$ is selected from hydrogen, unsubstituted $C_{1-6}$ alkyl, unsubstituted $C_{2-6}$ alkenyl, unsubstituted $C_{2-6}$ alkynyl and -Boc;
$R_y$ is selected from hydrogen, substituted or unsubstituted $C_{1-6}$ alkyl, substituted or unsubstituted $C_{2-6}$ alkenyl, and substituted or unsubstituted $C_{2-6}$ alkynyl;
optionally as a stereoisomer, a racemate or a mixture of at least two of stereoisomers, in any mixing ratio, or a corresponding salt thereof.

2. The compound according to claim 1, wherein
$R_1$ is substituted or unsubstituted aryl or substituted or unsubstituted heterocyclyl; and/or
$R_2$ is substituted or unsubstituted aryl or substituted or unsubstituted heterocyclyl;
and/or
$R_3$ is hydrogen, substituted or unsubstituted $C_{1-6}$ alkyl, substituted or unsubstituted $C_{2-6}$ alkenyl, or substituted or unsubstituted $C_{2-6}$ alkynyl.

3. The compound according to claim 2, wherein $R_3$ is hydrogen or substituted or unsubstituted $C_{1-6}$ alkyl.

4. The compound according to claim 2, wherein
$R_1$ is substituted or unsubstituted aryl or substituted or unsubstituted heterocyclyl;
$R_2$ is substituted or unsubstituted aryl or substituted or unsubstituted heterocyclyl; and
$R_3$ is hydrogen, substituted or unsubstituted $C_{1-6}$ alkyl, substituted or unsubstituted $C_{2-6}$ alkenyl, or substituted or unsubstituted $C_{2-6}$ alkynyl.

5. The compound according to claim 4, wherein $R_3$ is hydrogen or substituted or unsubstituted $C_{1-6}$ alkyl.

6. The compound according to claim 1, wherein X is a bond.

7. The compound according to claim 1, wherein n is 1 or 2, X is a bond, and $R_2$ is a substituted or unsubstituted group selected from phenyl, pyridine, and thiazole.

8. The compound according to claim 1, wherein $R_1$ is a substituted or unsubstituted group selected from phenyl and pyridine; and/or
wherein $R_3$ is methyl and $R_4$, $R_{4'}$, $R_{4''}$ and $R_{4'''}$ are all hydrogen.

9. The compound according to claim 1, which is selected from:
1-((1-methyl-1H-pyrazol-5-yl)(phenyl)methyl)-4-(2-(pyridin-2-yl)ethyl)piperazine, 1-benzyl-4-((1-methyl-1H-pyrazol-5-yl)(phenyl)methyl)
 piperazine,
1-((1-methyl-1H-pyrazol-5-yl)(phenyl)methyl)-4-phen-
 ethylpiperazine,
1-((1-methyl-1H-pyrazol-5-yl)(pyridin-2-yl)methyl)-4-
 phenethylpiperazine,
1-((1-methyl-1H-pyrazol-5-yl)(pyridin-3-yl)methyl)-4-
 phenethylpiperazine,
1-(2-methoxyphenethyl)-4-((1-methyl-1H-pyrazol-5-yl)
 (phenyl)methyl)piperazine,
1-((3-methoxyphenyl)(1-methyl-1H-pyrazol-5-yl)
 methyl)-4-phenethylpiperazine,
1-((2-methoxyphenyl)(1-methyl-1H-pyrazol-5-yl)
 methyl)-4-phenethylpiperazine,
1-((4-methoxyphenyl)(1-methyl-1H-pyrazol-5-yl)
 methyl)-4-phenethylpiperazine,
1-((1-methyl-1H-pyrazol-1-5-yl)(6-(trifluoromethyl)pyri-
 din-2-yl)methyl)-4-phenethylpiperazine,
1-((1-methyl-1H-pyrazol-5-yl)(6-(trifluoromethyl)pyri-
 din-3-yl)methyl)-4-phenethylpiperazine,
1-((5-fluoropyridin-2-yl)(1-methyl-1H-pyrazol-5-yl)
 methyl)-4-phenethylpiperazine,
1-((5-fluoropyridin-3-yl)(1-methyl-1H-pyrazol-5-
 methyl)-4-phenethylpiperazine,
1-((1-methyl-1H-pyrazol-5-yl)(5-(trifluoromethyl)pyri-
 din-2-yl)methyl)-4-phenethylpiperazine,
1-((5-fluoropyridin-2-yl)(1-methyl-1H-pyrazol-5-yl)
 methyl)-4-(2-(pyridin-2-yl)ethyl)piperazine,
1-((3-fluoropyridin-2-yl)(1-methyl-1H-pyrazol-5-
 methyl)-4-phenethylpiperazine,
1-((1-methyl-1H-pyrazol-5-yl)(2-(trifluoromethyl)pyri-
 din-3-yl)methyl)-4-phenethylpiperazine,
1-((5-chloropyridin-2-yl)(1-methyl-1H-pyrazol-5-yl)
 methyl)-4-phenethylpiperazine,
1-((1-methyl-1H-pyrazol-5-yl)(4-(trifluoromethyl)pyri-
 din-3-yl)methyl)-4-phenethylpiperazine,
1-((1-methyl-1H-pyrazol-5-yl)(pyridin-4-yl)methyl)-4-
 phenethylpiperazine,
1-(3-methoxyphenethyl)-4-((1-methyl-1H-pyrazol-5-yl)
 (phenyl)methyl)piperazine,
1-(2-fluorophenethyl)-4-((1-methyl-1H-pyrazol-5-yl)
 (phenyl)methyl)piperazine,
1-(4-fluorophenethyl)-4-((1-methyl-1H-pyrazol-5-yl)
 (phenyl)methyl)piperazine,
1-((1-methyl-1H-pyrazol-5-yl)(phenyl)methyl)-4-(2-(6-
 (trifluoromethyl)pyridin-3-yl)ethyl)piperazine,
tert-butyl 4-(2-(4-((1-methyl-1H-pyrazol-5-yl)(phenyl)
 methyl)piperazin-1-yl)ethyl)thiazol-2-ylcarbamate,
1-(2-fluorophenethyl)-4-((5-fluoropyridin-2-yl)(1-
 methyl-1H-pyrazol-5-yl)methyl)piperazine,
1-((5-fluoropyridin-2-yl)(1-methyl-1H-pyrazol-5-yl)
 methyl)-4-(3-methoxyphenethyl)piperazine,
2-(2-(4-((1-methyl-1H-pyrazol-5-yl)(phenyl)methyl)pip-
 erazin-1-yl)ethyl)phenol,
3-((1-methyl-1H-pyrazol-5-yl)(4-phenethylpiperazin-1-
 yl)methyl)phenol,
3-(2-(4-((1-methyl-1H-pyrazol-5-yl)(phenyl)methyl)pip-
 erazin-1-yl)ethyl)phenol,
3-(2-(4-((5-fluoropyridin-2-yl)(1-methyl-1H-pyrazol-5-
 yl)methyl)piperazin-1-yl)ethyl)phenol,
4-(2-(4-((1-methyl-1H-pyrazol-5-yl)(phenyl)methyl)pip-
 erazin-1-yl)ethyl)thiazol-2-amine,
1-(2-(3-fluoropyridin-2-yl)ethyl)-4-((1methyl-1H-pyra-
 zol-5-yl)(phenyl)methyl)piperazine,
1-(2-(5-fluoropyridin-2-yl)ethyl)-4-((1-methyl-1H-pyra-
 zol-5-yl)(phenyl)methyl)piperazine,
1-(3-fluorophenethyl)-4-((1methyl-1H-pyrazol-5-yl)
 (phenyl)methyl)piperazine,
1-((1-methyl-1H-pyrazol-5-yl)(phenyl)methyl)-4-(2-
 (pyridin-3-yl)ethyl)piperazine,
1-((1-methyl-1H-pyrazol-5-yl)(phenyl)methyl)-4-(2-
 (pyridin-4-yl)ethyl)piperazine,
1-(3-fluorophenethyl)-4-((5-fluoropyridin-2-yl)(1-
 methyl-1H-pyrazol-5-yl)methyl)piperazine,
2-(4-((1-methyl-1H-pyrazol-5-yl)(phenyl)methyl)piper-
 azin-1-yl)-1-phenylethanol,
6-(2-(4-((1-methyl-1H-pyrazol-5-yl)(phenyl)methyl)pip-
 erazin-1-yl)ethyl)pyridin-2-amine,
1-(2-(3-chloropyridin-2-yl)ethyl)-4-((1-methyl-1H-pyra-
 zol-5-yl)(phenyl)methyl)piperazine,
1-((1-methyl-1H-pyrazol-5-yl)(phenyl)methyl)-4-(2-(6-
 (trifluoromethyl)pyridin-2-yl)ethyl)piperazine,
1-(2-(3-chloropyridin-2-yl)ethyl)-4-((5-fluoropyridin-2-
 yl)(1-methyl-1H-pyrazol-5-yl)methyl)piperazine,
N-(6-(2-(4-((1-methyl-1H-pyrazol-5-yl)(phenyl)methyl)
 piperazin-1-yl)ethyl)pyridin-2-yl)methanesulfona-
 mide, and
N-(6-(2-(4-((1-methyl-1H-pyrazol-5-yl)(phenyl)methyl)
 piperazin-1-yl)ethyl)pyridin-2-yl)-N-(methylsulfonyl)
 methanesulfonamide,
optionally as a stereoisomer, a racemate or a mixture of at
 least two stereoisomers, in any mixing ratio, or a
 corresponding salt thereof.

10. A process for preparing a compound of formula (I) according to claim 1

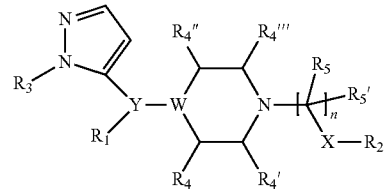

(I)

which process comprises
(a) reducing a compound of formula VI

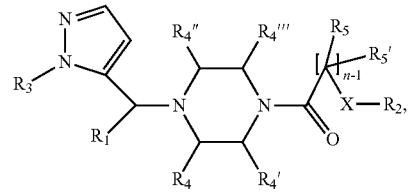

(VI)

(b) reacting a compound of formula IV

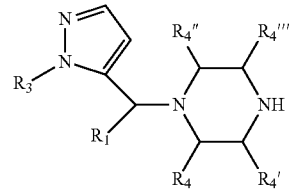

(IV)

with a suitable reagent of formula Va, Vb or Vc,

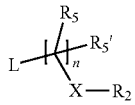 (Va)

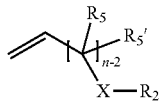 (Vb)

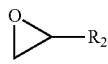 (Vc)

wherein L is a leaving group,
or
(c) reacting a compound of formula II

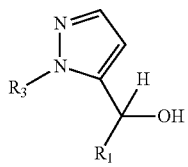 (II)

first with methanesulfonyl chloride followed by an alkylation reaction with a compound of formula VII

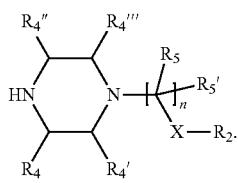 (VII)

11. A process for the preparation of the compound of formula (I) according to claim 1, employing a compound of Formula (II), (III), (IV), (Va), (Vb), (Vc), Vd), (VI) or (VII)

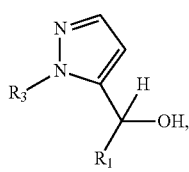 (II)

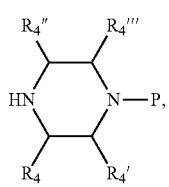 (III)

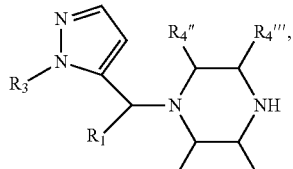 (V)

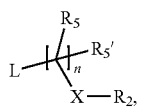 (Va)

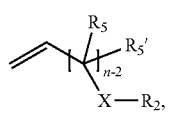 (Vb)

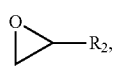 (Vc)

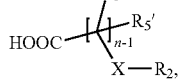 (Vd)

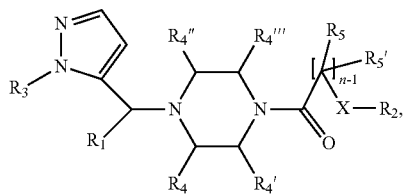 (VI)

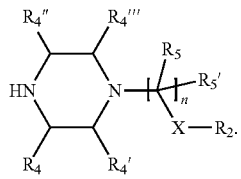 (VII)

wherein n, X, $R_1$, $R_2$, $R_3$, $R_4$, $R_{4'}$, $R_{4''}$, $R_{4'''}$, $R_5$ and $R_{5'}$ have the meanings as defined in claim 1 for the compound of formula (I), P represents a suitable protecting group, and L is a leaving group.

12. A pharmaceutical composition comprising the compound according to claim 1, or a pharmaceutically acceptable salt thereof, and a pharmaceutically acceptable carrier, adjuvant or vehicle.

13. A method of treating pain in a subject in need thereof, comprising administration of an effective amount of the compound according to claim 1.

14. The method according to claim 13, wherein the pain is selected from medium to severe pain, visceral pain, chronic pain, cancer pain, migraine, inflammatory pain, acute pain, neuropathic pain, allodynia, and hyperalgesia.

15. The process according to claim 10, wherein L is a leaving group selected from the group consisting of chloro, bromo, mesylate and tosylate.

16. The process according to claim 11, wherein L is a leaving group selected from the group consisting of chloro, bromo, mesylate and tosylate.

17. The process according to claim 11, wherein P is Boc.

18. A compound which is selected from:
N-(1-methyl-1H-pyrazol-5-yl)-1-phenethyl-N-phenylpiperidin-4-amine,
and
1-benzyl-N-(1-methyl-1H-pyrazol-5-yl)-N-phenylpiperidin-4-amine,
optionally as a stereoisomer, a racemate or a mixture of at least two stereoisomers, in any mixing ratio, or a corresponding salt thereof.

19. A pharmaceutical composition comprising the compound according to claim 18, or a pharmaceutically acceptable salt thereof, and a pharmaceutically acceptable carrier, adjuvant or vehicle.

20. A method of treating pain in a subject in need thereof, comprising administration of an effective amount of the compound according to claim 18.

21. The method according to claim 20, wherein the pain is selected from medium to severe pain, visceral pain, chronic pain, cancer pain, migraine, inflammatory pain, acute pain, neuropathic pain, allodynia, and hyperalgesia.

* * * * *

UNITED STATES PATENT AND TRADEMARK OFFICE
CERTIFICATE OF CORRECTION

| | | |
|---|---|---|
| PATENT NO. | : 10,189,828 B2 | Page 1 of 1 |
| APPLICATION NO. | : 15/531571 | |
| DATED | : January 29, 2019 | |
| INVENTOR(S) | : Carmen Almansa-Rosales et al. | |

It is certified that error appears in the above-identified patent and that said Letters Patent is hereby corrected as shown below:

On the Title Page

OTHER PUBLICATIONS: "DIckenson, et al." should be --Dickenson, et al.--

In the Claims

Column 91, Line 55: "$CR_6R_6$" should be --$CR_6R_{6'}$--

Column 93, Line 18: "1H-pyrazol-1-5-yl" should be --1H-pyrazol-5-yl--

Column 93, Line 24: "1H-pyrazol-5-" should be --1H-pyrazol-5-yl--

Signed and Sealed this
Ninth Day of April, 2019

Andrei Iancu
*Director of the United States Patent and Trademark Office*